US 9,642,694 B2

(12) United States Patent
Hoerr et al.

(10) Patent No.: US 9,642,694 B2
(45) Date of Patent: May 9, 2017

(54) DEVICE WITH ELECTROSPRAY COATING TO DELIVER ACTIVE INGREDIENTS

(71) Applicants: NANOCOPOEIA, INC., St. Paul, MN (US); REGENTS OF THE UNIVERSITY OF MINNESOTA, Minneapolis, MN (US)

(72) Inventors: Robert A. Hoerr, St. Paul, MN (US); Da-Ren Chen, Creve Coeur, MO (US); John V. Carlson, St. Michael, MN (US); David Y. H. Pui, Plymouth, MN (US)

(73) Assignees: REGENTS OF THE UNIVERSITY OF MINNESOTA, Minneapolis, MN (US); NANOCOPOEIA, INC., St. Paul, MN (US)

( * ) Notice: Subject to any disclaimer, the term of this patent is extended or adjusted under 35 U.S.C. 154(b) by 0 days.

(21) Appl. No.: 14/579,116

(22) Filed: Dec. 22, 2014

(65) Prior Publication Data
US 2015/0352592 A1 Dec. 10, 2015

Related U.S. Application Data

(63) Continuation of application No. 13/901,878, filed on May 24, 2013, now abandoned, which is a
(Continued)

(51) Int. Cl.
A61F 2/06 (2013.01)
B05B 1/14 (2006.01)
(Continued)

(52) U.S. Cl.
CPC .................. A61F 2/06 (2013.01); B05B 1/06 (2013.01); B05B 1/14 (2013.01); B05B 5/025 (2013.01);
(Continued)

(58) Field of Classification Search
None
See application file for complete search history.

(56) References Cited

U.S. PATENT DOCUMENTS 3,521,125 A 7/1970 Nelson
3,608,823 A 9/1971 Buschor
(Continued)

FOREIGN PATENT DOCUMENTS

CA 2435721 A1 8/2002
CA 2436524 A1 8/2002
(Continued)

OTHER PUBLICATIONS

Adachi et al., "High-efficiency unipolar aerosol charger using a radioactive alpha source," Aerosol Science, Industry Health and Environment, Masuda and Takahashi, eds., Pergamon Press, NY, 1990; 439-441.
(Continued)

Primary Examiner — Susan Tran
(74) Attorney, Agent, or Firm — Mueting, Raasch & Gebhardt, P.A.

(57) ABSTRACT

Devices to deliver one or more active ingredients for medical treatment may include a body of material presenting a surface including a polymer adapted to be rendered conductive such that one or more layers of electrospray particles are formable thereon or a body of conductive material presenting a surface upon which one or more layers of electrospray particles are formable thereon. A coating formed of electrospray particles may be deposited to adhere on the surface of the body of material (e.g., the coating may include one or more layers of coating material, at least one layer of the one or more layers of coating material may include an open matrix coating, the open matrix coating may include one or more active ingredients, the open matrix coating may
(Continued)

include one or more polymers and one or more active ingredients, etc.).

30 Claims, 27 Drawing Sheets

Related U.S. Application Data continuation of application No. 13/118,023, filed on May 27, 2011, now abandoned, which is a continuation of application No. 11/701,200, filed on Jan. 31, 2007, now Pat. No. 7,951,428.

(60) Provisional application No. 60/764,229, filed on Jan. 31, 2006.

(51) Int. Cl.
  B05B 1/06 (2006.01)
  B05B 5/025 (2006.01)
  B05B 5/08 (2006.01)
  B05B 7/06 (2006.01)
  B05D 1/04 (2006.01)
  B05D 1/06 (2006.01)
  C25D 21/12 (2006.01)
  C25D 5/00 (2006.01)
  C25D 17/00 (2006.01)

(52) U.S. Cl.
  CPC ............ B05B 5/08 (2013.01); B05B 7/061 (2013.01); B05D 1/04 (2013.01); B05D 1/06 (2013.01); C25D 5/003 (2013.01); C25D 5/006 (2013.01); C25D 17/007 (2013.01); C25D 21/12 (2013.01)

(56) References Cited

U.S. PATENT DOCUMENTS

| | | |
|---|---|---|
| 3,654,534 A | 4/1972 | Fischer |
| 3,905,330 A | 9/1975 | Coffee |
| 4,002,777 A | 1/1977 | Juvinall et al. |
| 4,039,145 A | 8/1977 | Felici et al. |
| 4,265,641 A | 5/1981 | Natarajan |
| 4,328,940 A | 5/1982 | Malcolm |
| 4,414,603 A | 11/1983 | Masuda |
| 4,476,515 A | 10/1984 | Coffee |
| 4,578,290 A | 3/1986 | Komon et al. |
| 4,634,057 A | 1/1987 | Coffee et al. |
| 4,659,012 A | 4/1987 | Coffee |
| 4,748,043 A | 5/1988 | Seaver et al. |
| 4,749,125 A | 6/1988 | Escallon et al. |
| 4,795,330 A | 1/1989 | Noakes et al. |
| 4,846,407 A | 7/1989 | Coffee et al. |
| 4,945,050 A | 7/1990 | Sanford et al. |
| 4,946,899 A | 8/1990 | Kennedy et al. |
| 5,036,006 A | 7/1991 | Sanford et al. |
| 5,044,564 A | 9/1991 | Sickles |
| 5,066,587 A | 11/1991 | Jones et al. |
| 5,091,205 A | 2/1992 | Fan |
| 5,100,792 A | 3/1992 | Sanford et al. |
| 5,120,657 A | 6/1992 | McCabe et al. |
| 5,141,131 A | 8/1992 | Miller, Jr. et al. |
| 5,149,655 A | 9/1992 | McCabe et al. |
| 5,179,022 A | 1/1993 | Sanford et al. |
| 5,204,253 A | 4/1993 | Sanford et al. |
| 5,219,746 A | 6/1993 | Brinegar et al. |
| 5,222,663 A | 6/1993 | Noakes et al. |
| 5,240,842 A | 8/1993 | Mets |
| 5,247,842 A | 9/1993 | Kaufman et al. |
| 5,354,556 A | 10/1994 | Sparks et al. |
| 5,371,015 A | 12/1994 | Sanford et al. |
| 5,433,865 A | 7/1995 | Laurent |
| 5,457,041 A | 10/1995 | Ginaven et al. |
| 5,464,650 A | 11/1995 | Berg et al. |
| 5,475,228 A | 12/1995 | Palathingal |
| 5,478,744 A | 12/1995 | Sanford et al. |
| 5,506,125 A | 4/1996 | McCabe et al. |
| 5,516,670 A | 5/1996 | Kuehnle et al. |
| 5,525,510 A | 6/1996 | McCabe et al. |
| 5,584,807 A | 12/1996 | McCabe |
| 5,621,605 A | 4/1997 | Inaba et al. |
| 5,655,517 A | 8/1997 | Coffee |
| 5,683,556 A | 11/1997 | Nomura et al. |
| 5,685,482 A | 11/1997 | Sickles |
| 5,702,754 A | 12/1997 | Zhong |
| 5,807,436 A | 9/1998 | Stachelhaus et al. |
| 5,813,614 A | 9/1998 | Coffee |
| 5,837,313 A | 11/1998 | Ding et al. |
| 5,846,595 A | 12/1998 | Sun et al. |
| 5,866,400 A | 2/1999 | Palsson et al. |
| 5,873,523 A | 2/1999 | Gomez et al. |
| 5,897,911 A | 4/1999 | Loeffler |
| 5,915,377 A | 6/1999 | Coffee |
| 5,973,904 A | 10/1999 | Pui et al. |
| 5,980,972 A | 11/1999 | Ding |
| 5,992,244 A | 11/1999 | Pui et al. |
| 6,068,199 A | 5/2000 | Coffee |
| 6,074,688 A | 6/2000 | Pletcher et al. |
| 6,093,557 A | 7/2000 | Pui et al. |
| 6,096,070 A | 8/2000 | Ragheb et al. |
| 6,105,571 A | 8/2000 | Coffee |
| 6,105,877 A | 8/2000 | Coffee |
| 6,120,847 A | 9/2000 | Yang et al. |
| 6,126,086 A | 10/2000 | Browner et al. |
| 6,143,037 A | 11/2000 | Goldstein et al. |
| 6,143,370 A | 11/2000 | Panagiotou et al. |
| 6,145,391 A | 11/2000 | Pui et al. |
| 6,207,195 B1 | 3/2001 | Walsh et al. |
| 6,242,369 B1 | 6/2001 | Vogt et al. |
| 6,251,136 B1 | 6/2001 | Guruwaiya et al. |
| 6,252,129 B1 | 6/2001 | Coffee |
| 6,277,448 B2 | 8/2001 | Strutt et al. |
| 6,318,640 B1 | 11/2001 | Coffee |
| 6,364,903 B2 | 4/2002 | Tseng et al. |
| 6,368,658 B1 | 4/2002 | Schwarz et al. |
| 6,386,195 B1 | 5/2002 | Coffee |
| 6,399,362 B1 | 6/2002 | Pui et al. |
| 6,419,692 B1 | 7/2002 | Yang et al. |
| 6,419,745 B1 | 7/2002 | Burkett et al. |
| 6,457,470 B1 | 10/2002 | Coffee |
| 6,517,888 B1 | 2/2003 | Weber |
| 6,579,573 B2 | 6/2003 | Strutt et al. |
| 6,595,208 B1 | 7/2003 | Coffee et al. |
| 6,632,671 B2 | 10/2003 | Unger |
| 6,645,569 B2 | 11/2003 | Cramer et al. |
| 6,669,980 B2 | 12/2003 | Hansen |
| 6,670,607 B2 | 12/2003 | Wood et al. |
| 6,684,879 B1 | 2/2004 | Coffee et al. |
| 6,737,463 B2 | 5/2004 | Yadav et al. |
| 6,743,463 B2 | 6/2004 | Weber et al. |
| 6,746,869 B2 | 6/2004 | Pui et al. |
| 6,764,720 B2 | 7/2004 | Pui et al. |
| 6,811,090 B2 | 11/2004 | Yogi et al. |
| 6,861,088 B2 | 3/2005 | Weber et al. |
| 6,880,554 B1 | 4/2005 | Coffee |
| 6,894,160 B2 | 5/2005 | Capan et al. |
| 6,933,331 B2 | 8/2005 | Yadav et al. |
| 6,989,169 B2 | 1/2006 | Ripoll et al. |
| 7,193,124 B2 | 3/2007 | Coffee |
| 7,247,338 B2 | 7/2007 | Pui et al. |
| 7,279,322 B2 | 10/2007 | Pui et al. |
| 7,498,063 B2 | 3/2009 | Pui et al. |
| 7,951,428 B2 | 5/2011 | Hoerr et al. |
| 2002/0004101 A1 | 1/2002 | Ding et al. |
| 2002/0007869 A1 | 1/2002 | Pui |
| 2002/0065553 A1 | 5/2002 | Weber |
| 2002/0151004 A1 | 10/2002 | Craig |
| 2003/0143315 A1* | 7/2003 | Pui .................. A61L 31/16 427/2.1 |
| 2003/0161937 A1 | 8/2003 | Leiby et al. |
| 2003/0232087 A1 | 12/2003 | Lawin et al. |
| 2003/0236514 A1 | 12/2003 | Schwarz |

(56) References Cited

U.S. PATENT DOCUMENTS

| | | | |
|---|---|---|---|
| 2004/0026531 A1 | 2/2004 | Sanada et al. |
| 2004/0069632 A1 | 4/2004 | Ripoll et al. |
| 2004/0081745 A1 | 4/2004 | Hansen |
| 2004/0161498 A1 | 8/2004 | Ripoll et al. |
| 2004/0173743 A1 | 9/2004 | Valaskovic et al. |
| 2004/0177807 A1 | 9/2004 | Pui et al. |
| 2004/0200729 A1 | 10/2004 | Boulais et al. |
| 2004/0234748 A1 | 11/2004 | Stenzel |
| 2004/0241315 A1 | 12/2004 | Pui et al. |
| 2005/0015046 A1 | 1/2005 | Weber et al. |
| 2005/0023368 A1 | 2/2005 | Valpey, III et al. |
| 2005/0042455 A1 | 2/2005 | Gedig et al. |
| 2005/0055078 A1 | 3/2005 | Campbell |
| 2005/0064008 A1 | 3/2005 | Bucay-Couto et al. |
| 2005/0074478 A1 | 4/2005 | Ofstead et al. |
| 2005/0075714 A1 | 4/2005 | Cheng et al. |
| 2005/0101020 A1 | 5/2005 | Salem et al. |
| 2005/0116070 A1 | 6/2005 | Ganan Calvo et al. |
| 2005/0149177 A1 | 7/2005 | Weber et al. |
| 2005/0158372 A1 | 7/2005 | O'Leary et al. |
| 2005/0175772 A1 | 8/2005 | Worsham et al. |
| 2005/0222485 A1 | 10/2005 | Shaw et al. |
| 2005/0273161 A1 | 12/2005 | Malik et al. |
| 2005/0277577 A1 | 12/2005 | Hunter et al. |
| 2005/0288774 A1 | 12/2005 | Case et al. |
| 2006/0002973 A1 | 1/2006 | Barry et al. |
| 2006/0024810 A1 | 2/2006 | Khadkikar et al. |
| 2006/0038027 A1 | 2/2006 | O'Connor et al. |
| 2006/0057259 A1 | 3/2006 | Ripoll et al. |
| 2006/0062820 A1 | 3/2006 | Gertner et al. |
| 2006/0067968 A1 | 3/2006 | Chudzik et al. |
| 2006/0078922 A1 | 4/2006 | Edwards et al. |
| 2006/0088566 A1 | 4/2006 | Parsonage et al. |
| 2006/0099235 A1 | 5/2006 | Blakstvedt et al. |
| 2006/0100568 A1 | 5/2006 | Tan |
| 2006/0177573 A1 | 8/2006 | Pui |
| 2007/0106361 A1 | 5/2007 | Epstein |
| 2007/0154554 A1 | 7/2007 | Burgermeister et al. |
| 2007/0199824 A1 | 8/2007 | Hoerr et al. |
| 2007/0278103 A1* | 12/2007 | Hoerr ............... A61L 27/34 205/80 |
| 2008/0210302 A1 | 9/2008 | Gupta |
| 2009/0104269 A1 | 4/2009 | Graham et al. |
| 2009/0266924 A1 | 10/2009 | Pui |
| 2011/0229627 A1 | 9/2011 | Hoerr et al. |
| 2013/0323403 A1 | 12/2013 | Hoerr et al. |

FOREIGN PATENT DOCUMENTS

| | | |
|---|---|---|
| CA | 2520702 A1 | 10/2004 |
| CH | 550 022 A | 6/1974 |
| CN | 1052695 A | 3/1993 |
| CN | 1651604 A | 8/2005 |
| DE | 198 46 656 A1 | 4/1999 |
| DE | 199 09 333 A1 | 11/1999 |
| EP | 0 234 841 A2 | 9/1987 |
| EP | 0 270 356 A2 | 12/1987 |
| EP | 0 258 016 A1 | 3/1988 |
| EP | 0 258 016 B1 | 3/1988 |
| EP | 0 405 884 A1 | 1/1991 |
| EP | 0 429 234 A2 | 5/1991 |
| EP | 0 429 234 B1 | 5/1991 |
| EP | 0 434 616 A1 | 6/1991 |
| EP | 0 429 234 A3 | 10/1991 |
| EP | 0 434 616 B1 | 11/1995 |
| EP | 1 355 537 A1 | 8/2002 |
| EP | 1 364 718 A1 | 11/2003 |
| ES | 2 180 405 A1 | 2/2003 |
| JP | 6-242273 A2 | 9/1994 |
| JP | 11-500047 T | 1/1999 |
| JP | 11-199471 A | 7/1999 |
| JP | 2004-531365 T2 | 10/2004 |
| MX | PA03006862 A | 10/2004 |
| WO | WO 91/00915 A1 | 1/1991 |
| WO | WO 91/07487 A1 | 5/1991 |
| WO | WO 93/07465 A1 | 4/1993 |
| WO | WO 94/12285 A1 | 6/1994 |
| WO | WO 97/10011 A1 | 3/1997 |
| WO | WO 97/13503 A1 | 4/1997 |
| WO | WO 97/49484 A1 | 12/1997 |
| WO | WO 98/03267 A1 | 1/1998 |
| WO | WO 98/42446 A1 | 10/1998 |
| WO | WO 98/56894 A1 | 12/1998 |
| WO | WO 99/03517 A1 | 1/1999 |
| WO | WO 99/30812 A1 | 6/1999 |
| WO | WO 99/30835 A1 | 6/1999 |
| WO | WO 99/31019 A1 | 6/1999 |
| WO | WO 01/87491 A1 | 11/2001 |
| WO | WO 02/060275 A1 | 8/2002 |
| WO | WO 02/060591 A1 | 8/2002 |
| WO | WO 03/028622 A2 | 4/2003 |
| WO | WO 03/082363 A1 | 10/2003 |
| WO | WO 2004/047882 A2 | 6/2004 |
| WO | WO 2005/074913 A2 | 8/2005 |
| WO | WO 2006/003504 A1 | 1/2006 |
| WO | WO 2006/086654 A2 | 8/2006 |
| WO | WO 2007/089881 A2 | 8/2007 |
| WO | WO 2007/089883 A2 | 8/2007 |
| WO | WO 2007/089881 A3 | 7/2008 |
| WO | WO 2008/094700 A2 | 8/2008 |
| WO | WO 2008/094700 A3 | 12/2008 |

OTHER PUBLICATIONS

Adachi et al., "Unipolar and Bipolar Diffusion Charging of Ultrafine Aerosol Particles," *J. Aerosol Sci.*, 1985; 16(2):109-123.

Alexis et al., "In vitro study of release mechanisms of paclitaxel and rapamycin from drug-incorporated biodegradable stent matrices," *J. Controlled Release*, 2004;98:67-74.

Büscher et al., "Performance of a unipolar 'square wave' diffusion charger with variable nt-product," *J. Aerosol Sci.*, 1994; 25(4) 651-663.

Chen et al., "Design and Evaluation of a Nanometer Aerosol Differential Mobility Analyzer (Nano-DMA)," *J. Aerosol Sci.*, 1998; 29(5/6):497-509.

Chen et al., "Electrospraying of Conducting Liquids for Monodisperse Aerosol Generation in the 4 nm to 1.8 µm Diameter Range," *J. Aerosol Sci.*, 1995; 26(6):963-977.

Chen et al., "Experimental Investigation of Scaling Laws for Electrospraying: Dielectric Constant Effect," *Aerosol Science and Technology*, 1997; 27(3):367-380.

Fuchs, "On the Stationary Charge Distribution on Aerosol Particles in a Bipolar Ionic Atmosphere," *Geodis:Pura. Appl.*, 1963; 56:185-193.

Ganan-Calvo, "Generation of Steady Liquid Microthreads and Micron-Sized Monodisperse Sprays in Gas Streams," *Phys. Rev. Lett.*, 1998; 80(2):285-288.

Ganan-Calvo, "New Microfluidic Technologies to Generate Respirable Aerosols for Medical Application," *J. of Aerosol Sci.*, 1999; 30(Suppl. 1):S541-S542.

Hoppel et al., "The Nonequililbrium Character of the Aerosol Charge Distribution Produced by Neutralizers," *Aerosol Sci. & Technol.*, 1990; 12:471-496.

International Preliminary Report on Patentability, issued Aug. 14, 2008 for International Application Serial No. PCT/US2007/002718, Jan. 31, 2007.

International Search Report, issued by the PCT on May 28, 2008 for Patent Application No. PCT/US2007/002718, (filed Jan. 31, 2007). 7 pages.

International Search Report, issued by the PCT on Aug. 24, 2007, for PCT/US2007/000270 (filed Jan. 5, 2007).

International Search Report, issued by the PCT on Nov. 7, 2008 for PCT/US2008/001410 (filed Jan. 31, 2008).

Jouyban et al., "A simple relationship between dielectric constant of mixed solvents with solvent composition and temperature," 2004, *Int. Journ. of Pharmaceutics*, 269:353-360.

Lui et al., "On unipolar diffusion charging of aerosol particles in the continuum regime," *J. Colloid Interface Sci.*, 1977; 58:142-149.

(56) References Cited

OTHER PUBLICATIONS

"Minnesota Nanotechnology Summit: Opportunities and Challenges," final program, Mar. 17, 2000, Minneapolis, MN.
Pui et al., "Nanometer Particles: A New Frontier for Multidisciplinary Research," *J. Aerosol Sci.*, 1997; 28(4) 539-544.
Pui et al., "Unipolar Diffusion Charging Ultrafine Aerosols," *Aerosol Sci. Techn.*, 1988; 8:173-187.
Puskas et al., "Polyisobutylene-Based Biomaterials," Feature Article. *J. Polym. Sci., Chem.*, 2004;42(13):3091-3109.
Ranade et al. "Physical characterization of controlled release of paclitaxel from the TAXUS™ Express$^2$™ drug-eluting stent," *J. Biomed. Mater Res.*, 2004;71A:625-634.
Ré. "Formulating Drug Delivery Systems by Spray Drying," *Drying Technology*, 2006;vol. 24, No. 4, pp. 433-446(14).
Romay et al., "Free electron charging of ultrafine aerosol particles," *J. Aerosol Sci.*, 1992; 23(7):679-692.
Romay et al., "On the combination coefficient of positive ions with ultrafine neutral particles in the transition and free-molecule regimes," *Aerosol Sci. Techn.*, 1992; 17:134-147.
Romay et al., "Unipolar Diffusion Charging of Aerosol Particles at Low Pressure," *Aerosol Sci. Techn.*, 1991; 15:60-68.
Rulison et al., "Scale-up of electrospray atomization using linear arrays of Taylor cones," *Rev. of Sci. Instrum.*, American Institute of Physics, New York, 1993; 64(3):683-686.
Salata. "Tools of Nanotechnology: Electrospray," *Current Nanoscience*, 2005; vol. 1, No. 1, pp. 25-33(9).
Shi et al., "Current advances in sustained-release system for parenteral drug delivery," *Expert Opinion on Drug Delivery*, 2005;vol. 2, No. 6; Abstract Only.
Songstad et al, "Advances in alternative DNA delivery techniques," *Plant Cell, Tissue and Organ Culture*, 1995; 40:1-15.
Szycher et al., "Drug-eluting stents to prevent coronary restenosis," 2002, http://www.implantsciences.com/pdf/IMXpaperv2-rev2.pdf; 10 pgs.
Verhoeven et al., "DSIMS characterization of a drug-containing polymer-coated cardiovascular stent," 2004, J. Controlled Release 96, 113-121.
Wiedensohler et al., "A novel unipolar charger for ultrafine aerosol particles with minimal particles losses," *J. Aerosol Sci.*, 1994; 25(4):639-650.
Willems et al., "State of the art overview and forecasts based on existing information of nanotechnology in the field of nanomaterials," *Work Documents on Nanomaterials.*, Oct. 2004; 75 pgs.
Written Opinion of the International Search Authority, issued Aug. 24, 2007 for Patent Application No. PCT/US2007/000270, filed Jan. 5, 2007.
Written Opinion of the International Searching Authority, issued May 28, 2008 for Patent Application No. PCT/US2007/002718, filed Jan. 31, 2007.
Written Opinion of the International Searching Authority, issued Nov. 7, 2008 for Patent Application No. PCT/US2008/001410, filed Jan. 31, 2008.
www.crititech.com/technology. Website dated Jun. 5, 2002, 5 pages.
Yokoyama et al., "Nanoparticle Technology for the Production of Functional Materials," *Hosokawa Powder Technology Research Institute*, 2005;KONA No. 23; 7-17.
Young et al. "Phospholipid-Stabilized Nanoparticles of Cyclosporinte A by Rapid Expansion from Supercrtitical to Aqueous Solutions," *AAPS Pharm.SciTech.*, 2003; 5(1) Article 11. pp. 1-16.

* cited by examiner

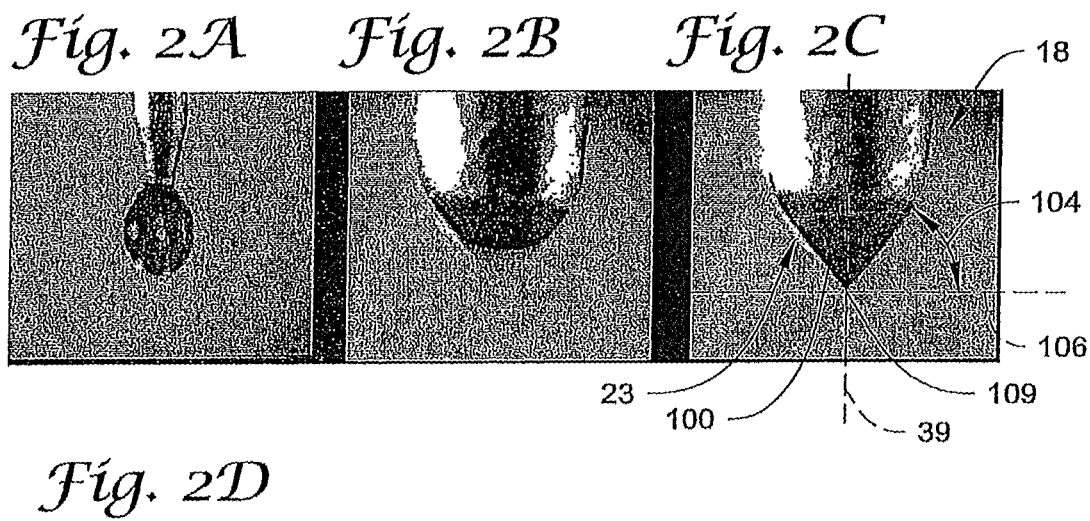
Fig. 2A  Fig. 2B  Fig. 2C
Fig. 2D
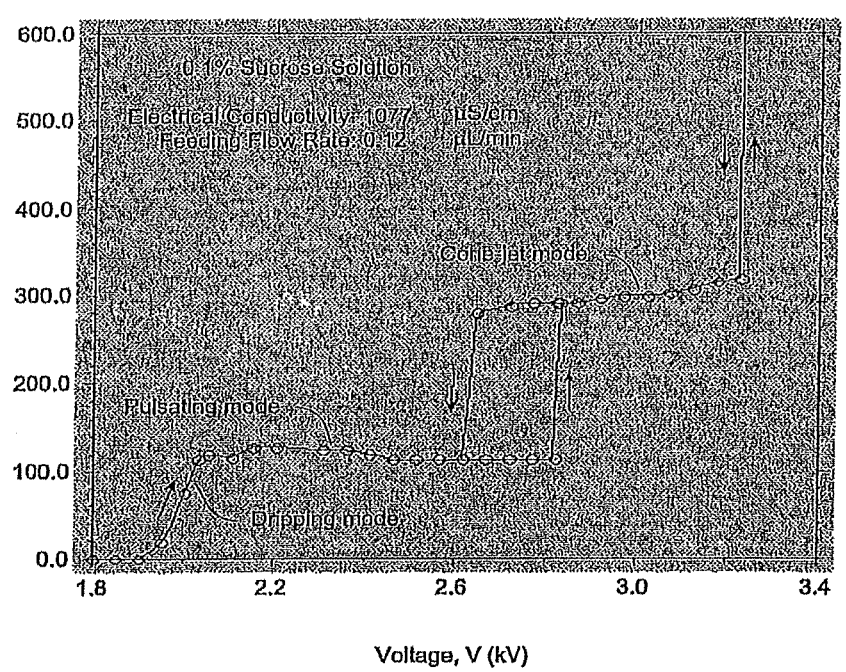

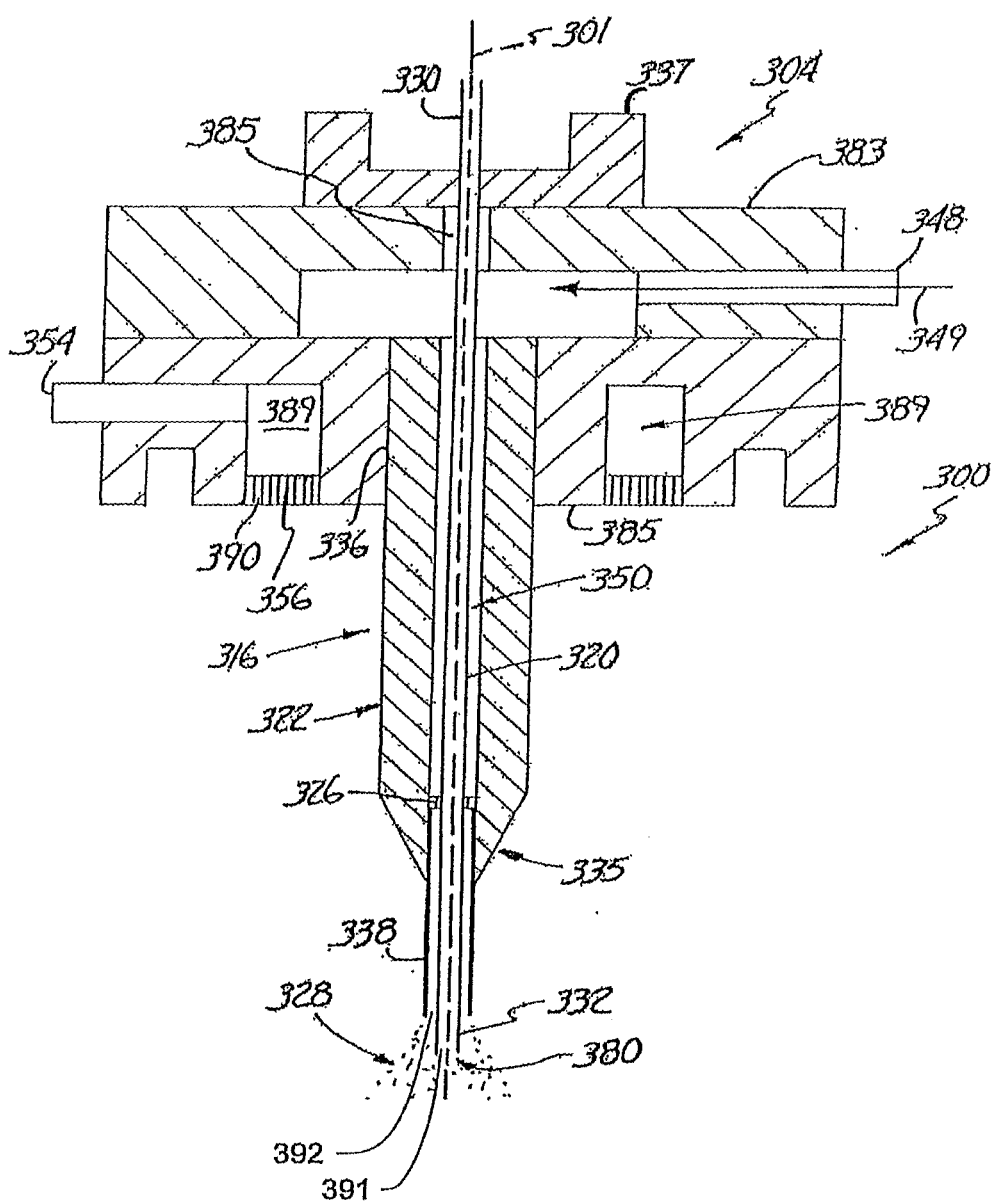

Fig. 9

| Concentration of PLCL and dexamethasone (DEX) in spray f

Fig. 11

| Measured Outcomes | Process Parameter | | | | |
|---|---|---|---|---|---|
| | Polymer concentration | Presence of drug | Conductivity of diluent solution | Polymer-to-diluent ratio | Spray distance |
| Coating weight | ↕ | ↕ | ↕ | ← | ↕ |
| Spray voltage | ↕ | ↕ | ← | ↕ | ← |
| Roundness of coating particles | ↕ |

| Coating polymer | Coating surface | No. stents per lot | Stent starting weight (μg) Mean ± SD | Coating net weight (μg) mean ± SD | Lot coating coefficient of variation |
|---|---|---|---|---|---|
| PLCL | Open matrix | 11 | 1256 ± 19 | 513.6 ± 12.9 μg | 2.5% |
| PLCL | Smooth | 12 | 1277 ± 53 | 461.7 ± 16.4 μg | 3.6% |
| Chronoflex AR | Smooth | 12 | 1266 ± 20 | 555.0 ± 15.7 μg | 2.8% |

| Coating polymer | Coating surface | Solvent(s) | Transfer efficiency |
|---|---|---|---|
| PLCL | Open matrix | Acetone | 30.5 ± 0.8% |
| PLCL | Smooth | Acetone, chloroform | 41.1 ± 1.6% |
| Chronaflex AR | Smooth | Tetrahydrofuran, methanol | 56.2 ± 1.5% |

Fig. 21

| Column | a | b | c | d | e | f |
|---|---|---|---|---|---|---|
| Stent | Crimped | Expanded | Crimped | Expanded | Crimped | Expanded |
| Coating | PLCL, open matrix | | PLCL, smooth | | Chronoflex AR, smooth | |
| View, type of image and magnification | Overall view, light microscope 10X | | | | | |
| | Survey view, SEM 100X | | | | | |
| | Outer strut surface, SEM 5000X | | | | | |
| | Outer strut surface, SEM 20,000X | | | | | |
| | Inner strut surface, SEM 20,000X | | | | | |

Fig. 24A

| Sample # | Coating properties | Stent | Solids% | Solvent | IF(ul/min) | Outer | OF(ul/min) | D(Nozzle to stent)(mm) | # of Passes | Weight (ug) |
|---|---|---|---|---|---|---|---|---|---|---|
| 241 | Open | BSC | 0.9%SIBS+0.1%PTx | 85%THF14%MEOH | 1.5 | 14%MeOH86%THF: MG1 50/50 | 4 | 16 | 2 | 330 |
| 256 | Closed | BSC | 0.81%SIBS+0.09%PTx | 90%MG1:10%Toluene | 3.5 | 10%MeOH90%THF | 5 | 8 | 1 | 330 |
| 382 | with DEX | BSC | 0.9%SIBS+0.1%PTx+0.1%DEX | 85%THF14%MEOH | 2.5 | | | 16 | 1 | 390 |
| 219 | Drug-ebed | BSC | 0.9%SIBS+0.1%PTx | 85%THF14%MEOH | 2.5 | 10%MeOH90%THF | 1 | 12 | 1 | 300 |

| Sample# | Coating properties | Stent | Solids% | Solvent | IF(ul/min) | Outer | OF(ul/min) | D(Nozzle to stent)(mm) | # of Passes | Weight (ug) |
|---|---|---|---|---|---|---|---|---|---|---|
| 279 | Open | BSC | 0.9%SIBS+0.1%PTx | 99%THF | 3 | 15%MEOH85%THF | 4 | 16 | 1 | 320 |
| 318 | Closed | BSC | 0.9%SIBS+0.1%PTx | 99%THF | 1 | 15%MEOH85%THF | 8 | 16 | 1 | 120 |

(279)

(318)

| Sample # | Coating properties | Stent | Solids% | Solvent | IF(ul/min) | Outer | OF(ul/min) | D(Nozzle to stent)(mm) | # of Passes | Weight (ug) |
|---|---|---|---|---|---|---|---|---|---|---|
| 326 | Closed | BSC | 2.25%SIBS+0.25%PTx | 97.5%THF | 1 | 15%MEOH 85%THF | 9 | 20 | 1 | 210 |

(326)

| Sample# | Coating properties | Stent | Solids% | Solvent | IF(ul/min) | Outer | OF(ul/min) | D(Nozzle to stent)(mm) | # of Passes | Weight (ug) |
|---|---|---|---|---|---|---|---|---|---|---|
| 308 | Open | BSC | 4.5%SIBS+0.5%PTx | 95%THF | 0.85 | 15%MEOH85%THF | 5 | 15 | 1 | 410 |
| 373 | Closed | BSC | 0.9%SIBS+0.1%PTx | 20%MG5:80%Toluene | 1 | 15%MEOH85%THF | 3 | 20 | 1 | 110 |

(308)

(373)

| Sample# | Coating properties | Stent | Solids% | Solvent | IF(ul/min) | Outer | OF(ul/min) | D(Nozzle to stent)(mm) | # of Passes | Weight (ug) |
|---|---|---|---|---|---|---|---|---|---|---|
| 593 | Open | Pulse | 5 PLCL+.5DEX | Acetone | 1.5 | Acetone + HNO3 | 5 | 12 | 1 | 530 |
| 614 | Close | Pulse | 5 PLCL+.5DEX | Acetone | 0.75 | 40 Acetone/60 CHCL3 | 10 | 10 | 1 | 490 |

(593)

(614)

| Sample# | Coating properties | Stent | Solids% | Solvent | IF(ul/min) | Outer | OF(ul/min) | D(Nozzle to stent)(mm) | # of Passes | Weight (ug) |
|---|---|---|---|---|---|---|---|---|---|---|
| 69 | Close | spring | 5 PLCL | Acetone | 0.75 | Acetone/chloroform 50/50 | 10 | 8 | 1 | 590 |
| 76 | Open | BSC | 5 PLCL | Acetone | 1 | Acetone | 5 | 8 | 1 | 820 |

(69)

(76)

| Sample# | Coating properties | Stent | Solids% | Solvent | IF(ul/min) | Outer | OF(ul/min) | D(Nozzle to stent)(mm) | #of Passes | Weight (ug) |
|---|---|---|---|---|---|---|---|---|---|---|
| 635 | Close | Pulse | 2 CFR/2 DEX | THF/MEOH 5/1 | 2 | THF/MEOH 5/1 | 8 | 8 | 1 | 550 |

(635)

| Sample# | Coating properties | Stent | Solids% | Solvent | IF(ul/min) | Outer | OF(ul/min) | D(Nozzle to stent)(mm) | # of Passes | Weight (ug) |
|---|---|---|---|---|---|---|---|---|---|---|
| 275 | Open | BSC | 0.9%SIBS+0.1%PTx | 69.7%THF,29.3%MEK | 1 | 10%MeOH,90%THF | 2 | 12 | 1 | 190 |

(275)

| Sample# | Coating properties | Stent | Solids% | Solvent | IF(ul/min) | Outer | OF(ul/min) | D(Nozzle to stent)(mm) | #of Passes | Weight (ug) |
|---|---|---|---|---|---|---|---|---|---|---|
| 130 | 3rd-nozzle | BSC | 2 Dexa | 2/3 blend of ETOH/Acetone | 0.75 | 5% PLCL in acetone | 1.5 | 8 | 1 | 1020 |

(130)

DEVICE WITH ELECTROSPRAY COATING TO DELIVER ACTIVE INGREDIENTS

CROSS-REFERENCE TO RELATED APPLICATIONS

This application is a continuation application of U.S. patent application Ser. No. 13/901,878, filed on May 24, 2013, which is a continuation application of U.S. patent application Ser. No. 13/118,023, filed on May 27, 2011, which is a continuation of U.S. patent application Ser. No. 11/701,200, filed Jan. 31, 2007, (now U.S. Pat. No. 7,951, 428) which claims the benefit of U.S. Provisional Application Ser. No. 60/764,229 filed 31 Jan. 2006, entitled "Electrospraying apparatus and method for coating objects," all of which are incorporated herein by reference in their entirety.

STATEMENT OF GOVERNMENT RIGHTS

The present invention was made with support from the National Science Foundation (NSF) under Grant No. 0512496. The government may have certain rights in this invention.

BACKGROUND OF THE INVENTION

The present invention relates to coating objects, and more particularly, the present invention relates to coating objects (e.g., medical devices) using electrospray technology.

It is often beneficial to coat objects (e.g., medical devices) so that the surfaces of such devices have desired properties or provide desired effects. For example, it is useful to coat medical devices to provide for the localized delivery of therapeutic agents to target locations within the body, such as to treat localized disease (e.g., heart disease) or occluded body lumens. Local drug delivery may be achieved, for example, by coating balloon catheters, stents, and the like with therapeutic agent to be locally delivered. The coating of medical devices may provide for controlled release, which includes long-term or sustained release, of a bioactive material.

Aside from facilitating localized drug delivery, medical devices are coated with materials to provide beneficial surface properties. For example, medical devices are often coated with radiopaque materials to allow for fluoroscopic visualization during placement in the body. It is also useful to coat certain devices to achieve enhanced biocompatibility and to improve surface properties such as lubriciousness.

Further, for example, it is often beneficial to coat stents, e.g., for the controlled release of pharmacological agents, surface property control and effects, etc. Stents are implanted within vessels in an effort to maintain the patency thereof by preventing collapse and/or impeding restenosis. For example, implantation of a stent may be accomplished by mounting the stent on the expandable portion of a balloon catheter, maneuvering the catheter through the vasculature so as to position the stent at the treatment site within the body lumen, and inflating the balloon to expand the stent so as to engage the lumen wall. The stent deforms in the expanded configuration allowing the balloon to be deflated and the catheter removed to complete the implantation procedure. Further, for example, the use of self-expanding stents obviates the need for a balloon delivery device. Instead, a constraining sheath that is initially fitted above the stent is simply retracted once the stent is in position adjacent the treatment site. Stents and stent delivery catheters are well known in the art and the various configurations thereof makes it impossible to describe each and every stent structure or related materials.

The success of a stent placement can be assessed by evaluating a number of factors, such as thrombosis, neointimal hyperplasia, smooth muscle cell migration, and proliferation following implantation of the stent, injury to the artery wall, overall loss of lumenal patency, stent diameter in vivo, thickness of the stent, and leukocyte adhesion to the lumenal lining of stented arteries. The chief areas of concern are early subacute thrombosis and eventual restenosis of the blood vessel due to intimal hyperplasia.

Therapeutic pharmacological agents have been developed to address some of the concerns associated with the placement of the stent. It is often desirable to provide localized pharmacological treatment of the vessel at the site being supported by the stent. As it would be convenient to utilize the implanted stent for such purpose, the stent may serve both as a support for a lumenal wall as well as a delivery vehicle for the pharmacological agent.

Conventionally, coatings have been applied to objects such as medical devices, including stents, by processes such as dipping, spraying, vapor deposition, plasma polymerization, as wells as electroplating and electrostatic deposition. Although many of these processes have been used to produce satisfactory coatings, there are numerous potential drawbacks associated therewith.

For example, it is often difficult to achieve coatings of uniform thicknesses, both on the individual parts and on batches of parts. Also, many coating materials are otherwise difficult to use, such as those that are incompatible, insoluble, unsuspendable, or that are unstable coating solutions.

Further, for example, many coating processes result in coatings that do not provide a uniform drug dose per medical device. Further, such conventional methods have generally failed to provide a quick, easy, and inexpensive way of providing drugs onto a stent. For example, deficiencies of such conventional methods are, at least in part, related to the control of the coating process (e.g., the ability to control the coating uniformity and thickness, the ability to control the size of particles used to coat the device, the control of the coating so as to control the rate of the release of the drug upon implantation of the stent, etc.). Likewise, in many processes, the coating materials are fairly costly, and in many coating processes such coating materials are wasted due to the type of coating methods being used.

Therefore, the need for an effective method and system of coating objects such as medical devices exists.

SUMMARY OF THE INVENTION

The methods and systems according to the present invention provide for the coating of objects (e.g., coating of medical devices such as stents and catheters, depositing film on any object for texturing the surface thereof, providing a protective layer on an object, constructing an active or passive layer of an integrated circuit, etc.).

A method of coating at least a portion of an object according to the present invention includes providing an object in a defined volume (e.g., the object includes at least one surface). One or more nozzle structures are provided. Each nozzle structure includes at least an inner opening and an outer opening concentric with the inner opening (e.g., the inner opening and the outer opening terminate at the dispensing end of each nozzle structure). The method further includes selecting a type of coating to be applied to the at least one surface of the object (e.g., one of an open matrix coating, a closed film coating, and an intermediate matrix coating). A first flow of a liquid spray composition is provided to the inner opening (e.g., the first flow of liquid spray composition includes at least one of a biologically active ingredient, a polymer, and a solvent). A second flow of a liquid diluent composition is provided to the outer opening (e.g., the second flow of the liquid diluent composition includes at least one solvent, such as a high dielectric solvent when applying an open matrix coating). A plurality of charged coating particles are generated forward of the dispensing end of each nozzle structure to apply a coating to the at least one surface of the object. The plurality of charged coating particles are dispensed as a stream of a plurality of microdroplets having an electrical charge associated therewith from the dispensing end of each nozzle structure by creating a cone-jet from the first and second flow at the dispensing end of each nozzle using a nonuniform electrical field between the dispensing end of each nozzle structure and the object. The plurality of charged coating particles (e.g., having a nominal diameter of less than 10 micrometers) are formed as the microdroplets evaporate. The method further includes moving the plurality of charged coating particles towards the at least one surface of the object to apply the coating thereon using the nonuniform electrical field created between the dispensing end of each nozzle structure and the object. Further, a flow rate of the second flow of the liquid diluent composition is controlled relative to a flow rate of the first flow of the liquid spray composition such that the plurality of charged coating particles forms the selected type of coating on the at least one surface of the object (e.g., a uniform open matrix coating, a uniform closed film coating, etc.).

Another method of coating at least a portion of an object includes providing an object in a defined volume (e.g., the object including at least one surface) and providing one or more nozzle structures. Each nozzle structure includes at least an inner opening and an outer opening concentric with the inner opening (e.g., the inner opening and the outer opening terminate at the dispensing end of each nozzle structure). A first flow of a liquid spray composition is provided to the inner opening (e.g., the first flow of liquid spray composition includes at least a polymer and a solvent, such as a low dielectric constant solvent, suitable to at least partially dissolve the polymer, and may also include biologically active material). A second flow of a liquid diluent composition is provided to the outer opening (e.g., the second flow of the liquid diluent composition includes at least one solvent such as a high dielectric constant solvent). At least in one embodiment, the liquid diluent composition has a conductivity greater than 1 μS cm$^{-1}$. A plurality of charged coating particles are generated forward of the dispensing end of each nozzle structure to apply a coating to the at least one surface of the object. Generating the plurality of charged coating particles includes dispensing a stream of a plurality of microdroplets having an electrical charge associated therewith from the dispensing end of each nozzle structure by creating a cone-jet from the first and second flow at the dispensing end of each nozzle using a nonuniform electrical field between the dispensing end of each nozzle structure and the object. The plurality of charged coating particles are moved towards the at least one surface of the object to apply an open matrix coating thereon using the nonuniform electrical field created between the dispensing end of each nozzle structure and the object.

Yet another method of coating at least a portion of an object includes providing an object in a defined volume (e.g., the object includes at least one surface) and providing one or more nozzle structures (e.g., each nozzle structure includes one or more openings terminating at a dispensing end of each nozzle structure). One or more flows of liquid compositions are provided to the openings and a plurality of charged coating particles are generated forward of the dispensing end of each nozzle structure to apply a coating to the at least one surface of the object. Generating the plurality of charged coating particles includes dispensing a stream of a plurality of microdroplets having an electrical charge associated therewith from the dispensing end of each nozzle structure by creating a cone-jet from the one or more flows at the dispensing end of each nozzle using a nonuniform electrical field between the dispensing end of each nozzle structure and the object. The plurality of charged coating particles having a nominal diameter of less than 10 micrometers are formed as the microdroplets evaporate. Using the nonuniform electrical field between the dispensing end of each nozzle structure and the object to generate the plurality of charged coating particles includes applying an electrical potential difference between the dispensing end of each nozzle structure and the object being coated so as to create the cone-jet from the one or more flows at the dispensing end of each nozzle structure. The method further includes adjusting the electrical potential difference between the dispensing end of each nozzle structure and the object being coated as the thickness of the coating increases so as to maintain a stable cone-jet at the dispensing end of each nozzle structure. Systems for carrying out this method are also provided.

Still another method of coating at least a portion of an object includes providing an object in a defined volume (e.g., the object includes at least one surface) and providing one or more nozzle structures. Each nozzle structure includes one or more openings terminating at a dispensing end of each nozzle structure. One or more flows of liquid compositions are provided to the openings and a plurality of charged coating particles are generated forward of the dispensing end of each nozzle structure to apply a coating to the at least one surface of the object. Generating the plurality of charged coating particles includes dispensing a stream of a plurality of microdroplets having an electrical charge associated therewith from the dispensing end of each nozzle structure by creating a cone-jet from the one or more flows at the dispensing end of each nozzle using a nonuniform electrical field between the dispensing end of each nozzle structure and the object. The plurality of charged coating particles having a nominal diameter of less than 10 micrometers are formed as the microdroplets evaporate. The method further includes detecting at least one characteristic associated with the cone-jet, determining the stability of the cone-jet based on the at least one characteristic, and adjusting one or more process parameters to maintain a stable cone-jet.

In one or more embodiments of the method, detecting at least one characteristic associated with the cone-jet includes imaging the cone-jet to determine at least one angle associated therewith, detect one or more flutters in the cone-jet, and/or detect bubbles in the one or more flows. Systems for carrying out this method are also provided.

In yet another method of coating at least a portion of an object, the method includes providing an object in a defined volume and providing one or more nozzle structures. Each nozzle structure includes a first inner opening, a second intermediate opening concentric with the inner opening, and a third outer opening concentric with the first inner opening and second intermediate opening. The first inner opening, the second intermediate opening, and the third outer opening terminate at the dispensing end of the nozzle structure. The method further includes providing a first flow of a liquid spray composition to the first inner opening (e.g., the first flow of liquid spray composition includes at least one biologically active ingredient), providing a second flow of a liquid spray composition to the second intermediate opening (e.g., the second flow of liquid spray composition includes at least one polymer and a solvent suitable for at least partially dissolving the polymer), and providing a third flow of a liquid diluent composition to the third outer opening (e.g., the third flow of the liquid diluent composition includes at least one solvent). A plurality of charged coating particles are generated forward of the dispensing end of each nozzle structure to apply a coating to the at least one surface of the object. Generating the plurality of charged coating particles includes dispensing a stream of a plurality of microdroplets having an electrical charge associated therewith from the dispensing end of each nozzle structure by creating a cone-jet from the first, second, and third flows at the dispensing end of each nozzle structure using a nonuniform electrical field between the dispensing end of each nozzle structure and the object. The plurality of charged coating particles having a nominal diameter of less than 10 micrometers are formed as the microdroplets evaporate. The plurality of charged coating particles include biologically active material at least partially encapsulated by the polymer.

Further, a coating sprayed by electrospray from a cone-jet provided with one or more flows of liquid compositions that include at least two active ingredients (e.g., the at least two active ingredients in the one or more flows exist in a predetermined ratio) is described. The coating includes a plurality of particles adherent to one another but discrete. The plurality of particles have a nominal diameter of less than 500 nanometers and each particle includes the at least two active ingredients in substantially the same predetermined ratio as the at least two active ingredients exist in the one or more flows.

In one or more embodiments of the coating, the plurality of particles have a nominal diameter of less than 200 nanometers; the at least two active ingredients include a polymer and biologically active material; the at least two active ingredients are uniformly distributed through the thickness of the coating; and open regions are present throughout the thickness of the coating.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

BRIEF DESCRIPTION OF THE DRAWINGS

FIGS. 2A-2C are images of a capillary electrospray dispensing end (e.g., spray head) progressing from the start of spray (FIG. 2A) to the "pulsating" mode (FIG. 2B) to the "cone-jet" mode (FIG. 2C) according to the present invention.

FIG. 2D is a graph showing a current versus voltage curve for electrospray of a particular solution.

FIG. 7A shows a more detail diagram of one embodiment of a dual opening electrospray dispensing apparatus according to the present invention that may be controlled for applying one or more of the types of coatings such as generally shown in FIGS. 3A-3C.

Figure 9:
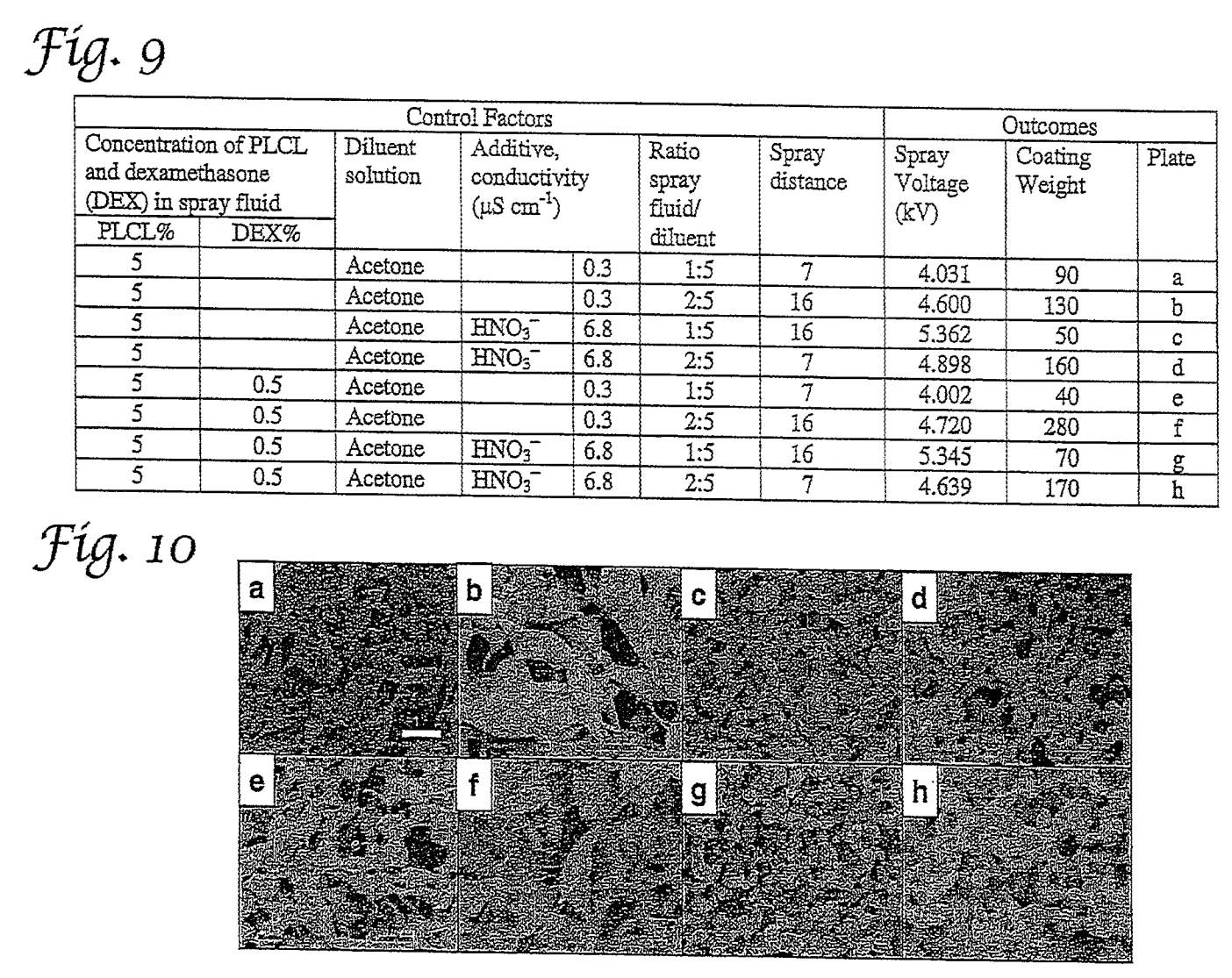

FIG. 9 shows a table of experimental conditions and outcome measures to assess impact of process parameters on achieving desired coatings according to one or more examples provided herein.

FIG. 10, which includes images a-h, show design of experiment image results for the parameter sets outlined in FIG. 9 according to one or more examples provided herein.

FIG. 11 shows a table of the relationship of process parameters to experimental outcome variables according to one or more examples provided herein.

FIG. 21 shows a table for use in describing the images of FIG. 20, images a-f, according to one or more examples provided herein.

FIG. 24A shows a table of solutions and parameters used in the application of one or more coatings according to one or more examples provided herein.

DETAILED DESCRIPTION OF THE EMBODIMENTS

The present invention shall generally be described with reference to FIGS. 1-8. Various examples shall then be described with reference to FIGS. 9-34. It will become apparent to one skilled in the art that elements from one embodiment may be used in combination with elements of other embodiments, and that the present invention is not limited to the specific embodiments described herein but only as described in the accompanying claims. For example, one or more parameters may be used for providing control of one or more coating methods described herein.

The present invention provides for coated objects (e.g., coated stent structures) and also systems and methods for coating objects (e.g., coating of medical devices, depositing a film on any object such as for texturing the surface thereof, providing a protective layer on an object, providing a textured surface to improve cellular adherence and/or biocompatibility, constructing an active or passive layer of an integrated circuit, etc.). With use of the present invention, for example, selected types of coatings having uniform properties can be accomplished. Further, the present invention provides for the efficient and cost effective use of coating materials.

Figure 1:
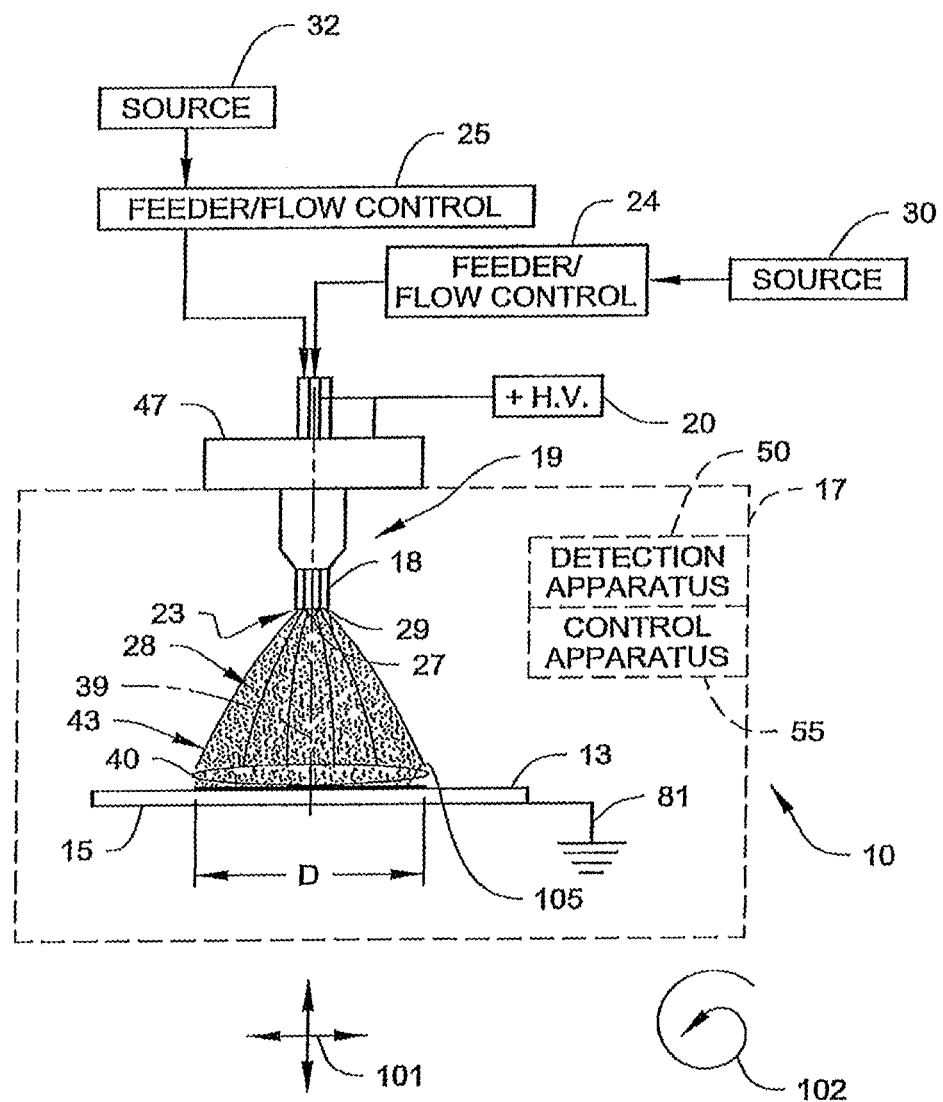
FIG. 1 is a general diagram illustrative of one embodiment of an object coating system, e.g., a nanoparticle generator system using electrospray techniques for coating surfaces that includes a dual opening nozzle in accordance with the present invention.

An electrospray coating system, such as electrospray coating system 10 illustratively shown in FIG. 1, can be controlled so as to provide for one or more selected types of coatings according to the present invention. For example, the electrospray coating system 10 may be controlled to provide an open matrix coating on one or more surface portions of an object, a closed film coating on one or more surface portions of an object, or an intermediate matrix coating on one or more surface portions of an object.

Figure 3A:
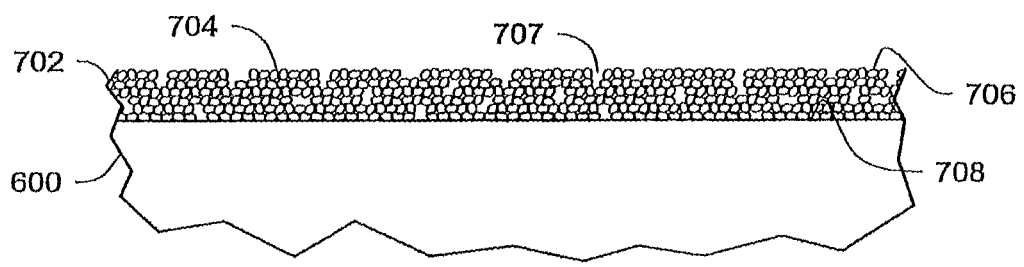
FIGS. 3A-3C illustratively show three types of coatings that may be selected and/or applied according to the present invention including an open matrix coating in FIG. 3A, a closed film coating in FIG. 3B, and an intermediate matrix coating in FIG. 3C.
Figure 3B:
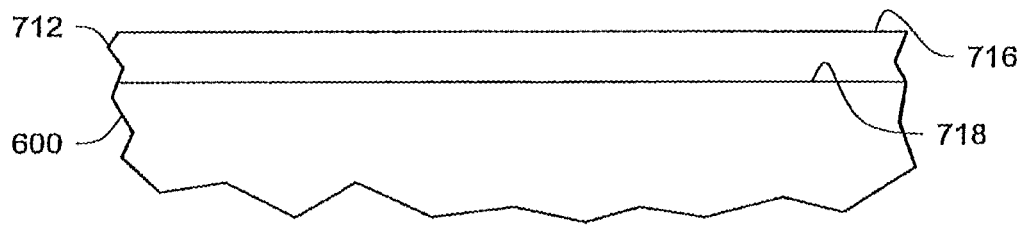
Figure 3C:
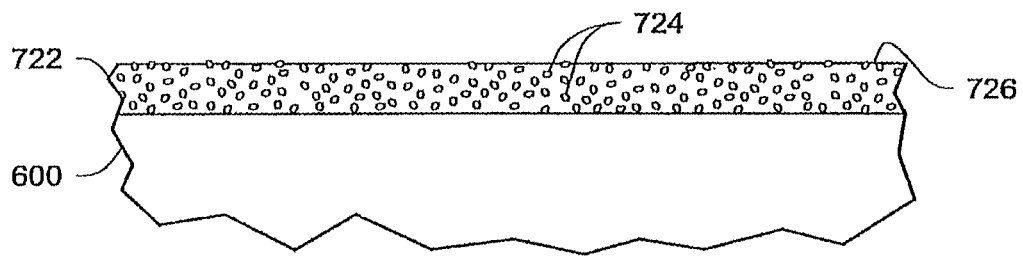

FIGS. 3A-3C illustratively show three types of coatings that may be selected and/or applied according to the present invention including an open matrix coating in FIG. 3A, a closed film coating in FIG. 3B, and an intermediate matrix coating in FIG. 3C. Such coatings can be selected for application on one or more surface portions of an object 600. Such selection may be performed manually or automatically. Generally, the selection of the type of coating to be applied may include a user determining that it is desirable to use one or more of the types of coatings to obtain one or more types of functionality provided by the coating. Selection may involve a user operating a system and setting various parameters or selecting various compositions to be used in the spraying process so as to apply a particular selected coating, or may include user selection of a coating type on a system such that the system automatically selects one or more parameters or various compositions to be used in the spraying process so as to apply a particular selected coating, or a combination of both.

Generally as described herein, the selected coating type may be applied using two or more different types of liquid compositions (e.g., a liquid spray composition and a liquid diluent composition provided at two or more concentric openings at a dispensing end of a nozzle structure) and/or under one or more conditions or controlled parameters according to the present invention. For example, as described herein, an open matrix coating may be applied to a surface of an object by controlling the type of liquid diluent composition and/or the conductivity of a composition provided at an outer opening of a dual opening nozzle structure, or by controlling the ratio of a liquid diluent composition provided at an outer opening of a dual opening nozzle structure to the liquid spray composition provided at an inner opening of a dual opening nozzle structure.

As used herein, an open matrix coating refers to a coating wherein a supermajority (i.e., greater than two-thirds) of the particles used to create the coating are visibly discrete but attached creating a relatively irregular coating compared to a closed film coating. In other words, when an open matrix coating is viewed using microscopy, the particles used to form the coating can be visually separated by the viewer into discrete particles even though such particles are attached, or otherwise coupled, to one or more other particles of the coating.

An open matrix coating 702 is illustratively shown in FIG. 3A applied to surface 708. The open matrix coating 702 includes discrete particles 704 attached, or otherwise coupled, to one or more other particles 704 of the coating 702.

The open matrix coating has visibly distinct open regions 707 appearing darker than the surface 706 of the coating 702 when viewed using scanning electron microscopy (SEM). Such opening regions 707 extend at least one or more nominal diameters of the particles 704 deeper into the surface 706 (e.g., from the upper most surface of the outer most particles at the surface 706 of the coating 702). At least in one embodiment, such opening regions 707 exist throughout the thickness of the coating 702 as shown in FIG. 3A. Further, particles with distinct boundaries and shape similar to those seen on the surface 706 of the coating are visible using SEM in one or more planes beneath the surface 706 of the coating.

At least in one embodiment of the open matrix coating, the particles are substantially round particles. As used herein, substantially round particles refers to particles that are not elongated fiber particles; elongated fiber particles as used herein are fiber particles that have a body length that is at least ten (10) times the diameter of a maximum cross-section taken at any point along the length of the particle. In other words, a substantially round particle does not have an elongated body but is more spherically shaped, although such particles will not necessarily be spherical.

Generally, the surface area at the upper surface 706 of the coating 702 is a rough surface that can be characterized in one or more different manners. One manner of characterizing a rough surface of the open matrix coating is based on the cross-section particle size of the particles of the coating being deposited. At least in one embodiment, the nominal cross-section particle size is represented by the nominal diameter through the center of the particles. In one embodiment, the nominal diameter for particles of a rough open matrix coating according to the present invention is in the range of about 1 nm to about 2000 nm. In another embodiment, the cross-section nominal diameter through the center of the particles is greater than about 10 nm, in another embodiment less than about 1000 nm, in another embodiment less than about 500 nanometers, and in another embodiment less than about 200 nm.

Alternatively, or in addition to other manners of characterizing the rough surface of the coating 702, a rough surface may be characterized based on a comparison of the surface area of the rough surface relative to the surface area of a completely smooth surface (i.e., a surface with no structure, e.g., valleys, peaks, etc.) having a substantially identical shape as the rough surface, e.g., the shape of the structure upon which a rough portion is formed. In one embodiment of the present invention, a rough surface is a generally homogenous surface (i.e., a surface structure without any substantial irregularities from one part of the surface to another part of the surface such as, for example, deep depressions, large spikes, unusually large particles compared to the other particles of the layer, etc.) that has a surface area greater than about 1.2 times the surface area of a completely smooth surface having a substantially identical shape (i.e., substantially identical shapes having the same base dimensional characteristics, e.g., in the case of a planar surface the occupancy area of both the completely smooth and rough surface are equivalent). However, the surface shape may be of a planar shape, a curved shape, or any other shape. In yet another embodiment, the roughness of the surface has a surface area that is greater than about 1.5 times the surface area of a completely smooth surface having a substantially identical shape.

For example, as shown in FIG. 3A, the rough surface 706 of coating 702 has a generally planar shape. The surface area of the rough surface 706 can be compared to a surface area (XY) (only the x axis is shown with the y axis extending into the page) of a completely smooth surface 708 having a planar shape, i.e., a shape identical to the shape of the rough surface 706. Therefore, at least in one embodiment, the surface area of rough surface 706 of the coating 702 is greater than about 1.2(XY). Yet further, in another embodiment, the surface area of rough surface 706 of the coating 702 is greater than about 2.0(XY).

As used herein, a closed film coating refers to a coating wherein a supermajority (i.e., greater than two-thirds) of the particles used to create the coating are not visibly discrete, but rather have flowed together to form a relatively smooth coating as compared to an open matrix coating. In other words, when a closed film coating is viewed using microscopy, the particles used to form the coating are not visually separable into discrete particles by the viewer but rather the coating is seen as a generally smooth coating with no or little irregularity.

A closed film coating 712 is illustratively shown in FIG. 3B. The closed film coating 712 includes substantially no discrete particles, but rather the coating 712 has an upper surface 716 that is smooth and flowing. In other words, the surface area of the smooth surface 716 is substantially equal to a surface area (XY) (only the x axis is shown with the y axis extending into the page) of a completely smooth surface 718 having an identical shape, or at least is less than about 1.1(XY).

As used herein, an intermediate matrix coating refers to a coating wherein less than a supermajority (i.e., less than two-thirds) of the particles used to create the coating are visibly discrete, however, more than superminority (i.e., more than one third) of the particles are visibly discrete (e.g., in such a coating, many particles are visibly discrete with flowing material generally existing therebetween). In other words, when an intermediate matrix coating is viewed using microscopy, between one third to two thirds of the particles used to form the coating are visually separable into discrete particles by the viewer, with the remainder of the coating being a flowing material connecting such particles forming a coating that is slightly irregular compared to a closed film coating but less irregular than an open matrix coating.

An intermediate matrix coating 722 is illustratively shown in FIG. 3C. The intermediate matrix coating 722 includes some visibly discrete particles 724, and has an upper surface 726 that is slightly rough. In other words, the surface area of the slightly rough surface 726 is less rough than an open matrix coating but rougher than a closed film coating.

As used herein, when reference is made to a uniform coating, the uniformity extends through the entire thickness of a selected coating unless otherwise stated. For example, the structure of a uniform open matrix coating (i.e., wherein the particles are visibly discrete but connected to one or more other particles) is substantially the same throughout the entire thickness of the coating (e.g., the particles are visibly discrete at the surface of an object being coated as well as throughout the coating including the upper rough surface of the open matrix coating).

One will recognize that two or more selected types of coatings may be applied to create a combined coating of two or more selected coatings (e.g., a closed film coating overlaid with an open matrix coating). In such a case, uniformity of such selected layers would apply to the respective layers.

At least in one embodiment, an open matrix coating may be sprayed by electrospray from a cone-jet provided with one or more flows of liquid compositions (e.g., such as using a dual opening nozzle structure such as described herein, a single opening nozzle structure, etc). The one or more flows include at least two active ingredients. The at least two active ingredients in the one or more flows exist in a predetermined ratio. The coating includes a plurality of particles adherent to one another but discrete such as described above with reference to an open matrix coating. The plurality of particles have a nominal diameter of less than 500 nanometers, and may even have a nominal diameter of less than 200 nanometers. Each particle of the coating includes the at least two active ingredients in substantially the same predetermined ratio as the at least two active ingredients exist in the one or more flows. As used in this context, the term substantially refers to a deviation of +/−20%.

In one or more further embodiments of such a coating, the at least two active ingredients include a polymer and biologically active material (e.g., the biologically active ingredient may be encapsulated by the polymer or they may exist in more of a matrix form. Further, the at least two active ingredients are uniformly distributed through the thickness of the coating and open regions like those described with reference to the open matrix coating are present throughout the thickness of the coating.

One embodiment of an electrospray coating system 10 according to the present invention is shown in FIG. 1. The electrospray coating system 10 employs the generation of particles, such as, for example, nanoparticles, for use in coating objects, such as medical devices (e.g., coating such devices with polymers and/or drugs, with one selected coating or more than one selected coating).

As further described herein, the systems and methods according to the present invention may use one or more electrospray apparatus having dual opening nozzle structures, or one or more nozzle structures that have more than two openings at the dispensing ends thereof, such as that previously described in U.S. Pat. No. 6,093,557 to Pui, et al., entitled "Electrospraying Apparatus and Method for Introducing Material into Cells," issued 25 Jul. 2000 (e.g., dual capillary configurations), and also described in the papers entitled, "Electrospraying of Conducting Liquids for Dispersed Aerosol Generation in the 4 nm to 1.8 µm Diameter Range" by Chen, et al., *J. Aerosol Sci.*, Vol. 26, No. 6, pp. 963-977 (1995), and entitled "Experimental Investigation of Scaling Laws for Electrospraying: Dielectric Constant Effect" by Chen, et al., *Aerosol Science and Technology*, 27:367-380 (1997), or may use a single or multiple nozzle structure electrospray apparatus such as described in U.S. Patent Application US-2002-0007869-A1, entitled "High Mass Throughput Particle Generation Using Multiple Nozzle Spraying," published on 24 Jan. 2002, or may use one or more nozzle structures described in US 2003/0143315 A1, entitled "Coating Medical Devices," published 31 Jul. 2003, which are all hereby incorporated in their entirety by reference thereto.

As shown in FIG. 1, the illustrative electrospray coating system 10 employs a dispensing apparatus 19 to establish a spray of coating particles 28 (e.g., spray of microdroplets which evaporate to form a spray of coating particles). The dispensing apparatus 19 includes at least one nozzle structure 18 that includes at least two concentric openings 27, 29 (e.g., concentric about axis 39) that terminate at the dispensing end 23 thereof. Openings that terminate at the dispensing end 23 do not need to terminate in a single plane (e.g., a plane orthogonal to axis 39 along which the nozzle structure 18 extends. Rather, the termination of one of the openings may be closer to the object 15 being coated than the other (e.g., the inner opening may terminate closer to the object 15). The openings receive source material to establish the spray of coating particles 28 forward of the dispensing end 23, e.g., in the direction of the object 15 to be coated. The coating particles 28 are moved toward at least one surface 13 of the object 15 (e.g., medical device) to form a coating 105 thereon.

The object 15 is located in a defined volume (shown generally by the dashed line 17) where the coating particles 28 are provided. The defined volume 17 may, for example, be a reactor chamber, a chamber of a coating system, a vacuum chamber, a pressurized and/or heated chamber, a volume of open air space, a chamber including a particular gas environment, etc.

The system 10 includes a source holding apparatus 30 for providing a first liquid spray composition to an inner opening 27 of the two concentric openings terminating at the dispensing end 23 of the nozzle structure 18 such as under control of control mechanism 55, e.g., hardware and/or software control, via feeder/flow control 24. The system 10 further includes a source holding apparatus 32 for providing a second liquid diluent composition to an outer opening 29 of the two concentric openings terminating at the dispensing end 23 of the nozzle structure 18 under control of control mechanism 55, e.g., hardware and/or software control, via feeder/flow control 25. An electrospray nozzle structure 18 can deliver a controlled feed rate of source material in the establishment of a spray of coating particles within the envelope of the nozzle structure. The nozzle structure 18 is configured to operate in a cone-jet mode as further described herein to provide a spray of coating particles 28 to the defined volume 17 where the object 15 is located using the source material (e.g., the first flow of liquid spray composition and the second flow of liquid diluent composition).

With further reference to FIG. 1, the nozzle structure 18 of the dispensing device 19 may include a nozzle structure having any one of various configurations and employing any number of different components, e.g., dual capillary electrodes, micro-machined tapered openings alone or in combination with capillary electrodes, etc. For example, as previously indicated, the nozzle structure may include one or more nozzle structures as described in U.S. Pat. No. 6,093,557 or U.S. Patent Application US-2002-0007869-A1. Various types of nozzle structures, and dispensing devices with which they may be used, are shown and described herein. However, nozzle structures described in documents incorporated herein may provide further nozzle structures that may be used according to the present invention and/or may provide additional description regarding the nozzle structures that have also been described generally herein.

The nozzle structure 18 of the electrospray dispensing device 19 provides a charged spray with a high concentration of charged particles. Generally, the concentration of charged particles in the spray is in the range of about $10^5$ particles per cubic centimeter (particles/cc) to about $10^{12}$ particles/cc. Due to the space charge effect, i.e., the effect created by the charge repulsion of charged particles, a spray of substantially dispersed particles having the same polarity charge is provided with the particles distributed substantially uniformly across a spray area.

As used herein, the term substantially dispersed particles refers to uniformly and/or nonuniformly sized particles separated by an applied repulsive electrostatic force. Thus, the electrospray process is a consistent and reproducible transfer process. Further, because the charged particles of the spray repel one another, agglomeration of the particles is avoided. This results in a more uniform particle size. "Substantially dispersed" particles are not to be confused with monodisperse particles which involves the general degree of uniformity of the particles sprayed, e.g., the standard deviation of the particles from a nominal size.

Generally, according to the configuration as shown at FIG. 1, the charge is applied by concentration of charge on the spray of coating particles through evaporation (at least partially) in an established electrical field 43 prior to the coating particles forming a selected coating 105 on the object 15. In other words, as further described herein the liquid sprayed generally evaporates to concentrate a charge of a liquid portion thereof on the coating particles, e.g., on the active ingredient of the particles. This results in the spray of charged coating particles 28 as described further herein.

FIG. 1 generally shows a diagrammatical illustration of the operation of the electrospray coating system 10 for establishing a charged spray 28 from the nozzle structure 18. The nozzle structure 18 receives a first flow of the liquid spray composition from the material source holding apparatus 30 and a second flow of the liquid diluent composition from the material source holding apparatus 32. For example, the material source holding apparatus 30 may include a liquid spray composition including drug active ingredients and a polymer at least partially dissolved in a solvent suitable to dissolve such a polymer therein. Further, for example, the material source holding apparatus 32 may include a liquid diluent composition including the same or a different solvent as the solvent in the liquid spray composition.

Generally, a conductive material 47, e.g., a conductive plate, positions the nozzle structure 18 in a particular configuration. For example, the conductive material 47 may be adapted to be connected to a high voltage source 20. The nozzle structure 18 includes a conductive structure, e.g., a capillary tube structure such as illustratively shown in FIGS. 7A and 7B, which defines orifices, e.g., openings 27 and 29, that terminate at the dispensing end 23 of the nozzle structure 18 for providing the flows of the liquid compositions.

Although various configurations for the source material holding apparatus 30 and 32 may be used according to the present invention, in one embodiment a single holding apparatus for each liquid composition is used to feed the respective liquid composition to the nozzle structure 18. One will recognize that any number of different and separate holding apparatus may be used or hold various different compositions and provide different compositions to one or more different nozzle structures (e.g., such as when multiple nozzle structures are used).

In one or more embodiments, the liquid spray composition and or liquid diluent composition may be pushed or pulled through the openings at the dispensing end 23 of the nozzle structure 18, e.g., pushed by a pump. In one embodiment, a compressed gas source, e.g., an inert source that is non-reactive with the composition, is provided to compress the composition and force fluid to flow through openings 27 and 29 of the nozzle structure 18. Although, in one embodiment, a compressed gas source may be used to provide such composition flow, other methods of providing such flow may also be used. For example, syringe pumps for each liquid composition may be used to establish the flow of material or the flow may also be controlled with use of a liquid pump (e.g., a syringe pump, a gravity feed pump, a pressure regulated liquid reservoir, etc.), a mass flow controller, or any other flow control devices suitable for feeding source material to the nozzle structure 18 as would be known to one skilled in the art.

The nozzle structure 18 positioned by and electrically coupled to the conductive structure 47 functions as a first electrode of the electrospray dispensing apparatus 19 with the dispensing end 23 of the nozzle structure 18 being positioned for dispensing charged microdroplets toward the object 15, or a surface 13 thereof. In the exemplary embodiment of FIG. 1, to set up the electric field 43, the object 15 may function as a second electrode structure, e.g., a grounded object 15 as shown by ground 81. An electrical potential difference is applied between the first electrode conductive structure 47 and the second electrode or grounded object 15 that is electrically isolated from the first electrode. One skilled in the art will recognize that the electrodes may be formed using one or more conductive elements, and such electrodes may take one of various different configurations. Further, the second electrode may also have a suitable opposite charge applied thereto (i.e., opposite to the first electrode).

Generally, in operation, a first flow of the liquid spray composition from the material source holding apparatus 30 and a second flow of the liquid diluent composition from the material source holding apparatus 32 is provided through the openings 27 and 29 of the nozzle structure 18, respectively. At least in one embodiment, a meniscus is formed at the dispensing end 23 where the inner opening 27 has an inner diameter in the range of about 6 microns to about 2 millimeters and an outer diameter in the range of about 8 microns to about 2.5 millimeters, and the outer opening 29 has an inner diameter in the range of about 15 microns to about 5 millimeters and an outer diameter in the range of about 30 microns to about 7 millimeters. Such dimensions are based on estimated clearances for different sizes of stainless steel capillaries and their wall thicknesses.

An electrical potential difference is applied to establish the nonuniform field 43 between the first electrode at the dispensing end 23 of the nozzle structure 18 and the second electrode (e.g., the grounded object 15). For example, a high positive voltage may be applied to the first electrode conductive structure 47 with the second electrode object 15 being grounded (e.g., the second electrode may also have a suitable opposite charge applied thereto; opposite to the first electrode. For example, a voltage difference that provides an electric field intensity greater than 4 kV/cm is used in order to provide cone-jet operation of the dispensing apparatus 19.

As used herein, nonuniform electric field refers to an electric field created by an electrical potential difference between two electrodes. The nonuniform electric field includes at least some electric field lines that are more locally concentrated at one electrode relative to the other electrode, e.g., more concentrated at the dispensing end 23 relative to the second electrode or a grounded object 15. In other words, for example, at least some of the field lines are off axis relative to the longitudinal axis 39 that extends through the center of the openings 27 and 29. For example, the grounded object 15 is positioned forward of dispensing end 23 and is of a size and/or includes at least a portion that is located at a position away from the longitudinal axis 39.

In various embodiments, the second electrode may also, or in the alternative, include one or more loop electrodes, plate electrodes, grounded surfaces, etc. The object 15 may still be coated even if a different electrode structure is used to produce the charged particles.

For example, a loop electrode 40 as shown in FIG. 1 may be positioned forward of the dispensing end 23 to create the electric field for providing highly charged particles in the defined volume 17 in which the object 15 is positioned. With the particles provided in the defined volume, the highly charged particles are moved toward a grounded object 15 as the loop electrode 40, at least in one embodiment is position in proximity to the surface of the object 15 to be coated. As such, it will be recognized that coating the object 15 using the electrospray coating system 10 shown generally in FIG. 1 may involve providing particles in a defined volume in which the object is provided, and thereafter, moving the particles toward the object forming a coating thereon. In addition, alternatively, the particles may be formed and moved toward the object for coating thereon simultaneously with their formation. For example, the object 15 may be grounded to set up the nonuniform electric field for producing the charged particles in the defined volume in which the object 15 is provided with the same field also providing for the movement of such charged particles towards the object 15 so as to form a coating thereon.

In one exemplary embodiment, where the liquid spray composition includes an active ingredient, the liquid spray composition is flowed through the inner opening 27 of the nozzle structure 18 and the liquid diluent composition is flowed through the outer opening 29 of the nozzle structure 18. Generally, the resulting blended flow of the liquid compositions at the dispensing end 23 has an electrical conductivity associated therewith. In other words, as the liquid compositions progress through the openings, the potential difference between the first and second electrodes, which creates the electric field there between, strips the liquid of one polarity of charge, i.e., the negative charge is stripped when a high positive voltage is applied to the first electrode, leaving a positively charged microdroplet to be dispensed from the dispensing end 23. For example, the meniscus at the dispensing end 23 may form a cone-jet for dispensing a spray of microdroplets including the active ingredients when forces of a nonuniform field balance the surface tension of the meniscus. The spray of microdroplets further becomes more positive in the nonuniform electric field.

As the microdroplets evaporate, the charge of the microdroplets concentrates on the active ingredients resulting in a spray of charged coating particles. The amount of charge on the microdroplet, and thus the amount of charge on a particle after evaporation, is based at least upon the conductivity of the fluid composition used to spray the microdroplet, the surface tension of the fluid composition, the dielectric constant of the fluid composition, and the feed flow rate thereof. At least in one embodiment, the electric charge concentrated on a particular particle is greater than about 30% of a maximum charge that can be held by the microdroplets, without the microdroplet being shattered or torn apart, i.e., greater than about 30% of the Rayleigh charge limit. At least in one another embodiment, the charge is greater than 50% of the Rayleigh charge limit. At 100%, the surface tension of the microdroplet is overcome by the electric forces causing droplet disintegration. The nonuniform electric field also provides for containment of particles and/or direction for the particles which would otherwise proceed in random directions due to the space charge effect.

One skilled in the art will recognize that the voltages applied may be reversed. For example, the first electrode may be grounded with a high positive voltage applied to the second electrode. In such a case, the particles would have a negative charge concentrated thereon. Further, any other applied voltage configuration providing a nonuniform electric field to establish the charged spray of coating particles may be used.

The nonuniform electric field can be provided by various configurations. For example, the second electrode may be any conductive material grounded (or having a suitable opposite charge applied thereto (i.e., opposite to the first electrode)) and positioned to establish the formation of a spray of coating particles 28 from the dispensing end 23 of the nozzle structure 18, e.g., the second electrode may be a grounded ring electrode, a grounded elongated element positioned in the interior volume of a stent structure, etc. The second electrode may also be located at various positions, such as just forward of the nozzle structure 18, or located farther away from the nozzle structure 18 and closer to object 15.

The strength of the field may be adjusted by adjustment of the distance between the first and second electrodes. Different field strengths may result in relatively different areas D upon which particle spray is provided, at least in part due to the space charge effect of the spray of particles 28. One skilled in the art will recognize that one or more components of the dispensing apparatus 19 may be moved relative to the others, e.g., the object 15 relative to the nozzle structure 18 or vice versa, to facilitate adjustment of field strength, and control one or more parameters according to the present invention to form a selected type of coating.

Further, the object 15 and/or the dispensing apparatus 19 (or any component thereof) may be moved in any one or more different directions as represented generally by the horizontal/vertical movement arrows 101 and radial movement arrow 102 prior to, during, or after the coating process for any particular reason. Such movement of the object 15 or any elements of the coating system 10 may be performed using any apparatus configured for the desired motion. The present invention is not limited to any particular structure for providing such movement. Further, the present invention is not limited to movement of any elements of the coating system 10 or the object 15 during the coating process. In other words, for example, the object 15, such as a medical device, may remain in a fixed position within the defined volume 17 as the coating process is performed.

The electrospray nozzle structure 18 used for particle generation as described herein is operable in a cone-jet mode when an appropriate voltage is applied for creation of the nonuniform electric field. For example, FIGS. 2A-2C are images of a capillary electrospray dispensing end (e.g., nozzle spray head) progressing from the start of spray (FIG. 2A) to a "pulsating" mode (FIG. 2B) to a "cone-jet" mode (FIG. 2C) according to the present invention.

FIG. 2B shows a magnified view of the dispensing end (e.g., capillary tip) operating in pulsating mode and the meniscus of fluid is clearly visible. In FIG. 2C, the dispensing end is operating in the cone-jet mode where the electric field forces the composition being sprayed into a sharp point from which a nanofibril can be seen emerging therefrom. This fibril is unstable and breaks up into charged particles according to the present invention (e.g., a solvent carrier and solute). The solvent evaporates due to the extremely high surface area. FIG. 2D shows a graph indicating the current versus voltage curve for electrospray of a particular solution. Note that a particular voltage is needed for the nozzle to operate in cone-jet mode and that such a voltage may need adjustment to maintain a stable cone-jet mode. A stable cone-jet mode of operation is of importance when applying a uniform selected type of coating to an object such as described herein.

As used herein, a stable cone-jet refers to a cone-jet that does not flutter between a cone-jet mode and a non-cone-jet mode (e.g., pulsating mode). Further, such a stable cone-jet may exhibit a dark tip appearance with no corona discharge being present.

As shown in FIG. 2C, a cone-jet 100 is formed at the dispensing end 23 of the nozzle structure 18. The cone-jet 100 extends from the dispensing end 23 to a point or tip 109, that, at least in one embodiment, lies on axis 39. An angle 104 is formed between the cone-jet 100 and a plane 106 lying orthogonal to axis 39 at the tip 109. When the angle 104 decreases such that it looks more like the meniscus of FIG. 2B, the cone-jet is more likely to move into a pulsating mode of operation. As such, by controlling the process to maintain a desired angle 104 of the cone-jet, a stable cone-jet can be achieved according to the present invention as further described herein.

As used herein, coating refers to forming a layer or structure on a surface. The coated layer or structure formed on the surface may be a coating that adheres to an underlying layer or the surface 13, or a coating that does not adhere to the surface or an underlying layer. Any level of adherence to the surface 13 or an underlying layer is contemplated according to the present invention. For example, a coating formed on surface 13 of the object 15 may be formed as a sheath about a structure (e.g., a stent structure) without necessarily having adhesion between the layer and the structure.

Likewise, an adhesion layer may be deposited on an object 15 prior to forming a coating on the object 15 such that greater adhesion is accomplished. The adhesion layer may also be coated on the surface 13 of the object 15 employing methods and/or systems according to the present invention.

Various embodiments of the coating methods and systems described are suitable to allow one or more objects to be coated as a batch. However, the present invention is not limited to only coating objects such as medical devices in batches, i.e., coating a group of one or more devices in one batch process followed by coating a second group of one or more devices in a second batch process. The methods and systems of the present invention can be utilized to continuously run objects through the systems such that the process does not have to be started and stopped for coating the objects in batches. In other words, a plurality of objects such as medical devices can be coated through a continuous process.

In one or more of the embodiments of the present invention, single or multiple coatings can be applied to objects, separately or simultaneously. For example, a coating sprayed may include multiple materials, different nozzle structures may be provided with different source materials for controlling and spraying different coating materials, different nozzle structures may be controlled for use during different time periods so as to provide different layers of coating materials on at least a portion of the object, multiple layers may be sprayed using the same or different source materials (e.g., forming a somewhat laminated coating), the entire object or just a portion of the object may be coated (e.g., a charge could be applied to a portion of the surface to attract all of or a majority of the sprayed particles to the charged portion), different portions of the object may be sprayed with a thicker coating than the remainder of the object, and/or masking materials may be used to mask certain portions of the object from having coating applied thereto.

As indicated above, the present invention contemplates applying one layer or multiple layers of the same or different types of coating (e.g., an open matrix coating, a closed film coating, and an intermediate matrix coating, in any combination). Such layers may perform identical or different functions (e.g., to provide for biocompatibility, to control drug release, etc.). Further, the one or more layers may be applied to conductive or non-conductive surfaces.

The object 15 may be a medical device amenable to the coating processes described herein. The medical device, or portion of the medical device, to be coated or surface modified may be made of metal, polymers, ceramics, composites or combinations thereof, and for example, may be coated with one or more of these materials. For example, glass, plastic or ceramic surfaces may be coated. Further, the present invention may be used to form a coating on surfaces of other objects as well, e.g., metal substrates or any other surfaces that may be rendered conductive (e.g., whether flat, curved, or of any other shape).

Although the coatings described herein may be used to coat a vascular stent, other medical devices within the scope of the present invention include any medical devices such as those, for example, which are used, at least in part, to penetrate and/or be positioned within the body of a patient, such as, but clearly not limited to, those devices that are implanted within the body of a patient by surgical procedures. Examples of such medical devices include implantable devices such as catheters, needle injection catheters, blood clot filters, vascular grafts, stent grafts, biliary stents, colonic stents, bronchial/pulmonary stents, esophageal stents, ureteral stents, aneurysm filling coils and other coiled devices, reconstructive implants, trans myocardial revascularization ("TMR") devices, percutaneous myocardial revascularization ("PMR") devices, lead wires, implantable spheres, pumps, dental implants, etc., as are known in the art, as well as devices such as hypodermic needles, soft tissue clips, holding devices, and other types of medically useful needles and closures. Any exposed surface of these medical devices may be coated with the methods and systems of the present invention.

The source material held in the source holding apparatus 30 may be any source of material (e.g., such as coating materials described herein including solvents and active ingredients) which can be provided in the defined volume in particle form as described according to the present invention. In one or more embodiments, the source material in source holding apparatus 30 is a liquid spray composition that may include a solution, a suspension, a microsuspension, an emulsion, a microemulsion, a gel, a hydrosol, or any other liquid compositions that when provided according to the present invention results in the generation of particles.

In one embodiment according to the present invention, the liquid spray composition may include at least one of a biologically active ingredient, a polymer, and a solvent (e.g., a solvent suitable to at least partially dissolve the polymer). Further, for example, such liquid spray compositions may include a biologically active ingredient, a polymer, and a solvent suitable to at least partially dissolve the polymer.

As used herein, an active ingredient refers to any component that provides a useful function when provided in particle form, particularly when provided as nanoparticles. The present invention is particularly beneficial for spraying nanoparticles and also is particularly beneficial for spraying particles including biologically active ingredients.

As such, the term "active ingredient" refers to material which is compatible with and has an effect on the substrate or body with which it is used, such as, for example, drug active ingredients, chemical elements for forming nanostructures, materials for modifying local cell adherence to a device, materials for modifying tissue response to a device surface, materials for modifying systemic response to a device, materials for improving biocompatibility, and elements for film coatings, e.g., polymers, excipients, etc.

The term "biologically active ingredient" or "biologically active material or component" is a subset of active ingredient and refers to material which is compatible with and has an effect (which may, for example, be biological, chemical, or biochemical) on the animal or plant with which it is used and includes, for example, medicants such as medicines, pharmaceutical medicines, and veterinary medicines, vaccines, genetic materials such as polynucleic acids, cellular components, and other therapeutic agents and drugs, such as those described herein.

As used herein, the term particle, and as such nanoparticle, includes solid, partially solid, and gel-like droplets and microcapsules which incorporate solid, partially solid, gel-like or liquid matter. Particles provided and employed herein may have a nominal diameter as large as 10 micrometers.

As used herein, nanoparticle refers to a particle having a nominal diameter of less than 2000 nm. The present invention is particularly beneficial in spraying nanoparticles having a nominal diameter greater than 1 nanometer (nm), particles having a nominal diameter less than 1000 nm, particles having a nominal diameter of less than 500 nm, particles having a nominal diameter of less than 200 nm, and particles having a nominal diameter of less than 100 nm.

Further, the particles used for coating as described herein are, in at least one embodiment, monodisperse coating particles. As used herein, monodisperse coating particles are coating particles that have a geometrical standard deviation of less than 1.2. In other words, the standard deviation with respect to mean particle size of particles provided according to the present invention is, at least in one embodiment, less than or equal to 20%.

The coating materials used in conjunction with the present invention are any desired, suitable substances such as defined above with regard to active ingredients and biologically active ingredients. In some embodiments, the coating materials comprise therapeutic agents, applied to medical devices alone or in combination with solvents in which the therapeutic agents are at least partially soluble or dispersible or emulsified, and/or in combination with polymeric materials as solutions, dispersions, suspensions, lattices, etc. The terms "therapeutic agents" and "drugs", which fall within the biologically active ingredients classification described herein, are used interchangeably and include pharmaceutically active compounds, nucleic acids with and without carrier vectors such as lipids, compacting agents (such as histones), virus, polymers, proteins, and the like, with or without targeting sequences. The coating on the medical devices may provide for controlled release, which includes long-term or sustained release, of a bioactive material.

Specific examples of therapeutic or biologically active ingredients used in conjunction with the present invention include, for example, pharmaceutically active compounds, proteins, oligonucleotides, ribozymes, anti-sense genes, DNA compacting agents, gene/vector systems (i.e., anything that allows for the uptake and expression of nucleic acids), nucleic acids (including, for example, recombinant nucleic acids; naked DNA, cDNA, RNA; genomic DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application. For example, biologically active solutes include anti-thrombogenic agents such as heparin, heparin derivatives, urokinase, and PPACK (dextrophenylalanine proline arginine chloromethylketone); prostaglandins, prostacyclins/prostacyclin analogs; antioxidants such as probucol and retinoic acid; angiogenic and anti-angiogenic agents; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine, lipoxygenase inhibitors; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, colchicine, epothilones, endostatin, angiostatin, Squalamine, and thymidine kinase inhibitors; L-arginine, its derivatives and salts (e.g., arginine hydrochloride); antimicrobials such as triclosan, cephalosporins, aminoglycosides, and nitorfuirantoin; anesthetic agents such as lidocaine, bupivacaine, and ropivacaine; nitric oxide (NO) donors such as lisidomine, molsidomine, NO-protein adducts, NO-polysaccharide adducts, polymeric or oligomeric NO adducts or chemical complexes; anticoagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; interleukins, interferons, and free radical scavengers; vascular cell growth promoters such as growth factors, growth factor receptor antagonists, transcriptional activators, and translational promoters; vascular cell growth inhibitors such as growth factor inhibitors (e.g., PDGF inhibitor—Trapidil), growth factor receptor antagonists, transcriptional repressors, translational repressors, replication inhibitors, inhibitory antibodies, antibodies directed against growth factors, bifinctional molecules consisting of a growth factor and a cytotoxin, bifinctional molecules consisting of an antibody and a cytotoxin; Tyrosine kinase inhibitors, chymase inhibitors, e.g., Tranilast, ACE inhibitors, e.g., Enalapril, MMP inhibitors (e.g., Ilomastat, Metastat), GP IIb/IIIa inhibitors (e.g., Intergrilin, abciximab), seratonin antagonist, and 5-HT uptake inhibitors; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof; and beta blockers. In one or more embodiments, these and other components may be added to a liquid spray composition that includes a polymer and a solvent suitable for dissolving all or at least a part of the polymer in the composition.

Modifications to or various forms of the coating materials and/or additional coating materials for use in coating a medical device according to the present invention are contemplated herein as would be apparent to one skilled in the art. For example, such coating materials may be provided in derivatized form or as salts of compounds.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include, as a primary example, those proteins or polypeptides that can compensate for defective or deficient species in an animal, or those that act through toxic effects to limit or remove harmful cells from the body. In addition, the polypeptides or proteins that can be incorporated into the polymer coating, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Coating materials other than therapeutic agents include, for example, polymeric materials, sugars, waxes, and fats, applied alone or in combination with therapeutic agents, and monomers that are cross-linked or polymerized. Such coating materials are applied in the form of, for example, powders, solutions, dispersions, suspensions, and/or emulsions of one or more polymers, optionally in aqueous and/or organic solvents and combinations thereof or optionally as liquid melts including no solvents.

When used with therapeutic agents, the polymeric materials are optionally applied simultaneously with, or in sequence to (either before or after), the therapeutic agents. Such polymeric materials employed as, for example, primer layers for enhancing subsequent coating applications (e.g., application of alkanethiols or sulfhydryl-group containing coating solutions to gold-plated devices to enhance adhesion of subsequent layers), layers to control the release of therapeutic agents (e.g., barrier diffusion polymers to sustain the release of therapeutic agents, such as hydrophobic polymers; thermal responsive polymers; pH-responsive polymers such as cellulose acetate phthalate or acrylate-based polymers, hydroxypropyl methylcellulose phthalate, and polyvinyl acetate phthalate), protective layers for underlying drug layers (e.g., impermeable sealant polymers such as ethylcellulose), biodegradable layers, biocompatible layers (e.g., layers comprising albumin or heparin as blood compatible biopolymers, with or without other hydrophilic biocompatible materials of synthetic or natural origin such as dextrans, cyclodextrins, polyethylene oxide, and polyvinyl pyrrolidone), layers to facilitate device delivery (e.g., hydrophobic polymers, such as an arborescent polyisobutylene copolymer, or hydrophilic polymers, such as polyvinyl pyrrolidone, polyvinyl alcohol, polyalkylene glycol (i.e., for example, polyethylene glycol), or acrylate-based polymer/copolymer compositions to provide lubricious hydrophilic surfaces), drug matrix layers (i.e., layers that adhere to the medical device and have therapeutic agent incorporated therein or thereon for subsequent release into the body), and epoxies.

When used as a drug matrix layer for localized drug delivery, the polymer component of the coatings may include any material capable of absorbing, adsorbing, entrapping, or otherwise holding the therapeutic agent to be delivered. The material is, for example, hydrophilic, hydrophobic, and/or biodegradable, and is preferably selected from the group consisting of polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyurethanes, silicones, polyurea, polyacrylate, polyacrylic acid and copolymers, polyorthoesters, polyanhydrides such as maleic anhydride, polycarbonates, polyethylene, polypropylenes, polylatic acids, polystyrene, natural and synthetic rubbers and elastomers such as polyisobutylene (PIB), polyisoprene, polybutadiene, including elastomeric copolymers, such as Kraton®, styrene-isobutylene-styrene (SIBS) copolymers; polyglycolic acids, polycaprolactones, polyhydroxybutyrate valerates, polyacrylamides, polyethers, polysaccharides such as cellulose, starch, dextran and alginates; polypeptides and proteins including gelatin, collagen, albumin, fibrin; copolymers of vinyl monomers such as ethylene vinyl acetate (EVA), polyvinyl ethers, polyvinyl aromatics; other materials such as cyclodextrins, hyaluronic acid and phosphoryl-cholines; and mixtures and copolymers thereof. Coatings from polymer dispersions such as polyurethane dispersions (BAYHDROL, etc.) and acrylic latex dispersions are also within the scope of the present invention. Preferred polymers include polyurethanes; polyacrylic acid as described in U.S. Pat. No. 5,091,205; and aqueous coating compositions comprising an aqueous dispersion or emulsion of a polymer having organic acid functional groups and a poly-functional crosslinking agent having functional groups capable of reacting with organic acid groups, as described in U.S. Pat. No. 5,702,754. Other polymers that may be used include poly(DL-lactide-co-ε-caprolactone, 80/20) (PLCL), Chronoflex AR (CFR) which is polyurethane 22% solid in dimethylacetamide, and poly(tetrahydrofurfuryl methacrylate-co-ethyl methacrylate) PTHFMA-EM.

One or more solvents may be used as part of the liquid spray composition to fully or partially dissolve one or more polymers thereof. Such solvents may range from polar solvents (e.g., acetone and methanol) to non-polar solvents (e.g., tetrahydrofuran and toluene).

Polar solvents, as used herein, are liquids that tend to have higher dielectric constants, where the higher the dielectric constant, the greater the relative polarity. Such polar solvents may include, for example, but are not limited to, water, methanol, ethanol, isopropanol, acetonitrile, acetone, and tetrahydrofuran.

Non-polar solvents, as used herein, are liquids that tend to have lower dielectric constants than polar solvents, where the lower the dielectric constant, the lower the relative polarity. Such non-polar solvents may include, for example, but are clearly not limited to, toluene, chloroform, hexane, and dichloromethane.

In one or more embodiments herein, particularly where an open matrix coating is desired, high dielectric constant solvents may be used. Such high dielectric constant solvents include solvents having a dielectric constant equal to or greater than 10. For example, high dielectric constant solvents include water (dielectric constant of 80), methanol (dielectric constant of 33), ethanol (dielectric constant of 24), or acetone (dielectric constant of 21).

In one or more other embodiments, low dielectric constant solvents may be used. Such low dielectric constant solvents include solvents having a dielectric constant less than 10. One will recognize that some polar solvents, such as tetrahydrofuran, are low dielectric constant solvents even though they are polar solvents. For example, low dielectric constant solvents include tetrahydrofuran (dielectric constant of 7.5), chloroform (dielectric constant of 4.8), or toluene (dielectric constant of 2.4).

The release rate of drugs from drug matrix layers is largely controlled, for example, by variations in the polymer structure and formulation, the diffusion coefficient of the matrix, the solvent composition, the ratio of drug to polymer, potential chemical reactions and interactions between drug and polymer, the thickness of the drug adhesion layers and any barrier layers, and the process parameters, e.g., drying, etc. The coating(s) applied by the methods and apparatuses of the present invention may allow for a controlled release rate of a coating substance with the controlled release rate including both long-term and/or sustained release.

The source material held in the source holding apparatus 32 may be any liquid diluent composition which when provided in combination with the liquid spray composition at the dispensing end 23 of the nozzle structure results in coating particles being provided in the defined volume in particle form as described according to the present invention herein. The source material in source holding apparatus 32 is a liquid diluent composition that includes at least one of a polar or non-polar solvent as described herein.

At least in one embodiment, the liquid diluent composition includes one or more high dielectric constant solvents. Further, at least in one embodiment, the liquid diluent composition has a high dielectric constant (i.e., a dielectric constant that is equal to or greater than 10). For example, the liquid diluent composition may include a high dielectric constant solvent and include a low dielectric constant solvent (e.g., mixed solvents), yet still the liquid diluent composition may have a high dielectric constant.

Further, when the liquid diluent composition has a high dielectric constant, the liquid diluent composition may further include an active ingredient, such as a polymer or a drug. Further, at least in another embodiment, the liquid diluent composition is a high dielectric constant composition and includes a biologically active ingredient (i.e., without a polymer).

Further, at least in one embodiment, the liquid diluent composition has a weight concentration of active ingredient that is less than 1 percent of the total weight concentration of the liquid diluent composition (e.g., a biologically active ingredient that is less than 1 percent of total weight concentration). Further, in another embodiment, the liquid diluent composition has a weight concentration of active ingredient that is less than 0.5 percent of the total weight concentration of the liquid diluent composition.

Still further, in one embodiment, the liquid diluent composition may further include an additive that is used to control conductivity of the liquid diluent composition. For example, the additive used to control conductivity may include a buffer solution such as a phosphate buffer (e.g., for spraying particles including peptides), an acid such as nitric acid, or a salt such as ammonium chloride. Generally, with use of a low dielectric constant solvent, an additive to increase the conductivity of the liquid diluent composition is needed to apply an open matrix coating.

Still further, at least in one embodiment, the liquid diluent composition includes only solvents and has a high dielectric constant (e.g., includes at least one high dielectric constant solvent. With use of only solvents in the liquid diluent composition, fouling of the spray tip is less likely.

The coatings of the present invention are applied such that they result in a suitable thickness, depending on the coating material and the purpose for which the coating or coatings are applied. For example, coatings applied for localized drug delivery are typically applied to a thickness of at least about 1 micron and not greater than 30 microns. In one embodiment, the thickness is greater than 2 microns. Further, in another embodiment, the thickness is not greater than 20 microns. In addition, very thin coatings such as those as thin as 100 Angstroms may be provided. Much thicker coatings of more than 30 microns are also possible.

Several detailed configurations for the dispensing device 19 are described in further detail herein. For example, FIG. 7A is a more detailed diagram of one configuration of a portion 300 of an electrospraying apparatus such as shown generally in FIG. 1 including a dual concentric opening dispensing device 314 extending along axis 301 according to the present invention from a first end 304 to a second end or dispensing end 380. First end 304 may be formed of conductive portions to facilitate application of voltages or ground to capillary tube 320.

The first end 304 includes a distributor head 316 that is coincident with axis 301 for use in establishing the spray of particles. The distributor head 316 includes capillary tube 320 having an axis therethrough coincident with axis 301. The capillary tube 320 includes a first end 330 sealingly positioned in aperture 385 of the first end 304 by conductive sealing element 337 at the upper surface 383 of the first end 304. The capillary tube 320 further includes a second end 332 positioned for providing a liquid spray composition to the dispensing end 380 (i.e., through an inner opening 391 that terminates at the dispensing end 380 for use in generating the spray of particles as desired). The capillary tube 320 may be made of any suitable material, such as, for example, platinum, silica, stainless steel, etc. and may be of any suitable size. For example, the capillary tube may, at least in one embodiment, have an outer diameter in the range of about 8 μm to about 2.5 mm, and an inner diameter in the range of about 6 μm to about 2 mm. Further, in another embodiment, the inner diameter of the capillary tube is in the range of about 10 μm to about 200 μm.

Further, the distributor head 316 includes a nozzle portion or casing 322 which as illustrated in FIG. 7A is an elongate substantially cylindrical metal casing concentric with the capillary tube 320 for providing an outer opening 392 concentric with inner opening 390 for providing liquid diluent compositions to the dispensing end 380. However, the casing 322 can be conductive or nonconductive. Together, in this particular embodiment, the capillary tube 320 and the casing 322 form the dual opening capillary tube electrode of the distributor head 316 for use in providing the spray of particles when operating in a cone-jet mode. The casing or nozzle portion 322 includes a first end portion 336 which tapers at section 335 thereof to a narrower second end portion 338. The second end portion 338 extends from the tapered section 335 and is concentric with the second end 332 of the capillary tube 320. The narrow end of the tapered section 335 extends a distance of about 5 mm to about 5 cm from the lower surface 385 of the first end 304. The outer diameter of the second end portion 338 is in the range of about 2 mm to about 5 mm and the inner diameter of the second end portion 338 is in the range of about 0.1 cm to about 0.2 cm. The second end 332 of the capillary tube 320 extends beyond the second end portion of the metal casing or nozzle portion 322 towards the target surface to be coated by a distance of about 2 mm to about 5 mm. The nozzle portion 322 is formed of any suitable metal or nonconductive material such as stainless steel, brass, alumina, or any other suitable material. The nozzle portion 322 is spaced from the capillary tube 320 by spacers 326 or other spacing structures. For example, a metal casing 322 may be deformed at particular portions, such as pin points or depressions, to create a neck for centering the capillary tube 320 therein. An inlet 348 is configured for directing the liquid diluent composition 349 in aperture or opening 392 between the concentric capillary tube 320 and the nozzle portion 322. One will recognize the capillary tube electrode may take one of many configurations.

A gas inlet 354 is provided in the first end 304 to allow for input of a stream of electro-negative gases, e.g., $CO_2$, $SF_6$, etc., to form a gas sheath about the capillary tube 320 or flood the region about dispensing end 380. This gas sheath allows the applied voltage to be raised to higher levels without corona discharge, e.g., the electrostatic breakdown voltage for the capillary tube electrode is increased. The entire portion of end 304 or portions thereof may be formed of conductive materials to facilitate application of a voltage or ground to the capillary tube electrode. For example, sealing elements 337 may be nonconductive, but in one embodiment are conductive to facilitate application of a voltage or ground to capillary tube 320. Further, in one or more embodiments, generally, the region around the capillary tube 320 and the nozzle portion 322 is flooded with a gas through the port 354 to increase the electrostatic breakdown voltage for the capillary tube electrode. In one embodiment, a chamber in which the coating process is being completed is flooded with the gas through the port 354 and then a flow in the range of about 5 cc/min to about 200 cc/min is continued through the port 354.

To establish the spray of particles from the dual opening dispensing device 314, a first flow of a liquid spray composition is received in the first end 330 of the capillary tube 320 and flows through opening 391. For example, the flow rate of the liquid spray composition may be greater than about 0.01 μl/min or less than about 10 μl/min; or further may be less than about 5 μl/min, or even less than about 3 μl/min. Further, a second flow of a liquid diluent composition 349 is received in the port 348 of the nozzle and provided to opening 392. For example, the flow rate of the liquid diluent composition may be greater than about 0.01 μl/min or less than about 10 μl/min; or further may be less than about 5 μl/min.

In one embodiment, a relatively high voltage, for example, in the range of about 2000 volts to about 6000 volts, may be applied between the object being coated and the capillary tube 320 to establish the potential difference between the first and second electrode of the spraying apparatus and cause operation in cone-jet mode. In this particular illustrative configuration, capillary tube 320, metal casing 322, and sealing element 337 are conductive. Spray 328 is established forward of the dispensing tip 380 of the second end 332 of the capillary tube 320 per a mode of operation as previously described. The potential difference between the electrodes establishes an electric field there between, causing operation in a cone-jet mode for generation of coating particles according to the present invention.

The electrospray coating system 10 illustrated and described generally herein with reference to FIG. 1 can be controlled to provide for particular types of selected coatings according to the present invention. For example, one or more different parameters of the system 10 may be controlled so as to form an open matrix coating as opposed to a closed film coating.

According to one or more embodiments of the present invention, the coating process using one or more controlled parameters as described herein allows for applying nanocomposite coatings onto objects such as coronary stents and/or other medical devices. The cone-jet mode of operation produces highly charged, uniform, monodisperse nanoparticles comprised of one or more components that are used to coat the object. Non-line-of-sight coating can be achieved (i.e., coating of surfaces not directly in the line of sight of the dispensing end 23, such as the interior surface of a stent). The coating particles in such non-line-of-sight coating are directed to the surface of the object being coated by the established electrical field, which aids in the uniform coating of objects with intricate architecture. Use of the dual opening nozzle structure (e.g., a dual-capillary spray head) permits two liquid streams of materials to be mixed at the spray tip or dispensing end 23, which enables the application of multiple agents in a nanocomposite open matrix coating and the co-spraying of materials which are otherwise incompatible. The electrospray process can accommodate a range of polymers and solvents that are used or likely to be used in coating objects such as stents.

In at least one embodiment, solvents required to dissolve a polymer (e.g., poly(isobutylene), poly(styrene-b-isobutylene-b-styrene, etc.) to be sprayed are low dielectric constant non-polar solvents (e.g., toluene) or are low dielectric constant polar solvents (tetrahydrofuran) and not easily amenable to electrospray. However, using the following techniques including, for example, adding a higher dielectric constant solvent such as methanol in the inner or in the outer capillary liquid stream, as further described herein, a liquid spray composition that includes such a hard to spray dissolved polymer can be used to coat an object.

Generally, one or more control parameters may be useful in selecting a type of coating to be formed on the object 15. Such control parameters which shall be discussed in further detail herein include controlling a flow rate of the second flow of the liquid diluent composition in the outer opening 29 relative to a flow rate of the first flow of the liquid spray composition in the inner opening 27 (e.g., controlling the ratio of the flow of the liquid diluent composition to the total flow of the liquid spray composition and liquid diluent composition dispensed at the dispensing end 23), selecting a particular liquid diluent composition to be provided in the outer opening 29 (e.g., selecting a particular liquid diluent composition having a particular conductivity); and controlling the evaporation process of the microdroplets dispensed from the dispensing end 23 of the nozzle structure 18.

The relative flow rate of the second flow of the liquid diluent composition in the outer opening 29 to the flow rate of the first flow of the liquid spray composition in inner opening 27 can be selected to achieve a desired coating described herein. For example, selection of a higher ratio of flow rate for the liquid diluent composition relative to the total flow rate of the liquid spray composition and liquid diluent composition dispensed at the dispensing end 23, may result in the formation of a closed film coating.

As would be recognized, the ratio necessary to achieve a desired selected coating may depend on the compositions being used. However, generally, according to the present invention as the flow rate of the liquid diluent composition in the outer opening 29 exceeds 5 times the flow rate of the liquid spray composition in the inner opening 17, a closed film coating occurs. In other words, as the ratio of flow rate for the liquid diluent composition at the outer opening 29 relative to the total flow rate of the liquid spray composition and liquid diluent composition dispensed at the dispensing end 23 gets closer to 1, a closed film coating is achieved. As such, a user with the desired compositions known, can adjust the flow rates to achieve a selected type of coating by controlling the flow rate of the second flow of the liquid diluent composition in the outer opening 29 relative to the flow rate of the first flow of the liquid spray composition in inner opening 27.

Selecting a particular liquid diluent composition to be provided in the outer opening 29 can also be used to achieve a desired coating described herein. For example, selecting a liquid diluent composition that includes one or more high dielectric constant solvents (e.g., such as a liquid diluent composition that includes at least one of acetone or methanol (both higher dielectric constant solvents)) such that the liquid diluent composition has a high dielectric constant is likely to result in an open matrix coating. Likewise, selecting a liquid diluent composition that includes one or more low dielectric constant solvents (e.g., such as a liquid diluent composition that includes at least one of chloroform, toluene, or tetrahydrofuran (all low dielectric constant solvents)) such that the liquid diluent composition has a low dielectric constant is likely to result in a closed film coating.

In other words, selecting a liquid diluent composition for the outer opening that has a certain dielectric constant can be used to achieve a particular selected coating. For example, liquid diluent compositions that have a high dielectric constant (i.e., greater than 10) are typically required to obtain an open matrix coating.

Yet further, at least in one embodiment, selecting a particular high dielectric constant solvent for use in the liquid spray composition to be provided in the inner opening 27 may also be used to achieve a desired coating described herein. For example, selecting a solvent for use in the liquid spray composition that includes one or more high dielectric constant solvents (e.g., such as a liquid diluent composition that includes at least one of acetone or methanol (both higher dielectric constant solvents)) may be beneficial in providing an open matrix coating. For example, such a high dielectric constant solvent may be added to a low dielectric constant solvent that is required to dissolve a particular polymer to provide the ability to apply an open matrix coating (e.g., making the dielectric constant of the liquid spray composition higher).

Yet further, increasing the conductivity of the second flow of the liquid diluent composition is useful for achieving an open matrix coating on the at least one surface of the object 15. Such conductivity may be achieved by selecting, at least in one embodiment, a liquid diluent composition that has a conductivity greater than 1 $\mu$S cm$^{-1}$ (microSiemen/cm). In another embodiment, a liquid diluent composition that has a conductivity greater than 6.8 $\mu$S cm$^{-1}$ is beneficial in forming an open matrix coating.

Use of a liquid diluent composition that has a conductivity greater than 1 $\mu$S cm$^{-1}$, or even greater than 6.8 $\mu$S cm$^1$, provides for substantially round particles being formed in the open matrix coating. Such substantially round particles are shown in FIG. 10, images c,d,g,h, as opposed to elongated fiber particles shown in FIG. 10, images a,b,e,f. The substantially round particles are a direct result of using a high conductivity liquid diluent composition in the outer opening.

The conductivity of the liquid diluent composition can be manipulated using any known techniques. The liquid diluent composition may include a single component having a relatively high conductivity or a relatively high conductivity component may be added to a relatively low conductivity component. For example, an acid (e.g., nitric acid) or a salt (e g, ammonium chloride) may be used to increase the conductivity of certain types of solvents (e.g., acetone, methanol, or water) that are desired for use as part of the liquid diluent composition.

At least in one embodiment, a lower conductivity liquid spray composition is provided at the inner opening 27. For example, the conductivity of the liquid spray composition (e.g., including de-ionized water and toluene) may be in the range of about 0.3 $\mu$S cm$^{-1}$ to about 1.0 $\mu$S cm$^{-1}$. In such a case, a liquid diluent composition (e.g., such as that including nitric acid) having a conductivity in the range of about 100 $\mu$S cm$^{-1}$ to about 1000 $\mu$S cm$^{-1}$ may be necessary to facilitate breakup of the inner stream of liquid spray composition so as to spray the coating particles.

At least in one embodiment, the liquid spray composition includes at least a biologically active material and a polymer. For example, in one or more embodiments, the ratio of weight concentrations of polymer to biologically active material (e.g., polymer:dexamethasone) may be as high as 10:1 or as low as 5:1. However, even lower ratios may be sprayed. Further, in one or more other embodiments of the liquid spray composition, the weight concentration of the active ingredient (e.g., the polymer or the polymer and biologically active ingredient) may be less than 5 percent of the total weight of the liquid spray composition, and may be less than 1 percent of the total weight concentration of the liquid spray concentration.

Further, the evaporation process of the microdroplets dispensed from the dispensing end 23 of the nozzle structure 18 may be controlled to achieve a particular selected coating. For example, the time allowed for evaporation of the microdroplets may be controlled as a function of selected type of coating to be applied.

Figure 4:
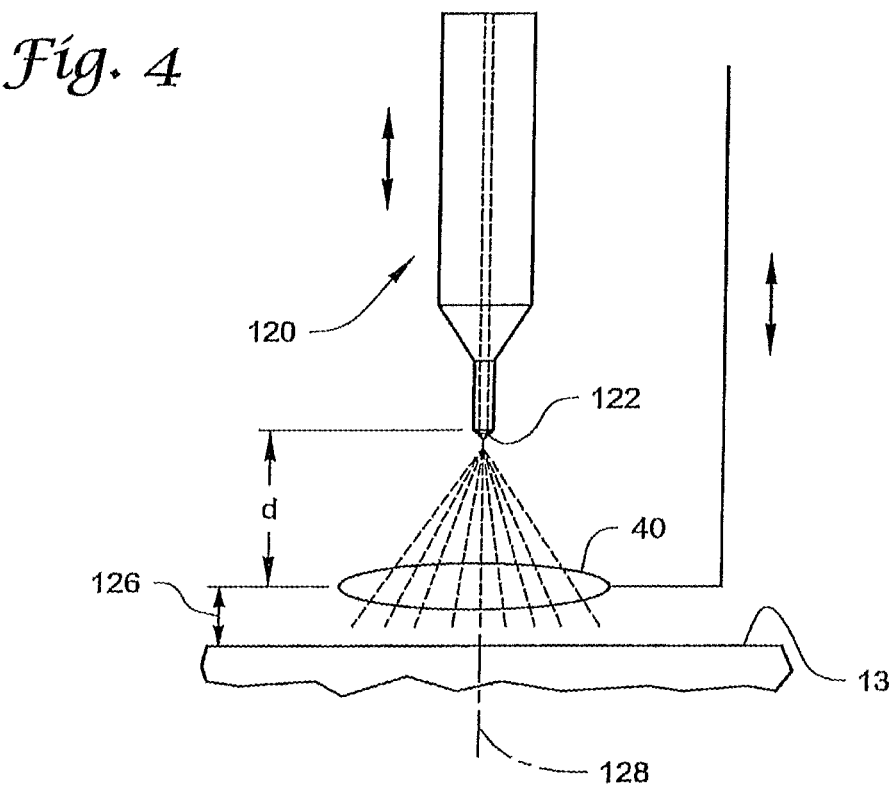
FIG. 4 shows a general diagrammatical illustration of one embodiment of an electrospray dispensing device including a ring electrode for controlling particle spread as well as for illustrating control of nozzle to target surface distance for applying one or more of the types of coatings such as generally shown in FIGS. 3A-3C.

In one embodiment, the time allowed for evaporation of the microdroplets before they reach the object 15 to form a coating thereon is increased so that an open matrix coating can be formed. For example, as shown in FIG. 4, a dual opening nozzle structure 120 is shown that has a dispensing end 122. The distance between the dispensing end 122 of the nozzle structure 120 and the surface 13 of the object 15 to be coated is controlled depending on the selected type of coating to be applied. For example, the distance d between the dispensing end 122 of the nozzle structure 120 and the surface 13 of the object 15 may be increased upon selection of an open matrix coating to allow more time of flight for evaporation of the microdroplets or decreased upon selection of a closed film coating to allow less time for evaporation. As would be recognize, either the nozzle structure 120 or the object 15 may be moved to adjust the distance d.

As described above, as the microdroplets evaporate, the charge of the microdroplets concentrates on the active ingredients resulting in a spray of charged particles. In one embodiment, the coating system 10 is configured such that prior to contact with the at least one surface 13 of the object 15, the weight percent of solvent in the evaporated microdroplet is less than 85% (e.g., corresponding to a weight percent of 15% polymer in a droplet that only includes only polymer solids and the solvent). At least in one embodiment, some solvent component forms a part of the particle volume as the particle contacts the surface 13 of the object 15. With some solvent component being a part of the residual particle volume occupied by the evaporated microdroplet, adhesion of the microdroplet (including the particle) to the surface 13 of the object 15 may be enhanced. After the microdroplet has contacted the surface 13 of the object 15, the remainder portion of the solvent evaporates, leaving the particle coated on the surface 13 of the object 15.

Generally, at least in one embodiment, an open matrix coating is facilitated by solvent evaporation such that the residual solvent immediately prior to contact with the at least one surface 13 of the object 15 is less than 85% by weight of the evaporated microdroplet. However, the relative composition of solvent:polymer in the particle that promotes open matrix formation may be different depending on the polymer used. But, generally, at least in one embodiment, an open matrix coating would be facilitated by solvent evaporation such that the residual solvent prior to contact with the at least one surface 13 of the object 15 is less than 80% by weight of the evaporated microdroplet. Likewise, generally, at least in one embodiment, a closed film coating would be facilitated by solvent evaporation such that the residual solvent immediately prior to contact with the at least one surface 13 of the object 15 is more than 90% by weight of the evaporated microdroplet. It will be apparent to one skilled in the art that the relative percentages of solvent and polymer that are given may vary according to the characteristics of the specific polymer that is used.

The amount of evaporation prior to the microdroplet/particle contacting the surface 13 of the object 15 may be controlled in a number of different ways for applying one or more different selected types of coatings, in addition to selecting a distance d as shown in FIG. 4. For example, the evaporation may be controlled by the type of solvent used, the temperature and pressure of a chamber in which the medical device is provided, the size of the microdroplet, the humidity, etc.

For example, maintaining a temperature in the defined volume in the range of 20 degrees centigrade to 30 degrees centigrade may be necessary upon selection of an open matrix coating. The temperature typically should not exceed the glass transition temperature for a given polymer.

Further, in one embodiment, maintaining humidity in the defined volume 17 to less than 20 percent RH assists in maintaining stability of the coating process. Controlling relative humidity prevents arcing or corona discharge. If the relative humidity is kept lower, higher voltages can be used before corona discharge becomes a problem, facilitating the cone-jet formation and maintenance.

Figure 5:
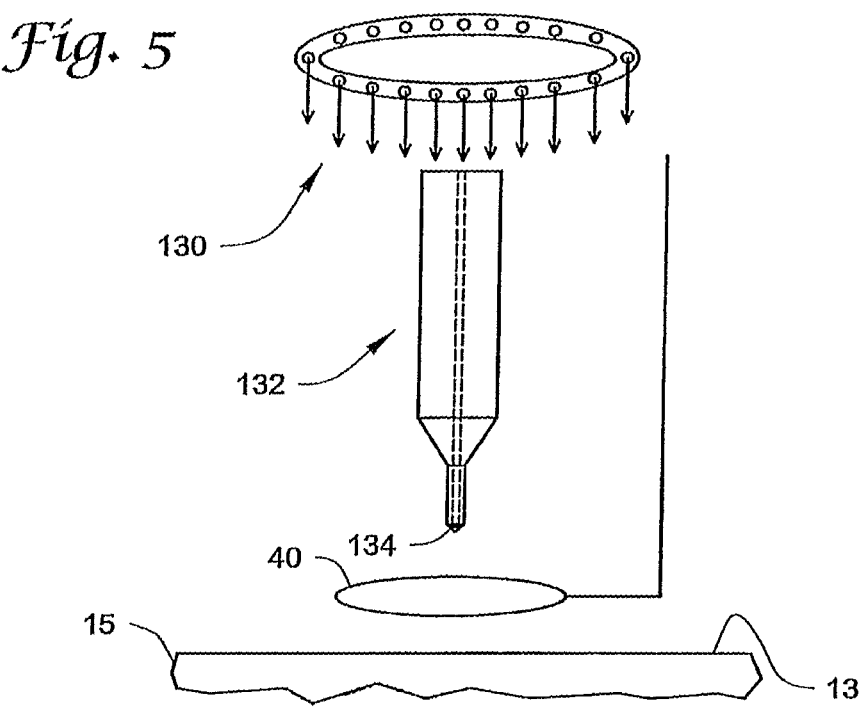
FIG. 5 shows a general diagrammatical illustration of one embodiment of an electrospray dispensing device including a ring electrode for controlling particle spread as well as a gas flow for use in controlling the application of one or more of the types of coatings such as generally shown in FIGS. 3A-3C.

As shown in FIG. 5, evaporation may also be controlled by providing a gas stream 130 in proximity to the cone-jet formed at the dispensing end 134 of a nozzle structure 132. As stream of gas along side the nozzle structure 132 may be provided, or the defined volume may be flooded with a gas. For example, one or more gases such as nitrogen or carbon dioxide may be used to increase evaporation. As such, with increased evaporation, achieving an open matrix coating is more likely. Yet further, providing the gas stream may assist in keeping the cone-jet stable (e.g., provide anti-fouling of the dispensing end 23). Still further, the gas stream should not generate turbulence around the cone jet, as this could cause instability thereof.

As previously mentioned, as the microdroplets evaporate and charge is concentrated on the particles, the nonuniform electric field provides for containment of particles and/or direction for the particles which would otherwise proceed in random directions due to the space charge effect; the space charge effect being necessary to provision of monodisperse and nonconglomerated particles. The space charge effect is generally dependent upon the size of the particles and the charge thereon. With the electric field being utilized to move the particles towards the object 15 and preventing them from scattering to other locations, the amount of coating material necessary to coat the object 15 is substantially reduced.

The loop electrode 40 as shown in FIG. 4 can also be used to prevent scattering and decrease the amount of coating material necessary to coat the object 15. For example, the loop electrode 40 can be used to establish the nonuniform electric field when positioned along a plane generally orthogonal to an axis 128 along which the nozzle structure 120 extends. The position, size and shape of the loop can be used to control the direction of the coating particles so as to coat the desired surfaces of the object 15. Generally, the loop 40 may be provided at a distance 126 that is about 1 mm from the target object 15 or may be further away from the target object. For example, the loop may be as far from the target as possible but still capable of generating the desired non-uniform electric field. For example, the loop 40 may lie in approximately the same plane as the tip of the nozzle structure (e.g., orthogonal to the axis along which the nozzle structure extends).

Yet further, one or more process techniques may be implemented to maintain a stable cone-jet during operation of the coating process so as to achieve the selected type of coating. For example, such techniques may include adjusting the voltage between the dispensing end of the nozzle structure 18 and the object 15 being coated as the thickness of the selected type of coating increases so as to maintain a stable cone-jet at the dispensing end 23 of the nozzle structure 18 and/or monitoring at least one characteristic associated with the cone-jet to determine the stability of the cone-jet based thereon, and thereafter adjusting one or more process parameters to maintain a stable cone-jet.

When the thickness of the selected type of coating 105 increases on the object 15, the cone-jet may become unstable. For example, as the coating thickness increases, the electrical potential between the first and second electrode of the system 10 may no longer be sufficient to continue cone-jet mode operation. As such, adjusting the voltage between the dispensing end 23 of nozzle structure 18 and the object 15 being coated may be needed to maintain a stable cone-jet at the dispensing end of the nozzle structure 18. The adjustment of the voltage may be done manually by a user or may be performed automatically as a function of one or more characteristics of the cone jet as described further herein.

For example, as illustratively shown in FIG. 1, a detection apparatus 50 (e.g., an imaging apparatus) may be used to detect at least one characteristic associated with the cone-jet (e.g., shift in angle 104 as shown in FIG. 2C). The stability of the cone-jet may then be determined based on the at least one characteristic and one or more process parameters may be adjusted accordingly to maintain a stable cone-jet. In other words, at least in one embodiment, an imaging apparatus may be used to detect the angle 104 as shown in FIG. 2C associated with the cone-jet. Depending on the desired angle 104 for maintaining stability, control apparatus 55 may determine that the cone-jet is on the verge of instability (e.g., due to increased thickness of the coating 105 being formed on the object 15). Upon such a determination, the electrical potential between the dispensing end 23 and the object 15 may be increased to maintain stable cone-jet operation.

Yet further, other characteristics associated with the cone-jet may be monitored. For example, the detection apparatus 50 may detect one or more flutters in the cone-jet (e.g., the cone-jet going into pulsating mode temporarily from cone-jet mode). Further, the detection apparatus may use imaging of the cone-jet to detect bubbles in at least one of the liquid flows being provided thereto. If bubbles are detected or flutters are detected, one or more various actions may be taken. For example, the flow of liquid to the nozzle may be modified, the flow may be interrupted to prevent sputtering on the surface of the target, and/or the voltage may be adjusted to eliminate the instability of the cone-jet.

Figure 6:
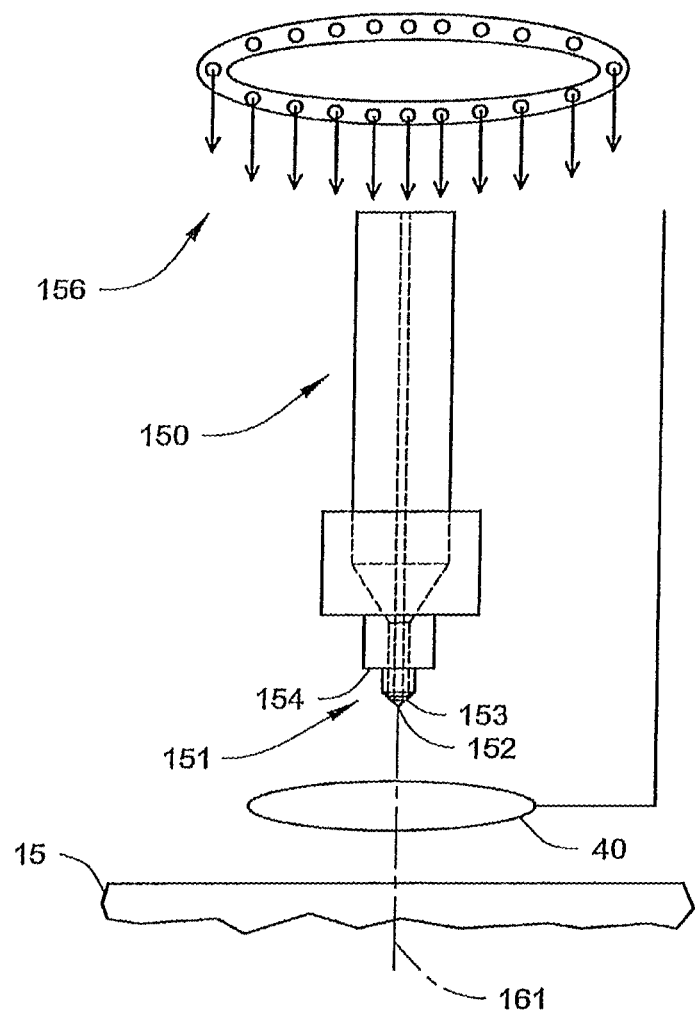
FIG. 6 shows a general diagrammatical illustration of one embodiment of an electrospray dispensing device that includes a triple opening nozzle in accordance with the present invention, and further includes a ring electrode for controlling particle spread as well as a gas flow for use in controlling the application of one or more of the types of coatings such as generally shown in FIGS. 3A-3C.

One will recognize that more than two concentric openings may be provided which terminate at the dispensing end 23 of the nozzle structure 18 (e.g., to provide more than two flows of compositions at the dispensing end). For example, although any suitable number of openings may be used, FIG. 6 shows a nozzle structure 150 that includes three concentric openings that terminate at the dispensing end 151 and which lie along axis 161. One will recognize that the termination of such openings can be displaced from one another along the axis 161 but must be in close proximity to allow the cone-jet to form from all compositions provided at the termination of such openings.

Figure 8:
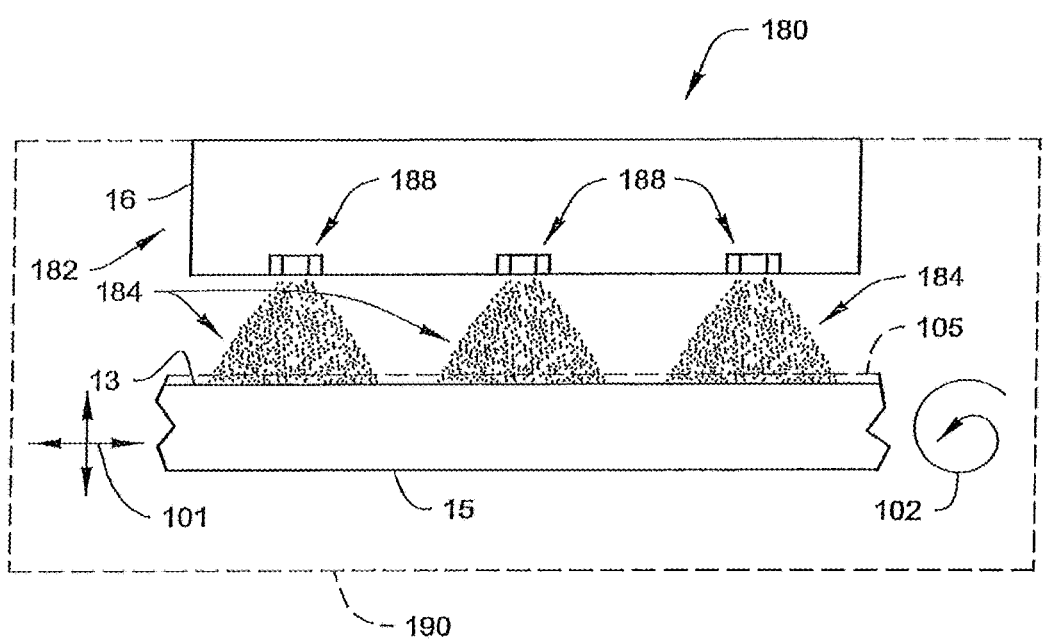
FIG. 8 shows a general diagrammatical illustration of a configuration of providing multiple electrospray nozzle structures according to the present invention that may be employed in the coating system shown generally in FIG. 1.

As shown in FIG. 6, inner opening 152 is provided along axis 161, and outer opening 154 is formed concentric therewith. An intermediate opening 153 is provide therebetween. At least in one embodiment, a biologically active material is provided in a liquid composition to the inner opening 152, a polymer at least partially dissolved in a solvent is provided to the intermediate opening 153, and a liquid diluent composition is provide to the outer opening 154. In cone-jet operation, a spray of coated particles is formed for coating an object 15. For example, at least in one embodiment, the coated particles may include biologically active material encapsulated by the polymer.

FIG. 7B is a more detailed diagram of an alternate exemplary capillary electrode configuration 400 for the distributor head 316 of FIG. 7A which includes the ability to spray particles from three flows of three different liquid compositions. Like reference numbers are used in FIG. 7B for corresponding like elements of FIG. 7A to simplify description of the alternate capillary configuration 400.

The capillary electrode configuration 400 includes a first capillary tube 412 having an axis coincident with axis 301 for receiving a first flow of a liquid spray composition from a source, e.g., a suspension of biologically active material, such as a drug. Further, a second capillary tube 414 is concentric with the first capillary tube 412. An annular space 487 between the inner and outer capillaries 412, 414 is used to receive a second flow of a liquid spray composition (e.g., a polymer dissolved in a suitable solvent) and provide the flow to the dispensing tip 495 for use in establishing the spray forward thereof. In more detail, the housing portion 430 includes an aperture 483 extending from a first end 480 of the housing portion 430 to a second end 482 thereof. An inlet port 420 opens into the aperture 483. The inlet port 420 receives the second flow of liquid spray composition 422 to be directed in the annular space 487 about the capillary tube 412.

The first capillary tube 412 has a first end 413 and a second end 415. The capillary tube 412 is positioned in the aperture 483 of the housing portion 430 of generally T-shaped configuration. The first end 413 of the capillary tube 412 is sealed to housing 430 using conductive element 431 at the first end 480 of the housing portion 430. The capillary tube 412 extends from the second end 482 of the housing portion 430 and with the second capillary tube 414 forms the annular space 487.

The second capillary tube 414 includes a first end 490 and a second end 491. The second capillary tube 414 is positioned so that it is concentric with the first capillary tube 412. The first end 490 of the second capillary tube 412 is coupled to the second end 482 of the housing portion 430 using conductive element 432. Further, the second end 491 of the second capillary tube 414 is held in place relative to the nozzle portion 322 by spacers 326. The second capillary tube 414 extends beyond the first capillary tube 412 a predetermined distance in the direction of the target surface to be coated; about 0.2 mm to about 1 mm. The portion of the second capillary tube 414 at the dispensing tip 495 which extends beyond the first capillary tube is tapered at a 60 degree to 75 degree angle for obtaining stable spray pattern and operation mode, e.g., consistent spraying patterns.

Further, the second capillary tube 414 extends beyond the second end 338 of the nozzle portion 322 a predetermined distance (d5), about 2 mm to about 5 mm. The first capillary tube 412 has diameters like that of capillary tube 320 of FIG. 7A. The second capillary tube concentric with the first capillary tube has an outer diameter of about 533.4 μm to about 546.1 μm and an inner diameter of about 393.7 μm to about 431.8 μm. The gap d6 at the tip of the second capillary tube 414 is in the range of about 10 μm to about 80 μm. The other configuration parameters are substantially equivalent to that described with reference to FIG. 7A. In such a configuration, dual streams of liquid spray compositions are provided for establishing a spray from dispensing tip 495 of the apparatus. However, further, a third liquid diluent composition 349 is also provided through inlet port 348 to dispensing tip 495.

Clearly, the present invention is not limited to the use of capillary-type nozzle structures as various suitable nozzle structures may be employed. For example, any nozzle structure suitable to provide a spray of particles according to the principles described herein may be used, e.g., slits that may provide various cone-jets, nozzle structures having portions thereof that are integral with portions of other nozzle structures, nozzle structures that form a part of a chamber wall, radially or longitudinally configured slots, or other multiple opening nozzle structures (e.g., micromachined nozzle structures that have dual or triple openings), etc.

Yet further as would be recognized by one skilled in the art multiple nozzle structures may be used to increase coating capacity according to the present invention. For example, as shown in FIG. 8, an electrospray coating system 180 employs a dispensing apparatus 182 to establish one or more sprays of particles 184 (e.g., sprays of microdroplets which evaporate to form sprays of coating particles). The dispensing apparatus 182 includes a plurality of nozzle structures 188 which operate in a manner like that of nozzle structure 18 as shown in FIG. 1 to provide a selected type of coating 105 on surface 13 of object 15 positioned in a defined volume (shown generally by the dashed line 190).

EXAMPLES SETUP

The examples to follow were carried out to produce nanocomposite coatings on surfaces with intricate architecture using an electrospray process that generates nanoparticles, initially focusing on coronary stents, and quantifying their physical characteristics. Further, the examples were carried out to achieve a level of reproducibility and performance of surface coatings. Yet further, the examples were carried out to:
1. Assess the relative importance of multiple coating process parameters on achieving the type of coating desired where outcome measures included coating weight, coating characteristics, and voltage required to maintain a stable cone-jet for each set of conditions including:
   a. Feed rate and composition of polymer, drug and solvent
   b. Polymer and drug concentration in sprayed material
   c. Conductivity of spray fluids
   d. Distance between spray tip and target
2. Using optimized process parameters, apply consistent coating weights to the surface of a coronary stent for one or more polymers, where the target weight of coating was between 400 and 600 μg for polymer and drug combined.
3. Determine the transfer efficiency for each coating, defined as the ratio of the coating weight to the mass of solid material sprayed.
4. Determine coating thickness using tangential cryomicrotomy and scanning electron microscopy and profilometry.
5. Determine coating characteristics, surface uniformity, and adherence of each coating type before and after balloon expansion of the stent.
6. Determine the uniformity of the drug/polymer matrix exploring other possibilities including atomic force microscopy and FTIR microscopy.
7. Determine the stability of biodegradable coatings under high ambient humidity.

Coating Reagents Used in the Examples

For the primary coating experiments, conducted to determine coating consistency and to optimize process-control variables, we selected polymers available on the market that represented a range of potential coating materials, from biodegradable materials to drug-eluting materials. The required solvents to dissolve these polymers ranged from solvents with higher dielectric constants (e.g., acetone and methanol) to solvents with lower dielectric constants (e.g., tetrahydrofuran and toluene).

The majority of experiments were made using two polymers: Poly(DL-lactide-co-ε-caprolactone, 80/20) (PLCL), inherent viscosity 0.77 dL/g in chloroform, is a biodegradable polymer that was available from Absorbable Polymers International, Pelham, A L, USA; and Chronoflex AR (CFR) is polyurethane 22% solid in dimethylacetamide. CFR, a drug-eluting material, is available from CardioTech International, Wilmington, Mass., USA.

Solvents used for these various polymers included acetone, chloroform, tetrahydrofuran (THF), methanol (solvents were HPLC grade) and phosphate buffer, pH 7.4, all available from Sigma-Aldrich, St. Louis, USA. We also conducted exploratory spray experiments with two additional polymers, poly(isobutylene) (PIB) and poly(tetrahydrofurfuryl methacrylate-co-ethyl methacrylate) PTHFMA-EM, also available from Sigma-Aldrich.

Initially three drugs were proposed for use in the coatings: dexamethasone, rapamycin and paclitaxel; e.g. see Ranade et al (2004). In the course of these studies, we sprayed both dexamethasone and paclitaxel successfully. The samples produced during these experiments were going to be analyzed on multiple shared instruments at the University of Minnesota. Because of the potential toxicity of rapamycin and paclitaxel and the possibility of contaminating the shared instruments, we elected to conduct the characterization studies using dexamethasone as the primary drug agent. Dexamethasone (99% purity) was available from Alexis Biochemicals, San Diego, Calif., USA.

Solutions of polymers were prepared at different concentrations as determined by the spraying conditions. A variety of polymer concentrations and solvent combinations were investigated; acceptable concentrations (weight/volume) and primary solvents included PLCL 5% in acetone or a blend of acetone and chloroform, CFR 2% in THF or a blend of THF and methanol, PIB 1% in THF, and PTHFMA-EA 2% in THF, e.g. see Alexis et al (2004), Puskas et al (2004), Szycher et al (2002), and Verhoeven et al (2004). Dexamethasone was added to polymer solutions, with final concentrations varying from 10% to 20% of the polymer weight, resulting in a 10:1 polymer:dexamethasone ratio by weight. Conductivity of solvent solutions was adjusted to appropriate ranges, typically by adding μl quantities of concentrated nitric acid, measured using a Orion Benchtop Conductivity Meter, model 555A with probe M (Thermo Electron Corp., Waltham, Mass., USA).

The optimal spray solvent for each polymer was determined by comparing the various solvents specified as compatible with each polymer by the manufacturer and assessing spray performance in terms of ability to form a stable cone-jet (i.e., stable dark tip appearance, no fluttering between cone-jet and non-cone-jet mode, and no corona discharge, see FIG. 2C herein). A stable cone-jet is required to maintain uniformity of particle size during the spray process. Likewise, optimal feed rates were determined by evaluating the voltage required to generate a stable cone-jet spray mode while, at the same time, visually inspecting the target for obvious flaws such as spatter marks on the surface that were seen when the cone-jet was disrupted. This process produced a set of voltages and feed rates for each polymer and solvent combination that were compatible with electrospray operation in the cone-jet mode.

Targets Used for Coating Examples

Originally both stainless steel springs made of 316 stainless steel, and stents made from the same material were to be used. While we did make some use of the springs in our initial process development work, it was determined that stents should be used. Generic stents that could be expanded in diameter 3-fold by balloon were obtained (Pulse Systems, Concord, Calif., USA). These were fabricated from 316 stainless steel that was annealed and electropolished. Dimensions were 12 mm in length, 1.57 mm in outer diameter and 1.30 mm in inner diameter, a size and general configuration that is equivalent to stents in current use.

Because some of the coating characterization tools could not be used to assess a rounded surface, flat stainless steel plates were used for some aspects of coating development. One cm-square pieces were pressed from 30.5 cm-square mirror-finished 316 stainless steel sheets 0.79 mm thick (McMaster Carr, Chicago, Ill., USA). For coating experiments, the coating was sprayed on the mirror-finished side of the small cut pieces.

Electrospray Coating Apparatus

Two electrospray systems were used in these experiments. One system, which had a fixed target, was used to explore optimum spray conditions. The second system, which had a movable spray target platform, was used as the primary stent-coating apparatus. The spray head in both of these systems was a custom-manufactured dual capillary design, in which each capillary was fed by external syringe pumps (Harvard Apparatus, Holliston, Mass., USA). A high-voltage power supply (Bertan Associates, Hicksville, N.Y., USA) was used to apply voltage to the spray tip, typically over a range of 3.5-5.5 kV at ~2.5 mA. The target was moved into position by a motor-driven, computer-controlled, movable stage that permitted vertical and horizontal adjustments in positioning the target with respect to the spray tip as well as a variable advancement rate of the target through the spray field. The spray operation was imaged using a video inspection microscope (Panasonic) that produced real-time images of the spray tip as well as the target. The spray operation was contained within a negative-pressure chamber that drew gas supply (air, nitrogen or carbon dioxide) through a filtered supply line and was vented through a filter and fume hood. Temperature and relative humidity were monitored continuously.

Unless otherwise indicated, the spray apparatus used to coat objects by electrospray was equivalent to that shown in and described with reference to FIG. 7A. The apparatus included a dual concentric opening dispensing device 314 extending along axis 301. First end 304 was formed of conductive portions to facilitate application of voltages or ground to capillary tube 320. The capillary tube 320 was formed of stainless steel and had an outer diameter of 560 µm and an inner diameter of 260 µm. Further, the distributor head 316 included a nozzle portion or casing 322 that was an elongate substantially cylindrical metal casing concentric with the capillary tube 320 for providing an outer opening 392 concentric with inner opening 391 of the capillary tube 320. The casing or nozzle portion 322 included a first end portion 336 which tapered at section 335 thereof to a narrower second end portion 338. The second end portion 338 extended from the tapered section 335 and is concentric with the second end 332 of the capillary tube 320. The distance from the end of the tapered section 335 to the end of the metal casing 322 is about 4.7 mm. The outer diameter of the second end portion 338 is about 1050 µm and the inner diameter of the second end portion 338 is about 680 µm. The second end 332 of the capillary tube 320 extends beyond the second end portion of the metal casing or nozzle portion 322 towards the target surface to be coated by a distance of about 5 mm.

The dispensing device was constructed of various materials. Primarily, the conductive elements (e.g., element 316) were constructed of stainless steel, the apparatus was used in a chamber made of plexiglass, and insulative parts (e.g., element 383) thereof were made of a plastic, black delrin, material.

The electrospray was operated in a cone-jet mode with a flow of 4000 cc/min flow of $N_2$ through port 354 and about the same amount exhausted from the coating system.

Determining Optimal Spray Operating Parameters

A Design of Experiment (DOE) approach was taken to setting up the experimental conditions and evaluating the impact of the various process parameters (e.g., see *DOE Simplified: Practical Tools for Effective Experimentation.* Anderson M J and Whitcomb P J. Productivity, Inc., New York, N.Y. 2000). Using this approach, a matrix of different operating conditions was established and used to spray the flat stainless steel squares described herein. Parameters evaluated included polymer concentration, drug concentration, conductivity of the solutions, spray feed rates, and spray distance to target. Outcome variables recorded included voltage, stability of the cone-jet spray mode, coating weight, and the surface qualities of the coating under SEM imaging. Results of these experiments were used to guide the selection of initial operating parameters for the stent-coating experiments.

Coating Weight

For each coating, at least 10 to 12 individual stents were sprayed consecutively. Coating weight was determined by weighing the spray target before and after spraying using a Cahn electrobalance, Model 21. A goal was to achieve coatings of approximately 500 µg per stent; however, we also conducted some spray experiments where very thin coatings of approximately 40 µg were applied, or where we coated only certain regions of the stent, for a coating weight of approximately 30 µg.

Transfer Efficiency

Transfer efficiency is defined as the ratio of the mass of solid material sprayed to the weight of the coating. Only the weight of coating on the target stent was determined; the weight of material that adhered to the spray fixture was not used in the calculation due to the inability to weigh the much larger fixture reliably. Most likely the portion of sprayed material that was not present on the stent was captured by the fixture due to the force of attraction generated by the strong electrical field.

Coating Uniformity

Stents were imaged using light and scanning electron microscopy (SEM) to verify coating qualities, surface uniformity, and lack of void areas or webbing at strut junction points. A light microscope image was used to record lack of obvious deformity in the stent structure. Coating images were assessed on multiple points over the outer and inner surfaces of the struts, at low (45×) and high (5000× and 20,000×) magnifications. For production lots, samples were selected randomly from each lot.

Surface coating thickness uniformity was also assessed by SEM imaging of cross sections of tangential cuts made by glass blade microtome at two or more points on each individual stent. Because the nanocomposite coating distorted under conditions of room-temperature sectioning, tangential cryomicrotomy was used to cut the coating on the selected strut at low temperature. A series of experiments were done to find the optimal temperature. At −120° C., the coating started coming off as pieces, leaving the cutting edge clean. Because of the low stiffness of the coating, a glass knife was used to cut at 1 mm/s cutting rate and 0.5 µm per step feeding rate. SEM images were then taken and the thickness for each type of coating was estimated.

Coating thickness was also assessed using profilometry. Because the profile across the curved stent surface could not be obtained, coatings were sprayed on 1-cm-square polished 316L stainless steel plates, using similar spray conditions and time for each of the polymer-drug blends and surface types, respectively. Three squares were placed on a flat fixture and coated during a single spray period. Samples were evaluated using a Dektak 3030 profilometer (Veeco Instruments, Woodbury, N.Y., USA) and a Tencor P-10 profilometer (KLA-Tencor Instruments, San Jose, Calif., USA). As the stylus scanned the surface, the profile was recorded. The stylus load was kept at 0.05 mg so that the coating would remain intact without leading to false measurement. Thickness data was derived from the profile.

Imaging

Imaging experiments utilized light images of stents taken using a Nikon Model SMZ1500 stereomicroscope. Higher-magnification surface images were taken using a Hitachi Model S-3500N VP scanning electron microscope (SEM). For this, samples were mounted and then coated with gold under 250 µm Hg of argon, using 15 µA of current for 1.5 minutes, and then placed on the microscope stage. For atomic force microscopy, a Digital Instruments Nanoscope III MultiMode Scanning Probe Microscope with an auxiliary Extender electronics module was used in tapping mode. For Fourier Transform Infrared (FTIR) Spectra microscopy, PLCL coated stents with and without dexamethasone were imaged using a Nicolet Magna-IR 750 model attached to a Nic-Plan IR Mcroscope. The microspectroscopy was done under reflectance mode with 10 µm beam size. The background was collected on a mirror with gold coating. FTIR spectra on multiple spots of the coating were compared.

Coating Adherence

Two techniques were used. Coating adherence after balloon expansion of the stent was assessed by SEM imaging, looking for patterns of obvious cracking or delamination of the coating surface from the stent structure. In another approach, we also explored use of a "tape test," in which the coated stent mounted on a rigid wire fixture was placed with gentle pressure onto the adhesive side of Scotch Magic tape (3M, St. Paul, Minn., USA) and then removed from the tape quickly by pulling at either end of the wire fixture. This method was less satisfactory due to problems standardizing the technique and deforming the stent.

Effect of Humidity on Coating Surface

Because the PLCL polymer is known to biodegrade in the presence of water, we evaluated the effect of short-term exposure of a high moisture environment on the surface characteristics. Stents coated with the PLCL open matrix coating and the PLCL smooth coating (i.e., closed film coating) were exposed to 99% relative humidity at room temperature in a closed container. Stents were evaluated at 24 and 72 h and these images compared to control stents that were maintained under dry conditions.

Statistical Methods

Experimental outcome data descriptive statistics were calculated using Microsoft Excel and reported as mean, standard deviation (SD) and coefficient of variation (CV).

RESULTS OF EXAMPLES

Design of Experiment (DOE) Results

Evaluation of the Spray Process Variables on Coating Matrix

Figures 12, 13:
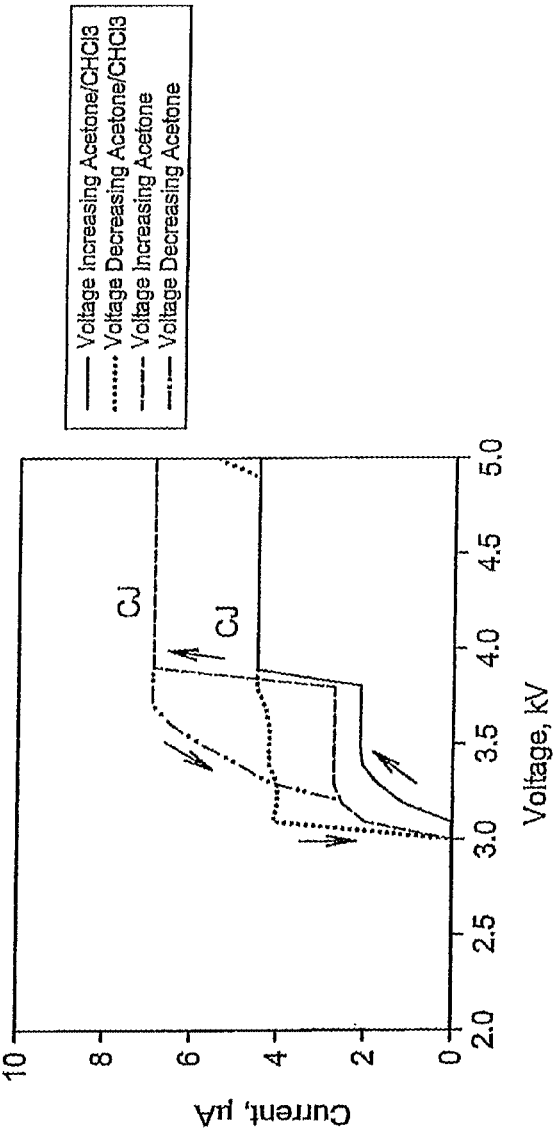
FIG. 12 shows a graph of hysterisis effect on the relationship between voltage and current through the spray target while operating the electrospray technique according to one or more examples provided herein.
FIG. 13 shows a table of stent and coating weights for each lot of various coating polymers and surfaces according to one or more examples provided herein.

These experiments were conducted to investigate the impact of PLCL polymer concentration in final spray stream, presence of the drug dexamethasone (DEX), conductivity, and distance from spray head to target on the final coating matrix appearance. The desired coating matrix was a uniform open matrix of round particles. As explained above, a Design of Experiment (DOE) approach was taken to setting up the experimental conditions and evaluating the impact of the various process parameters. This is a highly efficient way of identifying optimal coating conditions for a particular polymer and coating finish. The experimental conditions are summarized in the table of FIG. 9 and the images of the resulting coatings shown in FIG. 10. The table of FIG. 9 includes the experimental conditions and outcome measures to assess impact of process parameters on achieving desired coating surface appearance.

The effect of the process parameters with respect to achieving the desired coating appearance is summarized in the table of FIG. 11 which shows the relationship of process parameters to experimental outcome variables (↔ little effect, ↑ increase). As can be seen from this chart, a higher polymer-to-diluent ratio (i.e., liquid spray composition provided at the inner opening or inner capillary to liquid diluent composition provided at the outer opening of the spray apparatus), is the sole factor associated with greater coating weight; spray distance (i.e., distance from dispensing end to the target) and conductivity of the diluent in the outer capillary (which has a major impact on conductivity of final spray stream) are both associated with the requirement for a higher spray voltage, and a higher conductivity is the sole factor associated with achieving the desired coating surface.

Another factor that was determined to affect the stability of the spray operation was defining the range of voltage for a particular fluid that was associated with a stable cone-jet mode. The cone-jet mode is the operating mode that produces the most uniform particles. The voltage that must be applied to achieve the cone-jet mode is related to the conductivity of the spray fluid, so in one sense it is an outcome measure defined by the feed fluid. However, it can also be controlled within a certain range to produce the cone-jet operation. As shown in FIGS. 2A-2C herein, voltage is increased, the dripping spray tip (FIG. 2A) first assumes a pulsating appearance (FIG. 2B) and eventually the cone-jet mode (FIG. 2C) which produces the most stable nanometer-sized particles.

As has been reported previously by Chen and Pui (1995), there is hysteresis in the operating current across the target during cone-jet operation and the operating voltage, which is different when the voltage is increasing than when it is decreasing. This is a unique relationship for each polymer/solvent combination, as shown in FIG. 12. In this experiment, the polymer was PLCL and the solvent was acetone alone or a blend of acetone and chloroform (90:10) (used to produce the open matrix and smooth coating (i.e., closed film) surfaces, respectively). FIG. 12 shows the hysteresis effect on the relationship between voltage and current through the spray target while operating electrospray in the cone-jet mode. Cone-jet (CJ) operation was observed within the voltage ranges that were marked by rapid changes in the current, depending on whether voltage was increasing or decreasing.

These process control experiments are significant because they demonstrate that a set of operating parameters can be identified for a given polymer, drug and solvent combination that produce a desired surface finish (e.g., selection of a particular type of coating). The Design of Experiment (DOE) methodology provides a powerful tool for identifying these parameters. This systematic approach provides a foundation for scale-up in manufacturing and designing automated process control features.

Results of Coating Weight Consistency for Production Lots of Three Different Coating Surfaces Three separate lots of a minimum of 10 stents each were coated with two different polymers, both containing the anti-inflammatory agent dexamethasone. The biodegradable polymer PLCL was used to apply coatings with two unique surface characteristics—a highly porous ("open matrix") finish, or a smooth ("closed") finish. The drug-eluting polymer Chronaflex AR produced a smooth, "closed" finish with the family of solvents investigated. Coating spray times were approximately 20 minutes for each of these spray runs. Images for each of these coating surfaces are provided under description related to "Coating Adherence," below. Stent and coating weights are summarized in the table of FIG. 13 which shows stent and coating weights for each lot of the various coating polymers and surfaces.

Figure 14:
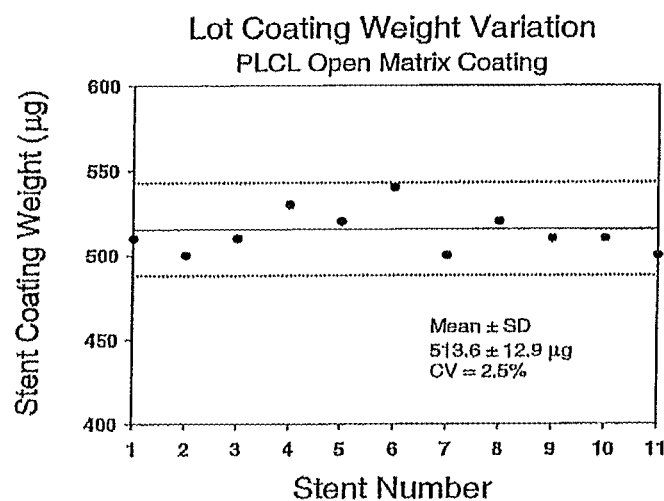
FIGS. 14-16 show graphs of coating net weights for lots of stents provided with open matrix coatings and closed film coatings according to one or more examples provided herein.

Coating weights of individual stents were plotted for each lot to determine how many individual samples had coating weights exceeding 2 SD. FIG. 14 shows a plot for the open-matrix coating with PLCL, FIG. 15 for the smooth coating (i.e., closed film) with PLCL, and FIG. 16 for the smooth coating with Chronoflex AR. Notably, in none of the lots did a single stent coating weight exceed 2 standard deviations.

FIG. 14 shows the coating net weights for a lot of stents produced with the open matrix PLCL coating. The optimum solvent for PLCL was acetone. To produce this coating finish, the ideal feed rate of the polymer/acetone solution was determined to be 6.5 µl/min sprayed at a distance of 10 mm. (See, for example, DOE results for the impact of various spray operating parameters on final coating appearance.) Maintenance of the cone-jet mode required some increase of voltage during each individual spray run. For the stents in this lot, the inner capillary feed was PLCL 5% and DXM 0.5% in acetone at a rate of 1.5 µl/min, with an outer capillary feed of acetone, with nitric acid added to adjust conductivity to 6.8 µS/cm, at a flow rate of 5 µl/min.

Figure 15:
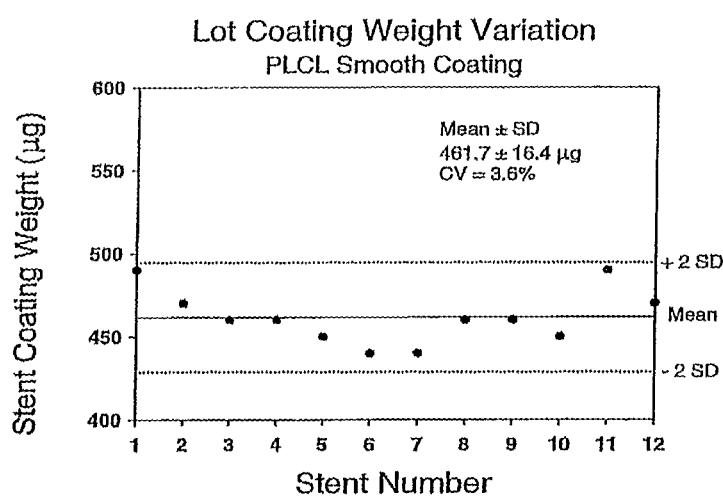

FIG. 15 shows coating net weights for a lot of stents produced with the smooth PLCL coating (i.e., closed film coating). To produce this coating finish, the feed rate of the polymer/acetone/chloroform solution was 10.75 µl/min sprayed at a distance of 10 mm. Voltage was stable throughout each individual spray run. For the stents in this lot, the inner capillary feed was PLCL5% and DXM 0.5% in acetone at a rate of 0.75 µl/min, with an outer capillary feed of acetone 40% and chloroform 60%, at a flow rate of 10 µl/min.

Figure 16:
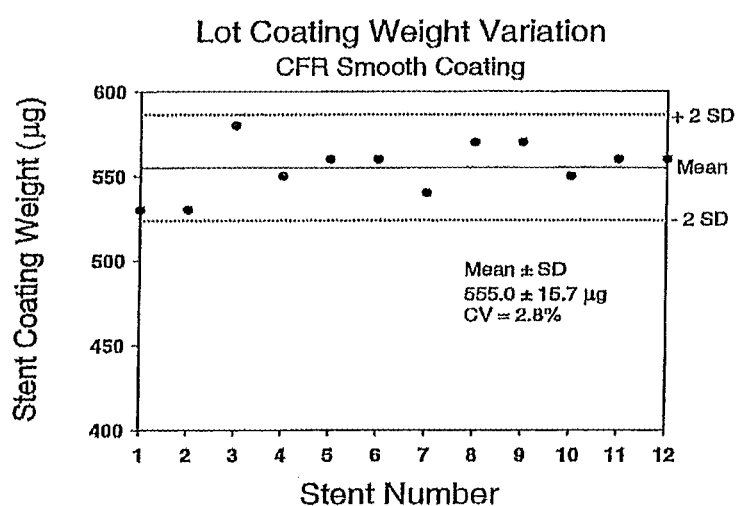

FIG. 16 shows coating net weights for a lot of stents produced with the smooth Chronoflex AR coating (i.e., closed film coating). The optimum solvent for this polyurethane was a blend of tetrahydrofuran and methyl alcohol. Polymer solution feed rate was 10.0 µl/min sprayed at a distance of 8 mm. Voltage was stable throughout the coating of each individual stent. For the stents in this lot, the inner capillary feed was CFR 2% and DXM 0.2% in THF 83.3% and methanol 16.7% 2.0 µl/min, with an outer capillary feed of THF 83.3% and methanol 16.7% at a flow rate of 8 µl/min.

The consistency of these coating runs is significant because it demonstrates that these three different coatings can be reproduced with minimal between-stent variation in coating weight. These experiments furthermore demonstrate that coatings of acceptable weights can be achieved with these particular drug/polymer combinations.

One process parameter is the length of spray time. The coatings in these experiments, made using single spray units, took a spray time of 20-25 min. This can be shortened by operating multiple spray units in serial or parallel or by adding additional spray heads targeting each individual stent.

Coating Transfer Efficiency Results

Figures 17, 18:
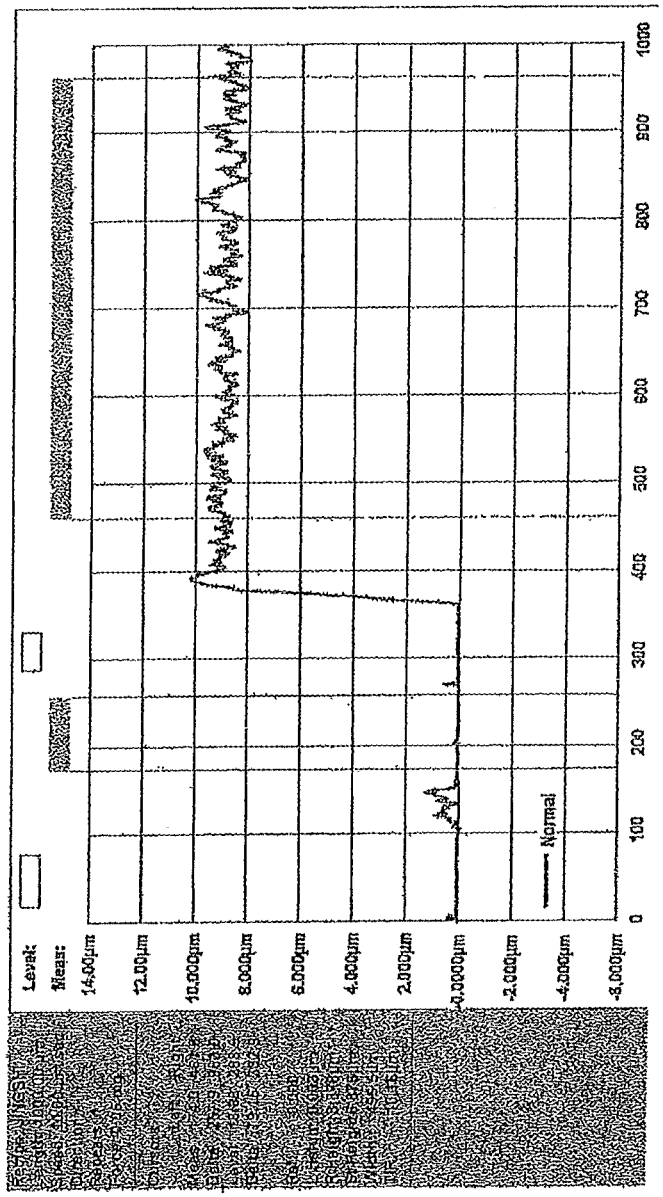
FIG. 17 shows a table regarding coating transfer efficiency as a function of coating polymer, surface, and solvents, according to one or more examples provided herein.
FIG. 18 shows a graph of a profilometer scan showing coating thickness according to one or more examples provided herein.

Coating transfer efficiency is the amount of sprayed material that is applied to the stent surface. Transfer efficiency for each of the three coatings is shown in the table of FIG. 17 which shows coating transfer efficiency as a function of coating polymer, surface and solvents. The lowest transfer efficiency was seen for the PLCL open matrix finish. The spray pattern for this finish was much broader than seen for the other two finishes due to the higher conductivity of the sprayed material. Higher conductivity fluids generate smaller nanoparticles, which appears to correlate with wider spray patterns. A broader spray pattern means that more material is applied beyond the stent target area to the fixture.

Coating Thickness Results

Coating thickness was assessed by two different methodologies: profilometry, which uses a surface scan on the coating and a baseline uncoated reference area, and cyromicrotomy followed by SEM imaging.

Profilometry was only capable of measuring thickness on flat surfaces. Samples were prepared by coating the surface of the polished 316 stainless steel in squares described earlier. While coating thickness estimates were roughly equivalent to those reported above for cryomicrotomy, this method is of limited utility because it is not applicable in its present form for the curved surface of the coronary stent. An example of a scan is shown for a PLCL open matrix coating on the flat surface in FIG. 18 which is a profilometer scan made with a Tencor P10 instrument. Coating thickness was estimated at approximately 10 µm. It may be possible that profilometry could be modified for use on stents.

Figure 19:
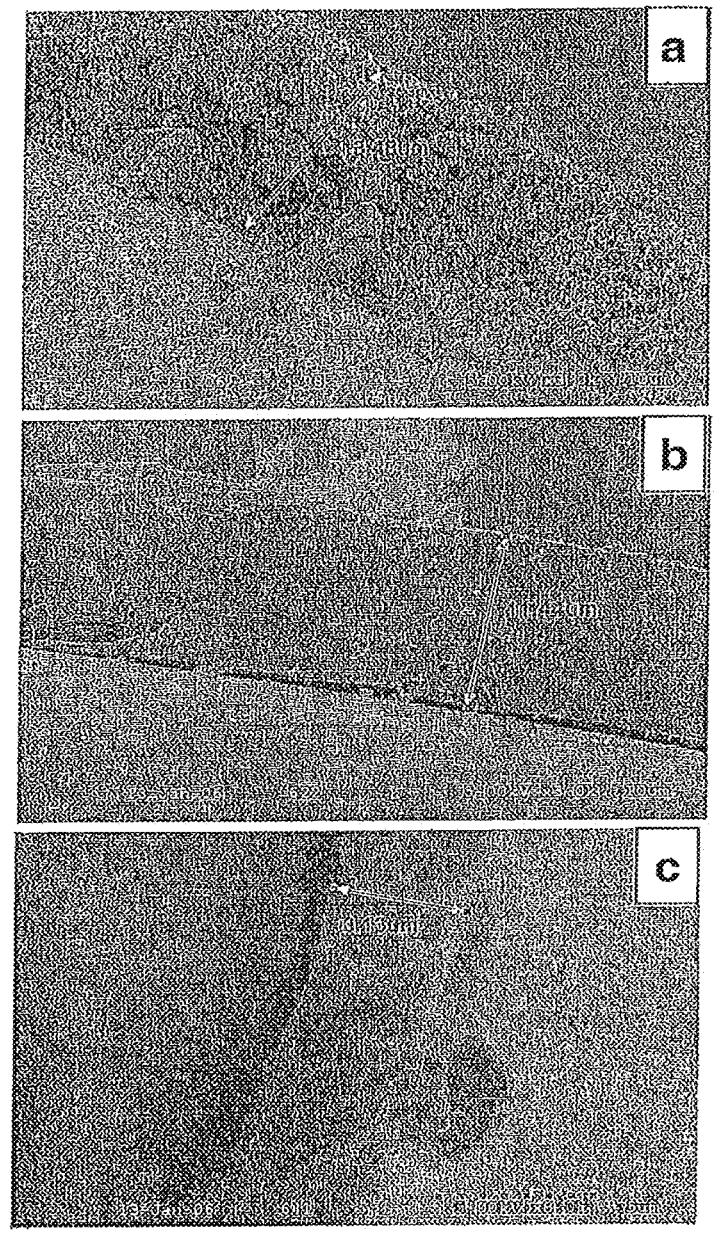
FIG. 19, which includes images a-c, show cross-sectional images of three coatings produced according to one or more examples provided herein.

Cryomicrotomy followed by SEM imaging was of considerably greater utility. The cross-sectional images also provide a view of the uniformity of the coating. Examples of microtomed samples are shown in FIG. 19, images a-c. FIG. 19 shows cross-sectional images of the three coating types produced during the production lots. Extraneous material in each image is debris caused when the microtome glass knife shatters the surface during section cuts. FIG. 19, image a, shows an open matrix PLCL coating. The crystalline-appearing debris is fragments broken from the glass knife when it hits the stent surface. Coating thickness is measured to be 13.48 μm. FIG. 19, image b, shows a smooth PLCL closed film coating. Thickness is measured to be 11.44 μm. The minor separation between the coating and the stent surface that is visible in this image may be artifact produced when the coated stent is cooled under liquid nitrogen in preparation for sectioning. FIG. 19, image c, shows a Chronoflex AR coating. Thickness is measured to be 3.13 μm.

Cryomicrotomy and SEM imaging is the most practical method for assessing coating thickness. Ideally a profilometer-type assay could be developed, using cryomicrotomy/SEM imaging as a benchmark for method validation.

Results for Coating Surface Characteristics, Surface Uniformity and Adherence, Before and after Balloon Expansion Coating surface characteristics were initially evaluated through pilot studies and SEM imaging. After optimizing process variables for a particular polymer/drug combination and the desired surface architecture, we needed to demonstrate that these surface characteristics could be reliably and consistently produced. Using the uniform lots of coated stents, the consistency of coating surface characteristics was assessed by randomly selecting and SEM-imaging three stents from each lot in the non-expanded state and three stents after balloon expansion to 3 mm. Representative images for each coating (as shown by the key to the images provided in the table of FIG. 21) are shown in Figures a-f. Small type information too small to read at the bottom of each image is summarized in the key.

Figure 20:
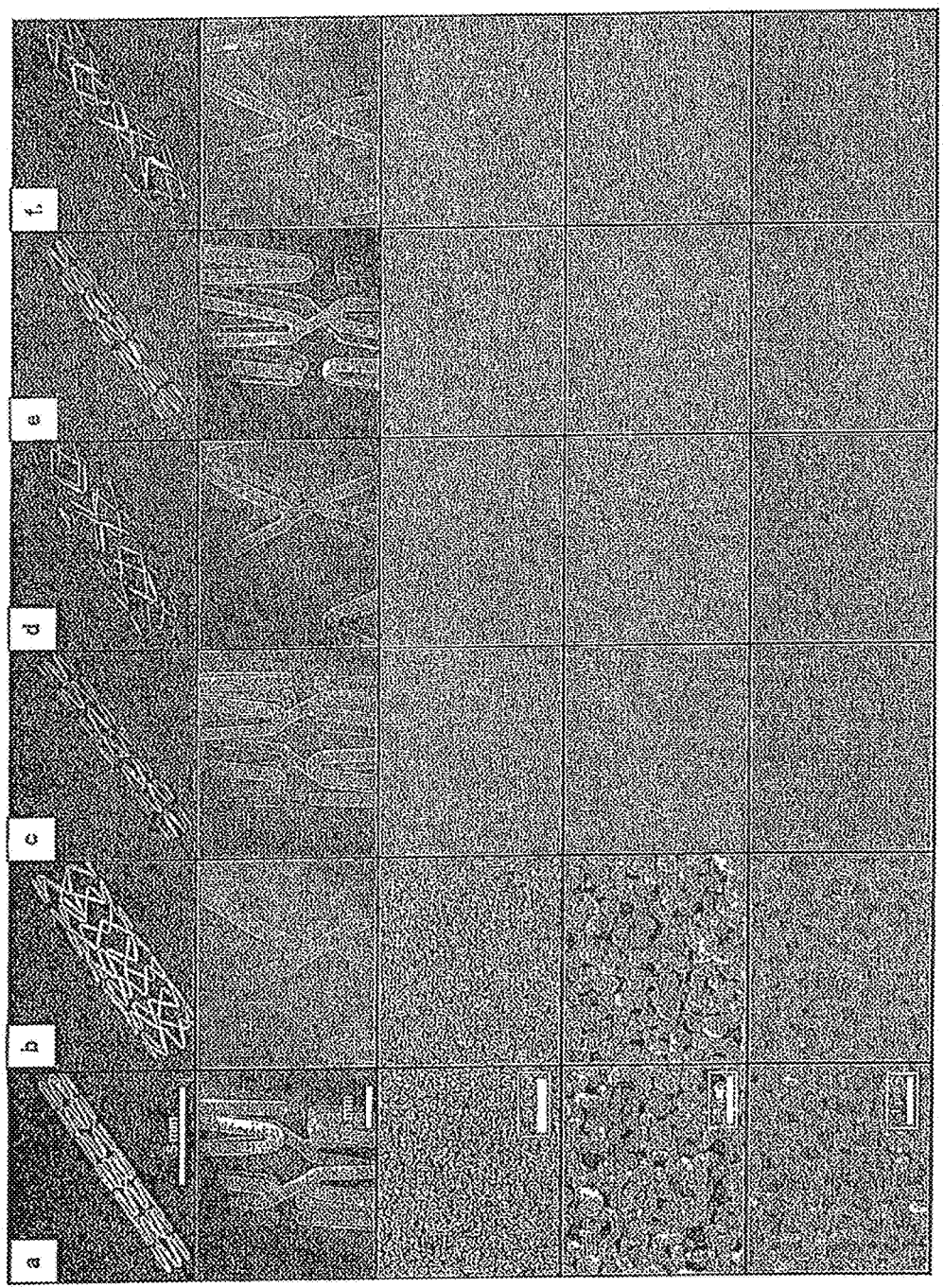
FIG. 20, which includes images a-f, shows SEM images of coatings according to one or more examples provided herein.
Figure 22:
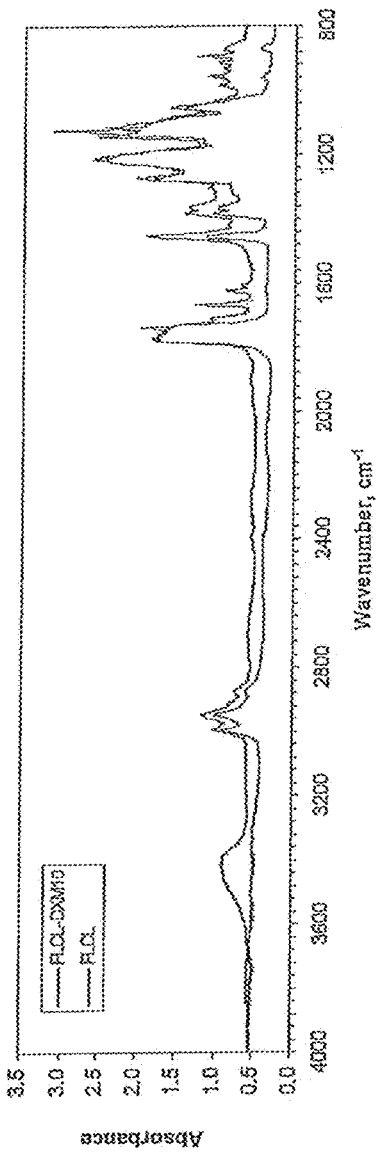
FIG. 22 shows an FTIR Spectra of a couple of coatings according to one or more examples provided herein.

As is clear in the images of FIG. 20, images a-f, all three types of coating surfaces are uniform without obvious coating voids. Coatings were deemed to be acceptable if they exhibited overall uniformity, no obvious coating voids, evenness on the internal surface of the strut, and lack of webbing or pooling and strut angles.

We also conducted pilot spraying experiments using PIB 1% in THF, and PTHFMA-EA 2% in THF, both with dexamethasone at 10% the level of the polymer. The PIB gave a smooth coating, while the PTHFMA-EA gave a large, irregular open matrix surface.

In the images shown in FIG. 20, a-f, all surfaces appeared to be adherent prior to balloon expansion. The PLCL open matrix coating showed evidence of minor cracking along strut angles after balloon expansion. At higher magnification (not shown), these cracks did not appear to reach the stent surface. None of the coatings delaminated after balloon expansion. We also evaluated adherence using the "Scotch Tape" test. In practice, this test was difficult to standardize. While this removed some of the material from the open matrix PLCL coating (image not shown), some particulate surface remained. This finding is consistent with the balloon expansion observation.

These images demonstrate that all three polymer/drug coatings could be uniformly applied. We were only able to produce the open matrix surface with PLCL, but this was very uniform. Both PLCL and Chronoflex AR gave very smooth coatings with minor surface variations only visible at 20,000× magnification. Inner and outer strut surfaces were similar in appearance and there were no obvious voids, demonstrating the important sheath-like coating that is achieved with the non-line-of-sight electrospray process.

The polymers listed in the examples that have been sprayed provide a strong foundation for extending the coating capabilities to other systems and/or for use on other medical devices or objects and also for developing routine SEM imaging as a key quality control assessment tool for scaled-up manufacturing.

Methods for testing coating adherence under likely stress conditions, include, for example, balloon expansion. Adherence could be improved for some polymers, if necessary, with use of a surface priming treatment on the stent surface. The open matrix PLCL coating showed minor cracking at the strut points after balloon expansion, providing information for further coating optimization.

Matrix Uniformity Results

In addition to SEM imaging, we undertook a limited evaluation of matrix uniformity with scanning probe microscopy (SPM) in tapping mode. Due to the technical difficulties in working with a curved surface, coated flat stainless steel squares were used as the sample. The response to the surface of the PLCL open matrix sample was overwhelmed by open topography. The response to the surface of the PLCL flat surface did not detect any differences in response over the area evaluated. Because dexamethasone is soluble in the solvents used to apply the PLCL, it is possible that the drug remained in an amorphous state uniformly distributed throughout the polymer.

We also explored using FTIR microscopy to evaluate chemical uniformity in the matrix. FTIR spectra on two spots of the coating were compared for stents coated with PLCL alone and in combination with dexamethasone. Spectra for PLCL alone and PLCL plus dexamethasone are shown superimposed in FIG. 22. The peaks at 1620 and 1600 $cm^{-1}$ represent the vibrational mode of A-ring and C=C stretch respectively and the peak at 1660 $cm^{-1}$ represents the $C_3$ carbonyl stretch of dexamethasone. Those three peaks are not present in the coating made without dexamethasone. The intensities of those peaks observed at different locations of the stent coated with PLCL plus dexamethasone (data not shown) were similar, suggesting that the dexamethasone (DXM) was also distributed uniformly.

Uniform distribution of drug throughout the coating matrix is required to ensure even delivery to the coronary vessel wall. SPM was not capable of discerning matrix differences with the polymer/drug combinations used in these experiments. While FTIR microscopy can detect the presence of drug at selected site it does not appear to be sensitive enough to provide quantitative information.

Matrix Stability with Humidity Results

Figure 23:
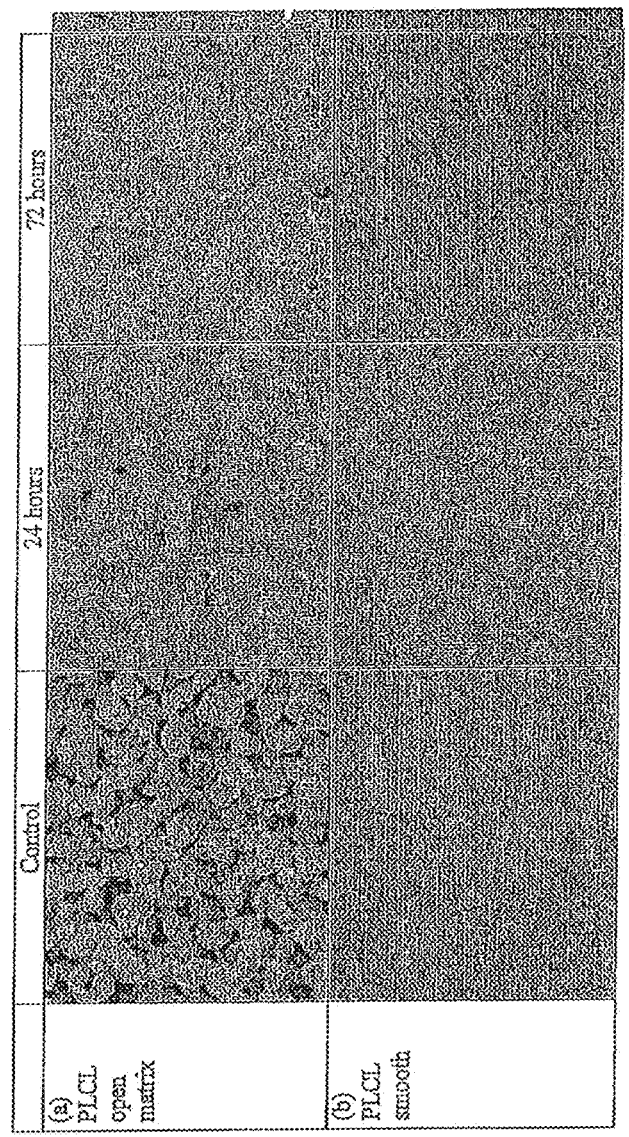
FIG. 23, which includes images a-b, show images of the effect of humidity on open matrix coatings and closed film coatings according to one or more examples provided herein.
Figure 24B:
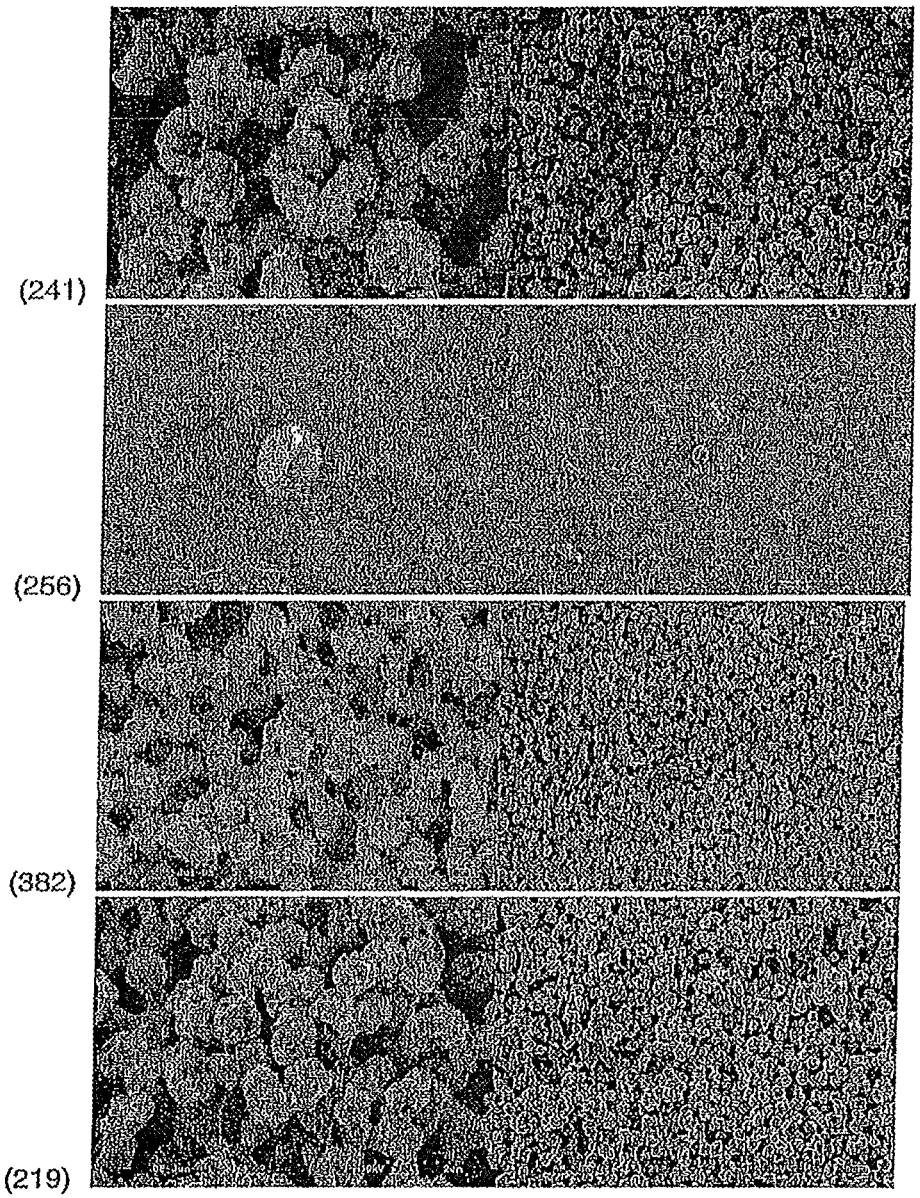
FIG. 24B shows respective images (higher magnification and lesser magnification) of the resulting coatings corresponding to the Sample #'s shown in the table.
Figures 25A, 25B:
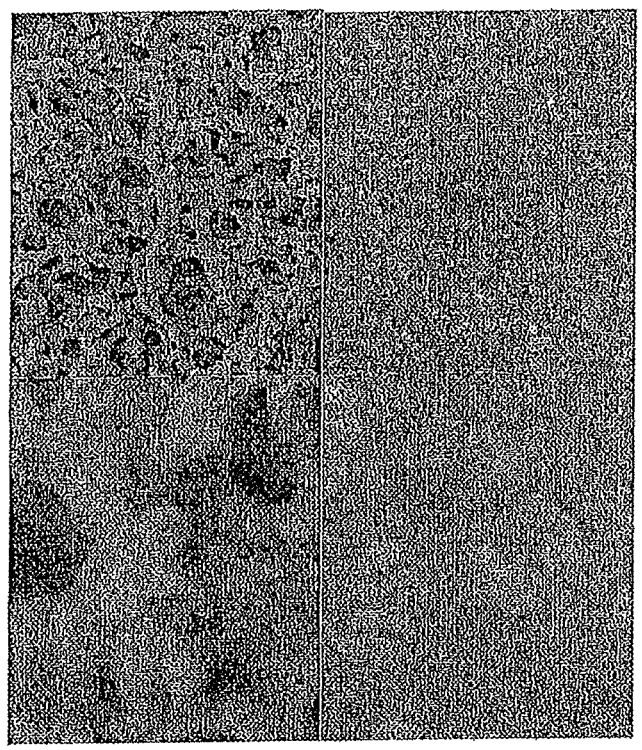
FIG. 25A shows a table of solutions and parameters used in the application of one or more coatings according to one or more examples provided herein.
FIG. 25B shows respective images (higher magnification and lesser magnification) of the resulting coatings corresponding to the Sample #'s shown in the table.
Figures 26A, 26B:
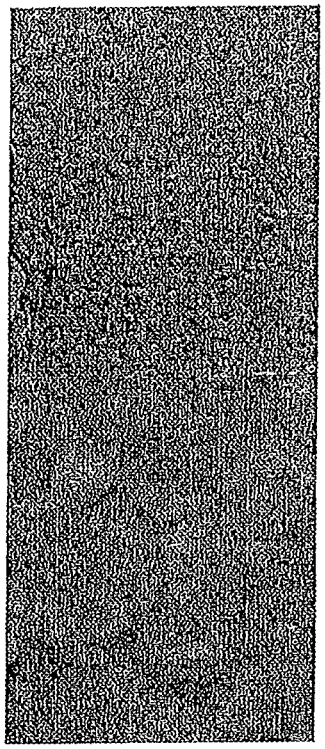
FIG. 26A shows a table of a solution and parameters used in the application of one or more coatings according to one or more examples provided herein.
FIG. 26B shows respective images (higher magnification and lesser magnification) of the resulting coating corresponding to the Sample # shown in the table.
Figures 27A, 27B:
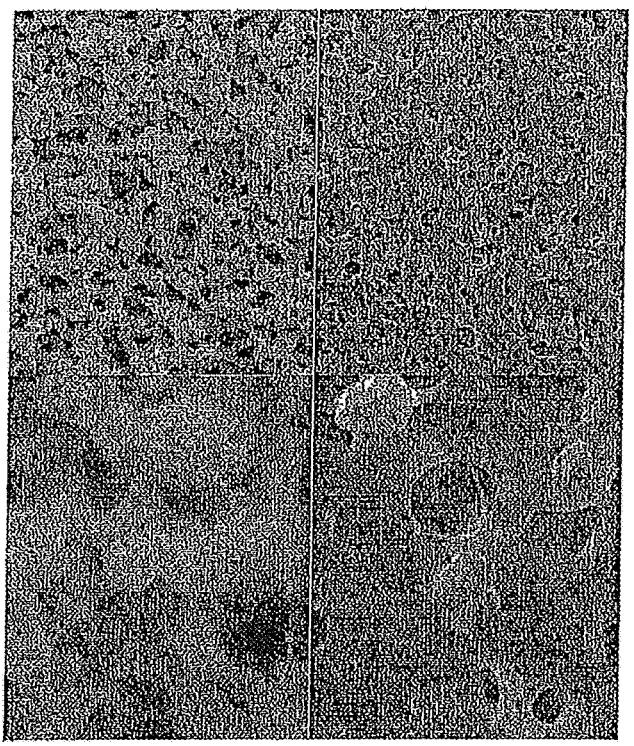
FIG. 27A shows a table of solutions and parameters used in the application of one or more coatings according to one or more examples provided herein.
FIG. 27B shows respective images (higher magnification and lesser magnification) of the resulting coatings corresponding to the Sample #'s shown in the table.
Figures 28A, 28B:
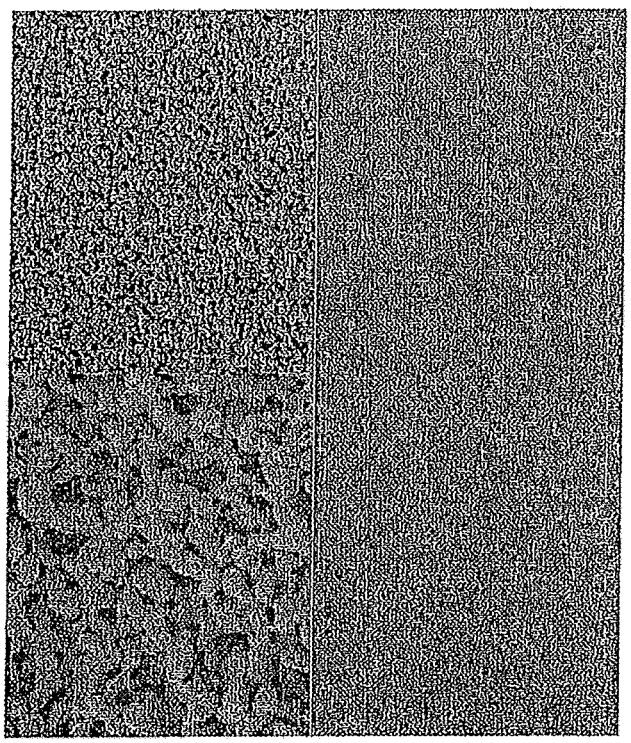
FIG. 28A shows a table of solutions and parameters used in the application of one or more coatings according to one or more examples provided herein.
FIG. 28B shows respective images (higher magnification and lesser magnification) of the resulting coatings corresponding to the Sample #'s shown in the table.
Figures 29A, 29B:
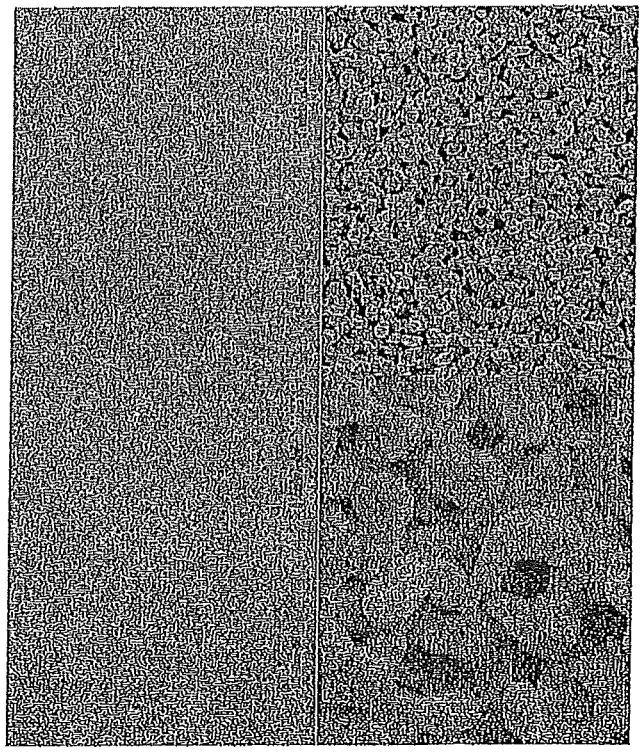
FIG. 29A shows a table of solutions and parameters used in the application of one or more coatings according to one or more examples provided herein.
FIG. 29B shows respective images (higher magnification and lesser magnification) of the resulting coatings corresponding to the Sample #'s shown in the table.
Figures 30A, 30B:
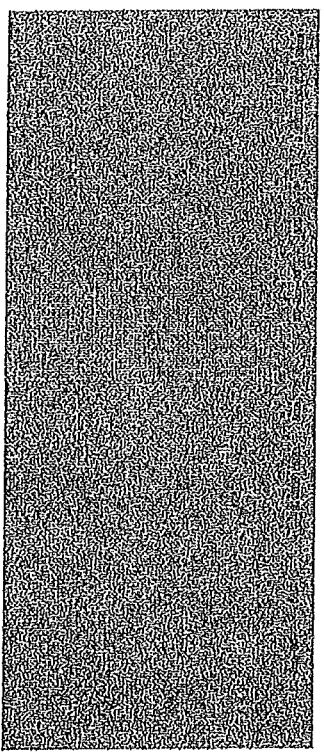
FIG. 30A shows a table of a solution and parameters used in the application of one or more coatings according to one or more examples provided herein.
FIG. 30B shows respective images (higher magnification and lesser magnification) of the resulting coating corresponding to the Sample # shown in the table.
Figures 31, 32:
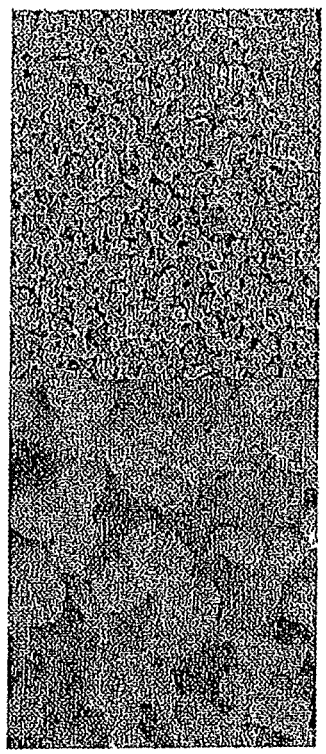
FIG. 31 shows a table of a solution and parameters used in the application of one or more coatings according to one or more examples provided herein.
FIG. 32 shows respective images (higher magnification and lesser magnification) of the resulting coating corresponding to the Sample # shown in the table of FIG. 31.
Figures 33, 34:
FIG. 33 shows a table of a solution and parameters used in the application of one or more coatings according to one or more examples provided herein.
FIG. 34 shows respective images (higher magnification and lesser magnification) of the resulting coating corresponding to the Sample # shown in the table of FIG. 33.

When stents coated with the PLCL polymer and dexamethasone were exposed to a 99% relative humidity (RH) environment at room temperature, changes in the surface morphology were seen for both the smooth coating and the open-matrix coating, shown in FIG. 23, images a-b. With the open-matrix coating of FIG. 23, image a, the round particles present in the control stents were no longer distinct by 24 hours and appeared to have become contiguous by either swelling or melting. With the smooth coating of FIG. 23, image b, surface irregularities not present on the control stents appeared as early as 24 hours.

While the PLCL biodegradable polymer provides considerable flexibility in engineering both smooth and particulate surface features, it is very sensitive to environmental moisture. This surface could be a way of supplying a rapid burst of drug release due to the high surface area that is exposed to the points of contact in the vessel.

OTHERT APPLIED COATING EXAMPLES USING LIQUID SPRAY AND DILUENT COMPOSITIONS

Using the same electrospray setup described above, various solutions were sprayed to form coatings on objects as shown below. Liquid spray compositions (e.g., solids and solvents) were provided as the inner flow (IF) to the inner opening of the dual concentric opening nozzle structure (i.e., inner capillary) and liquid diluent compositions were provided as the outer flow (OF) to the outer opening of the dual concentric opening nozzle structure as indicated in the tables associated with each example. In each example, images are matched to the table by the Sample #.

Example 1

The solution samples listed in the table of FIG. 24A were sprayed under the conditions provided therein. FIG. 24B shows images of the coatings resulting from the spraying of the samples in cone-jet mode. The images for each solution are provided in higher and lesser magnification. The solution (0.9% poly(styrene-b-isobutylene-b-styrene (abbreviated SIBS)+0.1% paclitaxel (PTx) in 85% tetrahydrofuran (THF) and 14% methanol (MEOH) could be sprayed as open matrix coating. In order to obtain a closed film (smoother) coating, toluene was added into the mixture.

Example 2

The solution samples listed in the table of FIG. 25A were sprayed under the conditions provided therein. FIG. 25B shows images of the coatings resulting from the spraying of the samples in cone-jet mode. The images for each solution are provided in higher and lesser magnification. The solution (0.9% SIBS+0.1% PTx in 99% THF) didn't spray in cone-jet mode initially because of the low conductivity. More volatile and conductive solvent such as methanol was used in outer nozzle so that the open-matrix coating was achieved. Then, the closed film coating was obtained by adding the outer flow and changing the ratio between the inner and outer flow.

Example 3

The solution sample listed in the table of FIG. 26A was sprayed under the conditions provided therein. FIG. 26B shows images of the coating resulting from the spraying of the samples in cone-jet mode. The images for each solution are provided in higher and lesser magnification. The solution (2.25% SIBS+0.25% PTx in 97.5% THF) has high viscosity, which prevented it from being sprayed at cone-jet mode. Solvent blend was introduced into outer nozzle so that the closed film coating was achieved.

Example 4

The solution samples listed in the table of FIG. 27A were sprayed under the conditions provided therein. FIG. 27B shows images of the coatings resulting from the spraying of the samples in cone-jet mode. The images for each solution are provided in higher and lesser magnification. The solution (4.5% SIBS+0.5% PTx in 95% THF) has high viscosity, which prevents it from being sprayed at cone-jet mode. Solvent blend was introduced into outer nozzle so that the open-matrix and the closed film coatings were achieved.

Example 5

The solution samples listed in the table of FIG. 28A were sprayed under the conditions provided therein. FIG. 28B shows images of the coatings resulting from the spraying of the samples in cone-jet mode. The images for each solution are provided in higher and lesser magnification. An open matrix coating could be easily achieved with this solution (4.5% PLCL+0.5% DEX in 95% Acetone) because of the low boiling point and higher conductivity of acetone. In order to have a closed film coating, the acetone and chloroform blend was used as outer solvent.

Example 6

The solution samples listed in the table of FIG. 29A were sprayed under the conditions provided therein. FIG. 29B shows images of the coatings resulting from the spraying of the samples in cone-jet mode. The images for each solution are provided in higher and lesser magnification. Open matrix coating could be easily achieved with this solution (5% PLCL in 95% Acetone) because of the low boiling point and higher conductivity of acetone. In order to have closed film coating, the acetone and chloroform blend was used as outer solvent.

Example 7

The solution sample listed in the table of FIG. 30A was sprayed under the conditions provided therein. FIG. 29B shows images of the coating resulting from the spraying of the sample in cone-jet mode. The image for the solution was provided in higher and lesser magnification. The solution (1.8% PLCL+0.2% DEX in 82% THF and 16% MEOH) didn't spray at cone-jet mode initially. A small amount of methanol was added into outer nozzle to provide some conductivity. A closed film coating was achieved by this way.

Example 8

The solution sample listed in the table of FIG. 31 was sprayed under the conditions provided therein. FIG. 32 shows images of the coating resulting from the spraying of the sample in cone-jet mode. The images for the solution are provided in higher and lesser magnification. MEK has a boiling point of 79-80.5 C, but the conductivity is lower than methanol, which was the reason why this solution (0.9% SIBS+0.1% PTx in 69.7% THF and 29.3% MEK) didn't spray at cone-jet mode initially. A solvent blend of methanol and THF was added into outer nozzle to provide more conductivity. An open matrix coating was achieved by this way.

Example 9

The solution sample (2% DEX in 40% ethanol (ETOH) and 60% ACETONE) listed in the table of FIG. 33 was sprayed under the conditions provided therein. FIG. 34 shows images of the coating resulting from the spraying of the sample in cone-jet mode. The images for the solution are provided in higher and lesser magnification. Unlike the other example 1-10, this solution sample was sprayed using a triple concentric opening nozzle, like that described with reference to FIG. 7B. The triple nozzle was used to encapsulate the drug with the PLCL. Acetone was used at the outermost nozzle.

Figure 7B:
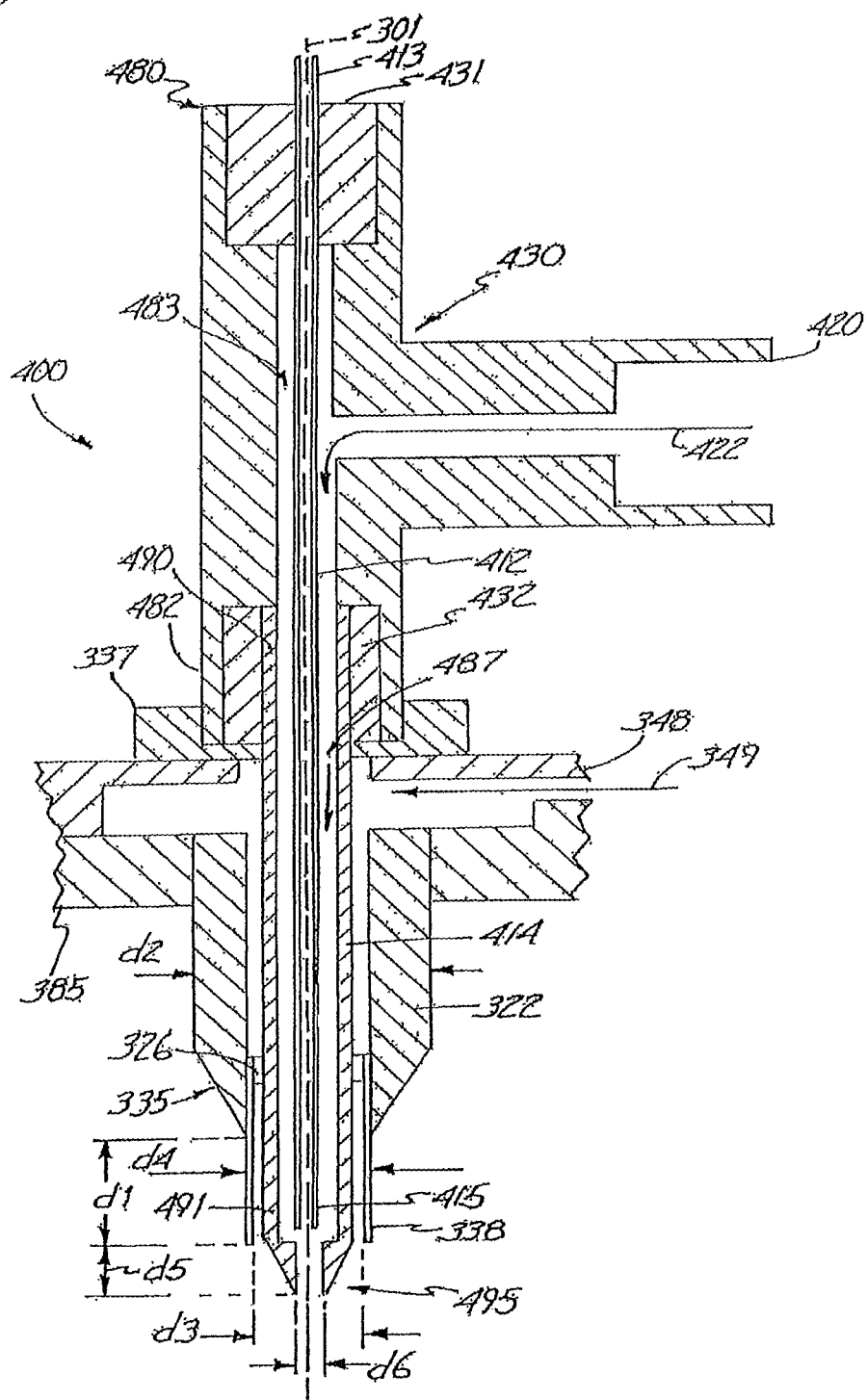
FIG. 7B shows a more detail diagram of one embodiment of a triple opening electrospray dispensing apparatus according to the present invention that may be controlled for applying one or more of the types of coatings such as generally shown in FIGS. 3A-3C.

The apparatus used to spray the coating was equivalent to that shown in and described with reference to FIG. 7A modified with the dual capillary tube distributor head 400 shown in and described with reference to FIG. 7B. The apparatus used was configured with a center capillary tube 413 having an outer diameter of about 558.8 μm (0.022 inches) and an inner diameter of about 304.8 μm (0.012 inches). The second capillary tube 414 concentric with the center capillary tube had an outer diameter of about 1041.4 μm (0.041 inches) and an inner diameter of about 685.8 μm (0.027 inches). The distance d1 shown in FIG. 7B from the end of tapered section 335 to the end of the metal casing 322 is about 1143 μm (0.045 inches). The diameter d2 of the first end 336 of the nozzle portion or metal casing 322 is about 6426 μm (0.253 inches). The outer diameter d4 of the second end 338 of the nozzle portion 322 is about 1549 μm (0.061 inches) and an inner diameter d3 of about 889 μm (0.035 inches). The distance d5 from the tip of the second end 338 of the nozzle portion 322 to the tip of the end of the second capillary tube 414 is about 508 μm (0.020 inches). The gap d6 at the tip of the second capillary tube 414 is about 685.8 μm (0.027 inches).

The dispensing device was constructed of various materials. Primarily, the conductive elements were constructed of stainless steel, the apparatus was used in a chamber made of plexiglass, and insulative parts thereof were made of a plastic, black delrin, material. A voltage of 4300 volts was applied to conductive element 312. The distance from the dispensing tip 495 of the second capillary tube 414 to the target was about 8 mm.

The inner capillary flow rate was 0.75 μl/min and the stream contained 2% dexamethasone in a 2:3 blend of acetone and ethanol. The second capillary flow rate was 1.5 μl/min and the stream was 5% PLCL in acetone. The third and outer nozzle flow rate was 5 μl/min and contained acetone only.

DISCUSSION REGARDING RESULTS

The electrospray coating system and process proved very flexible. The system was able to apply a range of polymers of differing performance qualities and solvent requirements. For each condition studied, a set of operating parameters was successfully identified that provided a cone-jet spray throughout the coating as well as the desired surface architecture. The system proved to be reliable and flexible enough to accommodate solvents over a range of polarities and conductivities.

A key element to the successful spray operation was the ability to merge solvent streams at the spray tip (e.g., a lower conductivity liquid spray composition including a polymer, drug and suitable solvent with a higher conductivity liquid diluent composition such as one that includes an addition of nitric acid). This feature of the spray nozzle design has permitted us to spray both polar solvents and non-polar solvents of extremely low conductivity.

Important objectives related to scale-up for manufacturing were identified. The system produced even coatings on all intricate surfaces of a stent without webbing or coating voids. Coating weights were uniform within a tight range during lot production. Reproducible coatings were produced with different surface characteristics, including the preservation of particle architecture. The strikingly different coating types achieved with PLCL polymer, just by altering the spray operating parameters, were noteworthy. The open-matrix coating has a much greater surface area and would be presumed to alter drug release characteristics.

This open matrix coating with its preserved nanoparticulate architecture, which we have now been able to replicate with two polymers having very different solvent requirements, is desirable, including potential variations that combine more than one active ingredient applied jointly or individually to create unique pharmacokinetics.

In view of the experiments, various modifications for the spray apparatus may be made to so as to include monitoring and controlling the process in view thereof with respect to any of the following: surface dust and fibers that contaminated the spray surface; imprecise controls on gas flow and composition through the spray chamber; inadequate evaporation rates of solvents; temperature fluctuations in ambient air; humidity fluctuations in ambient air; the need to eliminate gas bubbles from the spray feed material; the need to adjust the voltage of the power supply manually; need of bright lighting for video imaging and impact of ultraviolet light on cure of certain polymers; overspray of polymer and potentially toxic drug material and inability to clean all surfaces of the spray chamber without dismantling it; and build-up of coating overspray on the fixture leading to changes in the voltage settings required to operate in cone-jet mode.

For example such modification may include additional mechanisms to provide management of air or gas stream quality flow through improved filtration, temperature and moisture control, as well as flow rate controls. Improved control features will also enable operators to modify or facilitate solvent evaporation by improved temperature and gas control.

Yet further, automation of voltage control may be used. For example, such automation may include video imaging assessment of the cone-jet(s) during operation and, where indicated, feedback adjustments and/or immediate termination of spray operations. For example, if the cone-jet becomes unstable and begins to "spit," this can result in discharge of excessive solvent and cause blemishes on the coated surface. The "spit" can be seen visually and the effects reduced by stopping the spray or masking the spray surface, but there is often insufficient time to react. It should be possible through image monitoring and analysis to limit or prevent the impact on the spray surface and make needed process control modifications.

Yet further, improved light sources may be used, with the possibility of limiting certain wavelengths, and three-dimensional video camera positioning for better imaging of both the target and cone-jet may be used. Further, placing a moving stage and/or spray head parts outside of the actual spray chamber may be used to improve cleanability and the ability to contain more toxic spray elements during spray operations.

Still further, material containment and safe handling as well as treatment of the vented air or other gases passing through the spray chamber may be used to remove any stray particles.

References cited in the Examples above include:
1. Alexis F, Venkatraman S S, Rath S K, Boe F. In vitro study of release mechanisms of paclitaxel and rapamycin from drug-incorporated biodegradable stent matrices. J Controlled Release 98:67-74 (2004).

2. Chen D-R, Pui D Y H, Kaufman S L. Electrospraying of Conducting Liquids for Monodisperse Aerosol Generation in the 4 nm to 1.8 m Diameter Range, *J Aerosol Sci,* 26(6) 963-977 (1995).
3. Puskas J E, Chen Y, Dahman Y, Padavan D. Polyisobutylene-Based Biomaterials. Feature Article. J. Polym. Sci., Chem., 42(13):3091-3109 (2004).
4. Ranade S V, Miller K M, Richard R E, Chan A K, Allen M J, Helmus M N. Physical characterization of controlled release of paclitaxel from the TAXUS™ Express²™ drug-eluting stent. J Biomed Mater Res 71A:625-634 (2004).
5. Szycher M, Armini A, Bajgar C, Lucas A. Drug-eluting stents to prevent coronary restenosis. (www.implant-sciences.com/pdf/IMXpaperv2-rev2.pdf) (2002)
6. Verhoeven M L P M, Driessen, A A G, Paul A J, Brown A, Canry J-C, Hendriks M. DSIMS characterization of a drug-containing polymer-coated cardiovascular stent. J Controlled Release 96, 113-121 (2004).

All patents, patent documents, and references cited herein are incorporated in their entirety as if each were incorporated separately. This invention has been described with reference to illustrative embodiments and is not meant to be construed in a limiting sense. As described previously, one skilled in the art will recognize that other various illustrative applications may use the techniques as described herein to take advantage of the beneficial characteristics of the particles generated hereby. Various modifications of the illustrative embodiments, as well as additional embodiments to the invention, will be apparent to persons skilled in the art upon reference to this description.

What is claimed is:

1. A device to deliver one or more active ingredients, wherein the device comprises:
    a body of material presenting a surface comprising a polymer adapted to be rendered conductive such that one or more layers of electrospray particles are formable thereon; and
    a coating formed of electrospray particles deposited to adhere on the surface of the body of material, wherein the coating comprises one or more layers of coating material, wherein at least one layer of the one or more layers of coating material comprises an open matrix coating having an upper surface wherein a supermajority of the electrospray particles are visibly discrete but attached creating an irregular coating, wherein the open matrix coating comprises open regions extending at least one or more nominal particle diameters deeper in the upper surface, wherein the nominal diameter of the electrospray particles is in a range of about 1nm to about 2000 nm, and further wherein the upper surface of the open matrix coating comprises a rough surface wherein the surface area thereof is greater than about 1.2 times a surface area of a completely smooth surface having a substantially identical shape, and further wherein the open matrix coating comprises one or more active ingredients.

2. The device of claim 1, wherein the surface comprising the polymer comprises a dissolvable polymer.

3. The device of claim 2, wherein the dissolvable polymer comprises a water soluble polymer.

4. The device of claim 3, wherein the water soluble polymer comprises at least one of a polysaccharide, a protein, and a glycan.

5. The device of claim 4, wherein the water soluble polymer comprises at least a polysaccharide.

6. The device of claim 5, wherein the water soluble polymer comprises at least a cellulosic polymer.

7. The device of claim 3, wherein the water soluble polymer comprises at least one of an acrylate, polyethylene oxide, polyvinyl alcohol, polyacrylic acid, polyethylene glycol, and polyvinylpyrrolidone.

8. The device of claim 2, wherein the thickness of the dissolvable polymer is at least about 1 micron and not greater than 30 microns.

9. The device of claim 1, wherein the open matrix coating comprises one or more polymers and one or more active ingredients.

10. The device of claim 9, wherein the one or more active ingredients comprises at least a biologically active ingredient.

11. The device of claim 9, wherein the one or more active ingredients comprises a drug which remains in an amorphous state distributed throughout the one or more polymers.

12. The device of claim 9, wherein the one or more active ingredients comprise at least one pharmaceutically active compound.

13. The device of claim 9, wherein the one or more polymers of the open matrix coating comprises at least one of a cellulosic polymer, an acrylate, polyethylene oxide, polyvinyl alcohol, polyacrylic acid, polyethylene glycol, and polyvinylpyrrolidone.

14. The device of claim 13, wherein the one or more polymers of the open matrix coating comprises at least a cellulosic polymer.

15. The device of claim 1, wherein at least one layer of the one or more layers of coating material comprises an open matrix coating and at least one layer of the one or more layers of coating material comprises a closed film coating.

16. The device of claim 15, wherein the open matrix coating comprises a surface area greater than about 1.5 times the surface area of a completely smooth surface.

17. The device of claim 16, wherein the closed film coating comprises a surface area that is about equal to the surface area of a completely smooth surface.

18. The device of claim 1, wherein the device is configured to be used, at least in part, to penetrate and/or be positioned within a body.

19. The device of claim 18, wherein the device is configured as, at least in part, a medical closure.

20. The device of claim 18, wherein the device is configured as, at least in part, an implantable device.

21. The device of claim 1, wherein the open matrix coating comprises a surface area greater than about 1.5 times the surface area of a completely smooth surface.

22. A device to deliver one or more active ingredients, wherein the device comprises:
    a body of conductive material presenting a surface upon which one or more layers of electrospray particles are formable thereon; and
    a coating formed of electrospray particles deposited to adhere on the surface of the body of material, wherein the coating comprises one or more layers of coating material, wherein at least one layer of the one or more layers of coating material comprises an open matrix coating having an upper surface wherein a supermajority of the electrospray particles are visibly discrete but attached creating an irregular coating, wherein the open matrix coating comprises open regions extending at least one or more nominal particle diameters deeper in the upper surface, wherein the nominal diameter of the electrospray particles is in a range of about 1 nm to about 2000 nm, and further wherein the upper surface of the open matrix coating comprises a rough surface wherein the surface area thereof is greater than about 1.2 times a surface area of a completely smooth surface having a substantially identical shape, and further wherein the open matrix coating comprises one or more polymers and one or more active ingredients.

23. The device of claim 22, wherein the one or more active ingredients comprises at least a biologically active ingredient.

24. The device of claim 22, wherein the one or more active ingredients comprises a drug which remains in an amorphous state distributed throughout the one or more polymers.

25. The device of claim 22, wherein the one or more active ingredients comprise at least one pharmaceutically active compound.

26. The device of claim 22, wherein the one or more polymers of the open matrix coating comprises at least one of a cellulosic polymer, an acrylate, polyethylene oxide, polyvinyl alcohol, polyacrylic acid, polyethylene glycol, and polyvinylpyrrolidone.

27. The device of claim 26, wherein the one or more polymers of the open matrix coating comprises at least a cellulosic polymer.

28. The device of claim 22, wherein at least one layer of the one or more layers of coating material comprises an open matrix coating and at least one layer of the one or more layers of coating material comprises a closed film coating.

29. The device of claim 22, wherein the device is configured to be used, at least in part, to penetrate and/or be positioned within a body.

30. The device of claim 22, wherein the open matrix coating comprises a surface area greater than about 1.5 times the surface area of a completely smooth surface.

* * * * *